US009744365B2

(12) United States Patent
Davis et al.

(10) Patent No.: US 9,744,365 B2
(45) Date of Patent: Aug. 29, 2017

(54) PRESENTATION OF INFORMATION ASSOCIATED WITH MEDICAL DEVICE THERAPY

(75) Inventors: Jon P. Davis, St. Michael, MN (US); Steven M. Goetz, North Oaks, MN (US); James Zimmerman, Blaine, MN (US); Lynn A. Davenport, New Brighton, MN (US); Rajeev M. Sahasrabudhe, Maple Grove, MN (US); David Simons, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 1098 days.

(21) Appl. No.: 12/986,683

(22) Filed: Jan. 7, 2011

(65) Prior Publication Data

US 2011/0172744 A1 Jul. 14, 2011

Related U.S. Application Data

(60) Provisional application No. 61/293,561, filed on Jan. 8, 2010.

(51) Int. Cl.
*A61N 1/08* (2006.01)
*A61N 1/372* (2006.01)
(Continued)

(52) U.S. Cl.
CPC ..... *A61N 1/37247* (2013.01); *A61M 5/14276* (2013.01); *A61M 5/1723* (2013.01);
(Continued)

(58) Field of Classification Search
CPC .. A61N 1/37247; A61N 1/08; A61N 1/36135; A61N 1/36132; A61N 1/36071;
(Continued)

(56) References Cited

U.S. PATENT DOCUMENTS 5,431,691 A 7/1995 Snell et al.
5,513,645 A 5/1996 Jacobson et al.
(Continued)

OTHER PUBLICATIONS

International Search Report and Written Opinion dated Jun. 6, 2011 for corresponding PCT Application No. PCT/US2011/020558, (13 pgs.).

(Continued)

*Primary Examiner* — Rex R Holmes
(74) *Attorney, Agent, or Firm* — Shumaker & Sieffert, P.A.

(57) ABSTRACT

This disclosure is related to techniques for presenting therapy factors related to medical device therapy in a manner that allows a user, such as a patient or a clinician, to receive, comprehend and evaluate information relating to therapy delivered by the medical device efficiently. In one aspect, a method comprises obtaining a data set corresponding to a therapy factor associated with delivery of a medical therapy to a patient with a medical system including an implantable medical device, receiving a user selection associated with a subset of the data set, the subset of the data set including less than all the information relating to the therapy factor in the data set, and presenting a representation, corresponding to the subset of the data set, of the therapy factor on a display of a programmer.

54 Claims, 24 Drawing Sheets

(51) Int. Cl.
*A61M 5/142* (2006.01)
*A61M 5/172* (2006.01)
*G06F 19/00* (2011.01)
*A61N 1/36* (2006.01)

(52) U.S. Cl.
CPC ........... *A61N 1/08* (2013.01); *A61N 1/36132* (2013.01); *A61N 1/36135* (2013.01); *G06F 19/3406* (2013.01); *A61M 2205/502* (2013.01); *A61M 2230/62* (2013.01); *A61M 2230/63* (2013.01); *A61N 1/36071* (2013.01)

(58) Field of Classification Search
CPC ........... G06F 19/3406; A61M 5/14276; A61M 5/1723
USPC ........ 600/300, 587, 595; 607/2, 5, 6, 17, 19, 607/30, 32
See application file for complete search history.

(56) References Cited

U.S. PATENT DOCUMENTS

| | | | |
|---|---|---|---|
| 5,833,623 | A | 11/1998 | Mann et al. |
| 5,938,690 | A | 8/1999 | Law et al. |
| 6,250,309 | B1 | 6/2001 | Krichen et al. |
| 6,308,102 | B1 | 10/2001 | Sieracki et al. |
| 6,480,743 | B1 | 11/2002 | Kirkpatrick et al. |
| 6,597,954 | B1 | 7/2003 | Pless et al. |
| 6,599,250 | B2 | 7/2003 | Webb et al. |
| 6,609,032 | B1 | 8/2003 | Woods et al. |
| 6,622,048 | B1 | 9/2003 | Mann et al. |
| 6,654,642 | B2 | 11/2003 | North et al. |
| 6,675,044 | B2 | 1/2004 | Chen |
| 6,845,267 | B2 | 1/2005 | Harrison et al. |
| 7,181,286 | B2 | 2/2007 | Sieracki et al. |
| 7,558,629 | B2 | 7/2009 | Keimel et al. |
| 7,774,067 | B2 | 8/2010 | Keacher et al. |
| 7,778,851 | B2 | 8/2010 | Schoenberg et al. |
| 8,352,039 | B2 | 1/2013 | Davis et al. |
| 2001/0007950 | A1 | 7/2001 | North et al. |
| 2002/0103505 | A1 | 8/2002 | Thompson |
| 2002/0116036 | A1 | 8/2002 | Daignault, Jr. et al. |
| 2002/0165437 | A1 | 11/2002 | Chen |
| 2004/0122484 | A1 | 6/2004 | Hatlestad et al. |
| 2004/0143302 | A1 | 7/2004 | Sieracki et al. |
| 2004/0199217 | A1 | 10/2004 | Lee et al. |
| 2005/0085738 | A1 | 4/2005 | Stahmann et al. |
| 2005/0113887 | A1 | 5/2005 | Bauhahn et al. |
| 2005/0209645 | A1* | 9/2005 | Heruth et al. ............... 607/3 |
| 2006/0235472 | A1 | 10/2006 | Goetz et al. |
| 2006/0241720 | A1 | 10/2006 | Woods et al. |
| 2007/0135690 | A1 | 6/2007 | Nicholl |
| 2007/0150026 | A1 | 6/2007 | Bourget et al. |
| 2007/0244511 | A1 | 10/2007 | Weizman et al. |
| 2007/0244519 | A1 | 10/2007 | Keacher et al. |
| 2007/0249968 | A1* | 10/2007 | Miesel et al. ............. 600/595 |
| 2007/0299317 | A1 | 12/2007 | Hoyme et al. |
| 2008/0071581 | A1 | 3/2008 | Luttrell |
| 2009/0112289 | A1 | 4/2009 | Lee et al. |
| 2009/0281596 | A1 | 11/2009 | King et al. |
| 2010/0076787 | A1 | 3/2010 | Naylor et al. |
| 2010/0130831 | A1 | 5/2010 | Sato et al. |

OTHER PUBLICATIONS

InSync III Cardiac Resynchronization Therapy Pacemaker (CRT-P), http://www.medtronic.com/physician/brady/enpulse/quicklook.html, downloaded Mar. 2011 (3 pgs.).
Specialty EMR, Softwares Medical Record System, http://www.omnimd.com/html/emrsscreens.html, downloaded Mar. 2011 (2 pgs.).
Speciality EMR, Software for Clinical Practices in US, http://www.omnimd.com/html/EMRS.html, downloaded Mar. 2011 (2 pgs.).
EMR eClinicalWorks, http://www.eclinicalworks.com/code.php, downloaded Mar. 2011 (3 pgs.).
AspectMD TM Electronic Medical Record, Lightstream Solutions, http://www.lightstreamsolutions.com/aspectmd.html, downloaded Mar. 2011 (2 pgs.).
U.S. Appl. No. 12/771,652, filed Apr. 30, 2010, Davis et al.
U.S. Appl. No. 12/652,919, filed Jan. 6, 2011, Davis et al.
Office Action from U.S. Appl. No. 15/226,701, dated Sep. 6, 2016, 11 pp.
International Preliminary Report on Patentability from International Application No. PCT/US2011/020558, dated Jul. 10, 2012, 7 pp.
Preliminary Amendments to counterpart European Application No. 11700304.6, filed on Jul. 31, 2012, 6 pp.
Communication pursuant to Rules 161(1) and 162 EPC from counterpart European Application No. 11700304.6, dated Sep. 7, 2012, 2 pp.
Response to Communication dated Sep. 7, 2012, from counterpart European Application No. 11700304.6, filed on Mar. 12, 2013, 7 pp.
Communication pursuant to Article 94(3) EPC from counterpart European Application No. 11700304.6, dated May 11, 2015, 4 pp.
Response to Communication dated May 11, 2015, from counterpart European Application No. 11700304.6, filed on Sep. 14, 2015, 6 pp.
Communication pursuant to Article 94(3) EPC from counterpart European Application No. 11700304.6, dated Feb. 12, 2016, 4 pp.
Response to Communication dated Feb. 12, 2016, from counterpart European Application No. 11700304.6, filed on Aug. 22, 2016, 7 pp.
Communication pursuant to Article 94(3) EPC from counterpart European Application No. 11700304.6, dated Dec. 20, 2016, 4 pp.
Priority documents from International Application No. PCT/US2011/020558, filed Jan. 8, 2010, 145 pp.
Entry into the European phase before the European Patent Office, from counterpart European Application No. 11700304.6, dated May 21, 2012, 3 pp.
Entry into the European Phase from counterpart European Application No. 11700304.6, dated Aug. 1, 2012, 4 pp.
Communication of European publication No. and information on the Application of Article 67(3) EPC, from counterpart European Application No. 11700304.6, dated Oct. 17, 2012, 1 pp.
Written Opinion from International Searching Authority from counterpart International Application No. PCT/US2011/020558, dated Jun. 1, 2011, 6 pp.
Response to Examination Report dated Dec. 20, 2016, from counterpart European Application No. 1700304.6, filed on May 2, 2017, 12 pp.

* cited by examiner

PRESENTATION OF INFORMATION ASSOCIATED WITH MEDICAL DEVICE THERAPY

This application claims the benefit of U.S. Provisional Application No. 61/293,561 by Davis, entitled, "PRESENTATION OF INFORMATION ASSOCIATED WITH MEDICAL DEVICE THERAPY" and filed on Jan. 8, 2010, the entire content of which is incorporated herein by reference.

TECHNICAL FIELD

The disclosure relates to medical devices and, more particularly, to programmable medical devices that deliver therapy.

BACKGROUND

A variety of medical devices are used for chronic, e.g., long-term, delivery of therapy to patients suffering from a variety of conditions, such as chronic pain, tremor, Parkinson's disease, epilepsy, urinary or fecal incontinence, sexual dysfunction, obesity, or gastroparesis. As examples, electrical stimulation generators are used for chronic delivery of electrical stimulation therapies such as cardiac pacing, electrical stimulation, muscle stimulation, or the like. Pumps or other fluid delivery devices may be used for chronic delivery of therapeutic agents, such as drugs. Typically, such devices provide therapy continuously or periodically according to parameters contained within a program. A program may comprise respective values for each of a plurality of parameters, specified by a clinician.

Typically, a clinician uses a programmer, e.g., a computing device capable of communicating with implantable medical devices (IMDs) via device telemetry, to program an IMD for delivery of electrical stimulation therapy to a patient. In some cases, such clinician programmers may take the form of handheld and/or tablet-type computing devices.

A clinician may select values for a number of programmable therapy parameters in order to define the electrical stimulation therapy to be delivered to a patient. For example, the clinician may select a pulse voltage or pulse current amplitude and pulse width for a stimulation waveform to be delivered to the patient, as well as a rate at which the pulses are to be delivered to the patient. The clinician may also select as therapy parameters particular electrodes within an electrode set to be used to deliver the pulses, and the polarities of the selected electrodes. A group of parameter values may be referred to as a program in the sense that they drive the electrical stimulation therapy to be delivered to the patient.

In some cases, the patient may be allowed to activate and/or modify the therapy delivered by the medical device. For example, a patient may be provided with a patient programmer. The patient programmer communicates with a medical device to allow the patient to activate therapy and/or adjust therapy parameters. For example, an IMD, such as an implantable neurostimulator, may be accompanied by an external patient programmer that permits the patient to activate and deactivate electrical stimulation therapy and/or adjust the intensity of the delivered electrical stimulation.

SUMMARY

In general, the disclosure is related to techniques for presenting therapy factors related to medical device therapy in a manner that allows a user, such as a patient or a clinician, to receive, comprehend and evaluate information relating to therapy delivered by the medical device efficiently. For example, the techniques disclosed herein may be particularly applicable to posture-responsive therapy, such as an electrical stimulation therapy or drug delivery. In one aspect, a user may select a subset of a data set corresponding to a therapy factor associated with delivery of medical therapy on a programmer. The programmer then presents a representation of the subset of the data set to the user. In this manner, a user can select specific portions of the data set, e.g., portions representing a daily time period or a patient activity level, in order to more easily interpret the data set. The user may use his or her interpretation of the data set in order to evaluate the efficacy of the therapy and/or adjust the therapy.

In one aspect, a method comprises obtaining a data set corresponding to a therapy factor associated with delivery of a medical therapy to a patient with a medical system including an implantable medical device, receiving a user selection associated with a subset of the data set, the subset of the data set including less than all the information relating to the therapy factor in the data set, and presenting a representation, corresponding to the subset of the data set, of the therapy factor on a display of a programmer.

In another aspect, a programmer comprises a user interface, a telemetry circuit configured to transfer data to and from an implantable medical device (IMD), a display, and a processor. The processor is configured to: obtain a data set corresponding to a therapy factor associated with delivery of a medical therapy to a patient with the IMD and receive a user selection via the user interface. The user selection is associated with a subset of the data set, the subset of the data set including less than all the information relating to the therapy factor in the data set. The processor is configured to present a representation, corresponding to the subset of the data set, of the therapy factor on the display.

In another aspect, a system comprises: an implantable medical device (IMD) configured to deliver a medical therapy to a patient, a user interface, a telemetry circuit configured to transfer data to and from the IMD, a display, and programmer comprising a processor. The processor is configured to: obtain a data set corresponding to a therapy factor associated with delivery of a medical therapy to a patient with the IMD and receive a user selection via the user interface. The user selection is associated with a subset of the data set, the subset of the data set including less than all the information relating to the therapy factor in the data set. The processor is configured to present a representation, corresponding to the subset of the data set, of the therapy factor on the display.

The details of one or more aspects of this disclosure are set forth in the accompanying drawings and the description below. Other features, objects, and advantages will be apparent from the description and drawings, and from the claims.

DETAILED DESCRIPTION

Figure 1A:
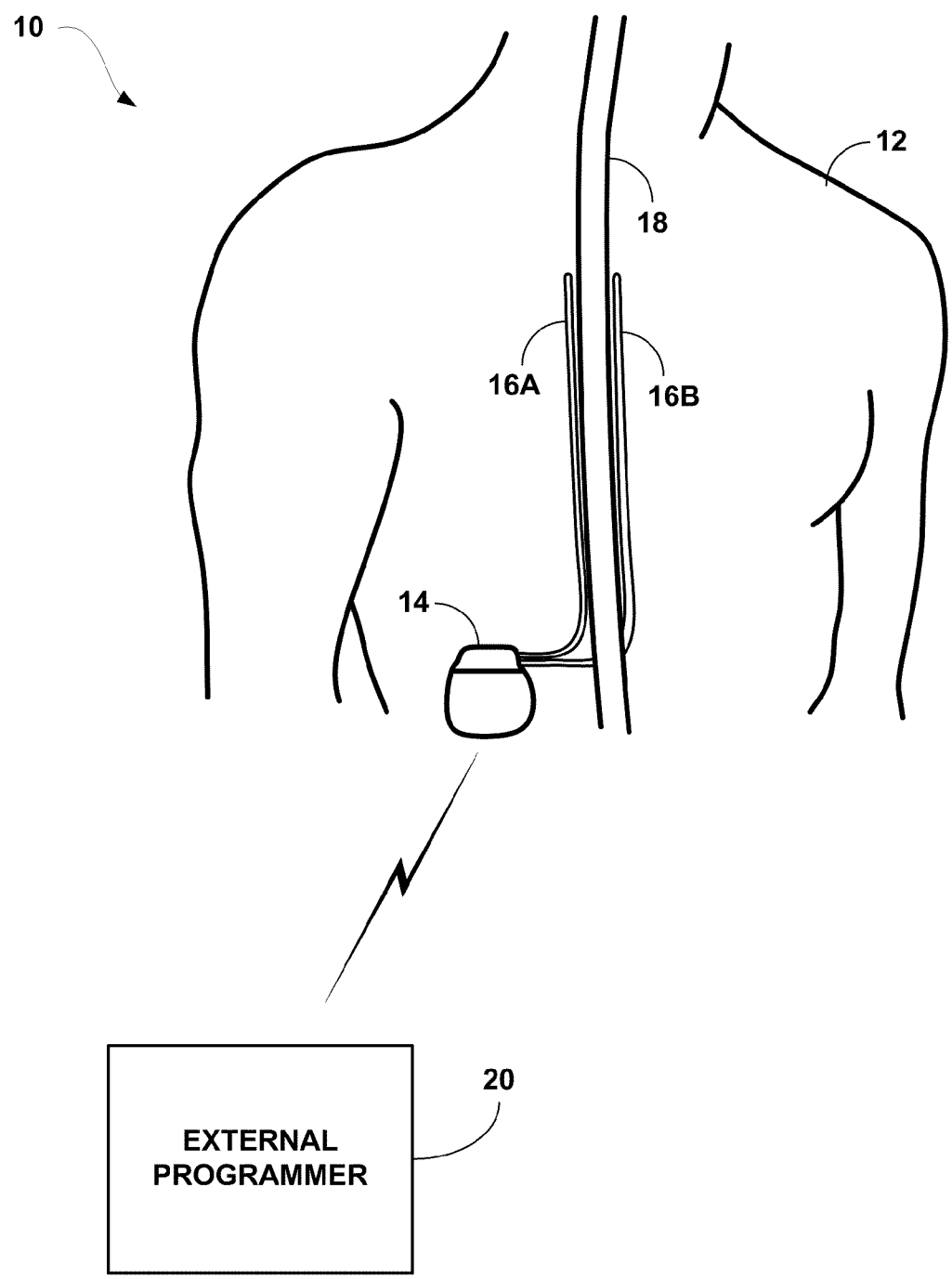
FIG. 1A is a conceptual diagram illustrating an implantable stimulation system including two implantable stimulation leads.

When receiving therapy from a medical device, the effectiveness of the therapy is often evaluated periodically by a clinician, e.g., during a patient-clinician consultation and/or a programming session for the medical device. During such a periodic evaluation, there is a variety of information relating to the therapy that can factor into the clinician's evaluation of the condition of the patient, the effectiveness of the therapy, and whether there should be any adjustments for continuing therapy. Such information is referred to herein as therapy factors. Therapy factors include, but are not limited to, therapy delivery history, historical physiological information about the patient, medical device status history, medical device diagnostic information, historical patient interactions with the medical device, and subjective patient feedback regarding the therapy and/or condition of the patient, each of which may be referred to as a therapy factor. A medical device may be configured to store one or more of these therapy factors and present such information to the clinician when interrogated by the clinician, e.g., during a programming session.

During clinician visits, it is useful for the clinician to receive, comprehend and evaluate information relating to therapy delivered by the medical device as efficiently as possible. Many therapy factors relating to therapy delivered by the medical device can be interrelated. As one example, at a particular point in time, the status of the medical device could relate to the therapy delivered by the medical device. A history of therapy delivered by a medical device might indicate that no therapy was delivered during a period of the history. Such information could be indicative of a problem with the medical device. However, if the clinician knew the medical device had a problem, such as a low charge level in the case of an electrical stimulator, and was therefore unable to deliver therapy during that period, the clinician would understand why the medical device did not delivery therapy during that period. Knowing that the period of non-delivery of therapy was caused by the low charge level of the electrical stimulator battery, the clinician would be better equipped to choose the best plan for preventing periods of non-delivery of therapy in the future. For example, the clinician could provide or emphasize instructions for charging the electrical stimulator battery to the patient at various times or intervals, or possibly adjust one or more therapy parameters to reduce power consumption.

This disclosure describes techniques for presenting therapy factors related to medical device therapy in a manner that allows a user, such as a patient or a clinician, to receive, comprehend and evaluate information relating to therapy delivered by the medical device efficiently. In one example, two or more therapy factors are presented to the user simultaneously, and may be presented to the user along a common timeline. This can allow the user to quickly recognize interrelationships between the presented therapy factors, and possibly make more informed decisions about changes or additions to therapy. For example, therapy factors may include therapy parameters for therapy applied to the patient, patient posture, battery charge history of a battery of the medical device, a subjective record of pain experienced by the patient, an objective record of one or more physiological conditions of the patient, and a record representative of electrode impedances for electrodes of medical leads associated with the neurostimulator. In some examples, the user may select the therapy factors that are presented along the common timeline. In other examples, various sets of therapy factors may be selected to form different, pre-processed views of the therapy factors. Objective records may represent data measured directly by a device, such as an IMD, whereas subjective data may represent data that relies upon a subjective input of a user, such as a patient. As an example, subject input could be a pain rating, pain map, paresthesia map, side effect rating, or the like. Examples of objective records include electrode impedance, an amount or other indication of time that a patient occupies various posture states, an amount or other indication of time that therapy is active, an amount or other indication of time that a particular therapy group, program or slot is used, or an amount or other indication of battery charge level or recharge interval. Examples of slot-based therapy programming are described in co-pending U.S. patent application Ser. No. 12/985,919 by Davis, et al., filed Jan. 6, 2011, titled "PROGRAMMING THERAPY DELIVERED BY IMPLANTABLE MEDICAL DEVICE," the content of which is incorporated by reference herein.

In another aspect, the user may select a historical period along which the therapy factors are displayed. A shorter historical period may provide higher resolution than a longer historical period. For example, a shorter historical period may permit therapy factors to be presented at closer intervals, such that more therapy factors can be shown per unit time. In this respect, a user can zoom-in to view a portion of data close-up, i.e., in high resolution or zoom-out to view data representing a longer historical period.

In another aspect, the user can select a subset of a historical period in which therapy factors are displayed. Such subsets may include data recorded during the mornings of the historical period, data recorded during the evenings of the historical period, data recorded during the night (sleeping time) of the historical period, weekends, work days or other subset of a historical period. In some examples, the information relating to the medical device therapy may be presented on a programmer associated with the medical devices, e.g., a clinician programmer or a patient programmer. Aspects of this disclosure may be useful to select and adjust therapy parameters effectively and efficiently. As one example, aspects of this disclosure can be applied to an electrical stimulator, such as an implantable neurostimulator, configured to treat the patient for chronic pain. As another example, aspects this disclosure can also be applied to a drug delivery system, such as an implantable drug pump, configured to treat the patient for chronic pain.

In some medical devices that deliver electrical stimulation or drug therapy, therapeutic efficacy may change as the patient changes between different posture states. In general, a posture state may refer to a patient posture or a combination of posture and activity levels. For example, some posture states, such as an upright posture state, may be sub-categorized as upright and active or upright and inactive. Other posture states, such as lying down posture states, may or may not have an activity component. Efficacy may refer, in general, to a combination of complete or partial alleviation of symptoms alone, or in combination with some degree of undesirable side effects.

Changes in posture state may cause changes in efficacy due to changes in distances between electrodes or other therapy delivery elements, e.g., due to temporary migration of leads or catheters caused by forces or stresses associated with different postures of the patient, or from changes in compression of patient tissue in different posture states. Also, posture state changes may present changes in symptoms or symptom levels, e.g., pain level. To achieve, enhance or maintain therapeutic efficacy, it may be desirable to adjust therapy parameters based on different postures and/or activities engaged by the patient to maintain effective stimulation therapy. Therapy parameters may be adjusted individually and directly or by selecting different programs or groups of programs defining different sets of therapy parameters.

A change in efficacy due to changes in posture state may require the patient to continually manage therapy by manually adjusting certain therapy parameters, such as amplitude, pulse rate, pulse width, electrode combination, or electrode polarity, or selecting different therapy programs to achieve more efficacious therapy throughout many different posture states. In some cases, a medical device may employ a posture state detector that detects the patient posture state. The medical device may subsequently adjust therapy parameters in response to different posture states. Therapy adjustments in response to different posture states may be fully automatic, semi-automatic in the sense that a user may provide approval of proposed changes, or user-directed in the sense that the patient may manually adjust therapy based on the posture state indication.

Electrical stimulation therapy may be provided to a patient in order to relieve symptoms from any number of conditions and diseases. An IMD that delivers electrical stimulation therapy may also employ a posture state sensor that is configured to sense which posture state the patient is engaged. The sensed posture state may then be associated with therapy adjustments made manually by the patient, i.e., patient adjustments, during the sensed posture state or multiple instances of the sensed posture state to allow a user to review the associations and modify stimulation parameters to better treat the patient.

When the patient makes a patient therapy adjustment, i.e., a change to one of the stimulation parameters that define the stimulation therapy, the therapy adjustment is intended for a particular posture state. Although most therapy adjustments may be made and intended for the posture state currently occupied by the patient, sometimes the patient may anticipate the next posture state and make the manual patient adjustment prior to moving to the intended posture state. Therefore, the system must associate the therapy adjustment with the anticipated posture state that the patient intends to occupy.

To accomplish this association, the system may implement a posture search timer for each instance of a sensed posture state, i.e., each time that a posture state is sensed. The posture search timer may have a search period and a posture stability timer may have a stability period that, when used together, allow the system to associate a therapy adjustment to a later posture state. The therapy adjustment is only associated with the final posture state if the final posture state is sensed within the search period of the posture state timer and continues for at least the stability period of the posture stability timer. In this sense, the system may correctly associate therapy parameters with posture states that the patient intended without making unintended associations.

In another example, the system may store associations between therapy adjustments and posture states. This may permit monitoring of patient therapy adjustments for multiple posture states over a period of time to aid in selection of automated therapy adjustments for use in delivery of posture-responsive therapy. Even when a therapy adjustment is made for a therapy program and posture state in which a therapy adjustment has already been made, all previously stored therapy adjustments may be maintained in memory to populate the therapy adjustment information record. If memory capacity for storage of therapy adjustments is limited, stored therapy adjustments may be overwritten according to any suitable technique for prioritizing which stored therapy adjustments should be saved. As an example, a first-in, first-out priority may be used. Association of a therapy adjustment with a posture state may permit a user to identify the posture state for which the patient intended to make the therapy adjustment.

An external programmer, such as a clinician programmer, may present the therapy adjustment information to the user via an output device of a user interface. For example, the presented therapy adjustment information may include minimum and/or maximum amplitude values from the therapy adjustments, the average amplitude value of the therapy adjustments, or the quantified number of therapy adjustments for each therapy program in each posture state. The user may then modify therapy parameters for one or more programs or program groups of programs based upon the presented information.

In other examples, the associations of therapy adjustments to posture states also may allow the user to quickly program stimulation parameters for therapy. An output device of the user interface of an external programmer, e.g., the clinician programmer, may present stimulation parameters, or a nominal therapy parameter, for each of the plurality of therapy programs from the therapy adjustments. The nominal therapy parameter for a particular posture may be a therapy parameter selected from the patient therapy adjustments stored in the IMD for the respective posture. The nominal therapy adjustment may be weighted or calculated according to an algorithm. An input device of the user interface may then allow the user to set the presented nominal therapy parameter to all therapy programs by receiving just one confirmation input from the user. The nominal therapy parameter may be the minimum amplitude of the therapy adjustments or the last therapy adjustments used, for example.

An output device of the user interface may also present a suggested therapy parameter based upon the therapy adjustments for each of the individual therapy programs. The user may then select or confirm the suggested therapy parameters for all of the plurality of therapy programs with one confirmation input via an input device of the user interface. Specifically, the suggested therapy parameter may be generated from a guided algorithm created to find the most efficacious therapy for the patient, instead of just a therapy adjustment stored in the IMD. The guided algorithm may implement any one or more of weighted averages, therapy adjustment trends, safe guards to protect against overstimulation, or any other therapy factors. In this manner, the clinician may not be burdened with the time needed to find the most efficacious therapy parameters for the patient, and each time the patient enters a different posture state, the therapy programs will deliver therapy with the most appropriate therapy parameters based on previous patient parameter adjustments while occupying such a posture state.

An input device and output device may be referred to collectively as a user interface. In some cases, the input and output devices may be associated with different devices. For example, in some cases, therapy adjustments may be made by a patient via a user interface associated with a patient programmer. Some information, such as information relating to therapy adjustments, postures, and the like, may be presented to a user via a clinician programmer or other device. In other cases, the input and output device may be associated with the same programmer. For example, a clinician programmer may present information relating to therapy adjustments and postures via an output device, and receive programming information from a user via an input device.

In addition, a programmer may be capable of associating therapy adjustments that have been intended by the patient for only a particular posture state. If the programmer recognizes that a received therapy adjustment is outside of a historical range of the prior stored therapy adjustments, the programmer may not make the association of the therapy adjustment to the posture state. However, the programmer may prompt the user to confirm the association and only make the association once the confirmation is received.

Once patient therapy adjustments are associated with different posture states, and then selected therapy adjustments to be made for such posture states based on the patient therapy adjustments, a medical device can automatically apply those selected therapy adjustments in response to detection of the posture states associated with the adjustments. In, this manner, a medical device can learn to automatically adjust therapy by associating patient postures with previous manual adjustments of the therapy. This posture-responsive therapy can reduce the number of manual adjustments by a patient and improve the efficacy of the treatment.

Various techniques described in this disclosure may be provided in an IMD, an external programmer for the IMD or a combination of both. For example, processors in the IMD and external programmer may perform various functions such as recording of therapy adjustment associations with particular programs and posture states.

In cases where association is performed by the IMD, therapy adjustments may be transmitted to the IMD from the programmer for not only adjustment of therapy delivered by the IMD, but also for use by the IMD in associating the adjustments with pertinent programs and postures states to support a recording mode for collection of such associations. In cases where association is performed by the external programmer, sensed posture states may be transmitted to the programmer from the IMD for not only recording and presentation of posture states, but also for use by the programmer in associating the adjustments with pertinent programs and postures states to support a recording mode for collection of such associations.

Hence, in many instances, functionality described in this disclosure may be performed by the IMD, the programmer, or a combination of both. Therefore, descriptions of particular functionality in the IMD or programmer should not be considered limiting of the techniques, devices and systems, as broadly described in this disclosure.

FIG. 1A is a schematic diagram illustrating an implantable stimulation system 10 including a pair of implantable electrode arrays in the form of stimulation leads 16A and 16B. Although the techniques described in this disclosure may be generally applicable to a variety of medical devices including external and IMDs, application of such techniques to IMDs and, more particularly, implantable electrical stimulators such as neurostimulators will be described for purposes of illustration. More particularly, the disclosure will refer to an implantable spinal cord stimulation (SCS) system for purposes of illustration, but without limitation as to other types of medical devices.

As shown in FIG. 1A, system 10 includes an IMD 14 and external programmer 20 shown in conjunction with a patient 12. In the example of FIG. 1A, IMD 14 is an implantable electrical stimulator configured for spinal cord stimulation (SCS), e.g., for relief of chronic pain or other symptoms. Again, although FIG. 1A shows an IMD, other examples may include an external stimulator, e.g., with percutaneously implanted leads. Stimulation energy is delivered from IMD 14 to spinal cord 18 of patient 12 via one or more electrodes of implantable leads 16A and 16B (collectively "leads 16"). In some applications, such as spinal cord stimulation (SCS) to treat chronic pain, the adjacent implantable leads 16 may have longitudinal axes that are substantially parallel to one another.

Although FIG. 1A is directed to SCS therapy, system 10 may alternatively be directed to any other condition that may benefit from stimulation therapy. For example, system 10 may be used to treat tremor, Parkinson's disease, epilepsy, urinary or fecal incontinence, sexual dysfunction, obesity, or gastroparesis. In this manner, system 10 may be configured to provide therapy taking the form of deep brain stimulation (DBS), pelvic floor stimulation, gastric stimulation, or any other stimulation therapy. In addition, patient 12 is ordinarily a human patient.

Each of leads 16 may include electrodes (not shown in FIG. 1), and the parameters for a program that controls delivery of stimulation therapy by IMD 14 may include information identifying which electrodes have been selected for delivery of stimulation according to a stimulation program, the polarities of the selected electrodes, i.e., the electrode configuration for the program, and pulse voltage or current amplitude, pulse rate, and pulse width of stimulation delivered by the electrodes. Delivery of stimulation pulses will be described for purposes of illustration. However, stimulation may be delivered in other forms such as continuous waveforms. Programs that control delivery of other therapies by IMD 14 may include other parameters, e.g., such as dosage amount, rate, or the like for drug delivery.

In the example of FIG. 1A, leads 16 carry one or more electrodes that are placed adjacent to the target tissue of the spinal cord. One or more electrodes may be disposed at a distal tip of a lead 16 and/or at other positions at intermediate points along the lead. Leads 16 may be implanted and coupled to IMD 14. Alternatively, as mentioned above, leads 16 may be implanted and coupled to an external stimulator, e.g., through a percutaneous port. In some cases, an external stimulator may be a trial or screening stimulation that used on a temporary basis to evaluate potential efficacy to aid in consideration of chronic implantation for a patient. In additional examples, IMD 14 may be a leadless stimulator with one or more arrays of electrodes arranged on a housing of the stimulator rather than leads that extend from the housing.

The stimulation may be delivered via selected combinations of electrodes carried by one or both of leads 16. The target tissue may be any tissue affected by electrical stimulation energy, such as electrical stimulation pulses or waveforms. Such tissue includes nerves, smooth muscle, and skeletal muscle. In the example illustrated by FIG. 1A, the target tissue is spinal cord 18. Stimulation of spinal cord 18 may, for example, prevent pain signals from traveling through the spinal cord and to the brain of the patient. Patient 12 may perceive the interruption of pain signals as a reduction in pain and, therefore, efficacious therapy results.

The deployment of electrodes via leads 16 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays may include electrode segments, which may be arranged at respective positions around a periphery of a lead, e.g., arranged in the form of one or more segmented rings around a circumference of a cylindrical lead.

In the example of FIG. 1A, stimulation energy is delivered by IMD 14 to the spinal cord 18 to reduce the amount of pain perceived by patient 12. As described above, IMD 14 may be used with a variety of different pain therapies, such as peripheral nerve stimulation (PNS), peripheral nerve field stimulation (PNFS), DBS, cortical stimulation (CS), pelvic floor stimulation, gastric stimulation, and the like. The electrical stimulation delivered by IMD 14 may take the form of electrical stimulation pulses or continuous stimulation waveforms, and may be characterized by controlled voltage levels or controlled current levels, as well as pulse width and pulse rate in the case of stimulation pulses.

In some examples, IMD 14 may deliver stimulation therapy according to one or more programs. A program defines one or more parameters that define an example of the therapy delivered by IMD 14 according to that program. For example, a program that controls delivery of stimulation by IMD 14 in the form of pulses may define a voltage or current pulse amplitude, a pulse width, a pulse rate, for stimulation pulses delivered by IMD 14 according to that program. Moreover, therapy may be delivered according to multiple programs, each program associated with a program group, wherein multiple programs are contained within each of a multiple of groups. Therapy may also be delivered according to multiple programs, each program associated with a single slot designated for treating a specific area of pain.

Each program group may support an alternative therapy selectable by patient 12, and IMD 14 may deliver therapy according to the multiple programs. IMD 14 may rotate through the multiple programs of the group when delivering stimulation such that numerous conditions of patient 12 are treated. As an illustration, in some cases, stimulation pulses formulated according to parameters defined by different programs may be delivered on a time-interleaved basis. For example, a group may include a program directed to leg pain, a program directed to lower back pain, and a program directed to abdomen pain. In this manner, IMD 14 may treat different symptoms substantially simultaneously.

During use of IMD 14 to treat patient 12, movement of patient 12 among different posture states may affect the ability of IMD 14 to deliver consistent efficacious therapy. For example, leads 16 may migrate toward IMD 14 when patient 12 bends over, resulting in displacement of electrodes and possible disruption in delivery of effective therapy. Stimulation energy transferred to target tissue may be reduced due to electrode migration, causing reduced efficacy in terms of relief of symptoms such as pain. As another example, leads 16 may be compressed toward spinal cord 18 when patient 12 lies down. Such compression may cause an increase in the amount of stimulation energy transferred to target tissue. In this case, the amplitude of stimulation therapy may need to be decreased to avoid causing patient 12 additional pain or unusual sensations, which may be considered undesirable side effects that undermine overall efficacy.

Also, posture state changes may present changes in symptoms or symptom levels, e.g., pain level. In some examples, to avoid interruptions in effective therapy, IMD 14 may include a posture state module that detects the patient posture state. The IMD automatically adjusts stimulation according to the detected posture state. For example, the posture state module may include one or more accelerometers that detect when patient 12 occupies a posture state in which it is appropriate to decrease the stimulation amplitude, e.g., when patient 12 lies down. The IMD may automatically reduce stimulation amplitude so that patient 12 does not manually have to do so. Example posture states may include "Upright," "Upright and Active," "Lying Down," and so forth.

In some examples, IMD 14 may be configured to automatically decrease stimulation amplitude when it detects that patient 12 lies down. The amplitude adjustment may be configured to be decreased at a rate suitable to prevent undesirable effects, e.g., such as the effects due to the compression of leads 16 towards spinal cord 18 when patient 12 lies down. In some examples, IMD 14 may be configured to decrease the stimulation amplitude to a suitable amplitude value substantially immediately upon detection by IMD 14 that patient 12 is lying down. In other examples, the stimulation amplitude may not be decreased substantially immediately by IMD 14 upon detection of patient 12 lying down, but instead IMD 14 may decrease the stimulation amplitude to a suitable amplitude level at a rate of change that is suitable to prevent patient 12 from experiencing undesirable stimulation effects, e.g., due to increased transfer of stimulation energy in the changed anatomical position. In some examples, IMD 14 may substantially instantaneously decrease the stimulation amplitude of stimulation delivered according to a particular program, or all active programs, to a suitable amplitude value when IMD detects that patient 12 is lying down.

Reduced efficacy due to increased coupling or decreased coupling of stimulation energy to target tissue may occur due to changes in posture and/or activity level associated with patient posture state. To avoid or reduce possible disruptions in effective therapy due to posture state changes, IMD 14 may include a posture state module that detects the posture state of patient 12 and causes the IMD 14 to automatically adjust stimulation according to the detected posture state. For example, a posture state module may include a posture state sensor, such as an accelerometer, that detects when patient 12 lies down, stands up, or otherwise changes posture.

In response to a posture state indication by the posture state module, IMD 14 may change a program group, program, stimulation amplitude, pulse width, pulse rate, and/or one or more other parameters, groups or programs to maintain therapeutic efficacy. When a patient lies down, for example, IMD 14 may automatically reduce stimulation amplitude so that patient 12 does not need to reduce stimulation amplitude manually. In some cases, IMD 14 may communicate with external programmer 20 to present a proposed change in stimulation in response to a posture state change, and receive approval or rejection of the change from a user, such as patient 12 or a clinician, before automatically applying the therapy change. In some examples, posture state detection may also be used to provide notifications, such as providing notification via a wireless link to a care giver that a patient has potentially experienced a fall.

Referring still to FIG. 1A, a user, such as a clinician or patient 12, may interact with a user interface of external programmer 20 to program IMD 14. The user interface may include an output device for presentation of information, and an input device to receive user input. Programming of IMD 14 may refer generally to the generation and transfer of commands, programs, or other information to control the operation of IMD 14. For example, external programmer 20 may transmit programs, parameter adjustments, program selections, group selections, or other information to control the operation of IMD 14, e.g., by wireless telemetry. As one example, external programmer 20 may transmit parameter adjustments to support therapy changes due to posture changes by patient 12. As another example, a user may select programs or program groups. Again, a program may be characterized by an electrode combination, electrode polarities, voltage or current amplitude, pulse width, pulse rate, and/or duration. A group may be characterized by multiple programs that are delivered simultaneously or on an interleaved or rotating basis.

As another example, separate programs may be selected for a set of program slots. Each slot may include one or more programs that form therapy options for the slot, and each slot may target a different symptom or area of pain. One program may be selected from each slot, where the selection of a program in one slot is independent of the programs selected in other slots. In other words, therapy is defined by multiple slots, and each slot is defined by selection of one of a plurality of programs designated for the slot. In applying stimulation therapy, programs for different slots may be delivered on an interleaved or rotating basis. In some examples, the programs in the slots may be delivered in fast succession such that a patient experiences near-constant paresthesia from the combined effect of each of the programs simultaneously.

During the delivery of stimulation therapy, patient 12 may make patient therapy adjustments, i.e., patient adjustments to one or more parameters of a therapy via an input device of a user interface of a programmer, to customize the therapy either after patient 12 moves to a different posture state or in anticipation of the next posture state. In examples where IMD 14 stores all patient therapy adjustments associated with a specific posture state, IMD 14 may implement a method to ensure that patient therapy adjustments are associated with the correct posture state intended by patient 12 when the therapy adjustment was made. The patient 12 may occupy the posture state multiple times such that there are multiple instances of the sensed posture state.

Each time the patient 12 occupies the posture state, the patient may enter one or more therapy adjustments. Hence, the multiple therapy adjustments may be obtained over multiple instances of the sensed posture state, i.e., multiple, different times at which the patient occupies the posture state over a time interval, and associated with the posture state. IMD 14 may use a posture search timer having a search period and a posture stability timer having a stability period after any therapy adjustment in order to match the therapy adjustment to the appropriate posture state. The therapy adjustment is associated with a final posture state only when a final posture state began within the search period of the posture search timer and lasts beyond the stability period of the posture stability timer. In this manner, therapy adjustments are not associated with a posture state that does not remain constant or is not occupied soon enough after the therapy adjustment.

In some cases, external programmer 20 may be characterized as a physician or clinician programmer if it is primarily intended for use by a physician or clinician. In other cases, external programmer 20 may be characterized as a patient programmer if it is primarily intended for use by a patient, e.g., for entry of patient input to specify patient adjustments to one or more therapy parameters. A patient programmer is generally accessible to patient 12 and, in many cases, may be a portable device that may accompany the patient throughout the patient's daily routine. In general, a physician or clinician programmer may support selection and generation of programs by a clinician for use by IMD 14, whereas a patient programmer may support adjustment and selection of such programs by a patient during ordinary use, either manually or via other user input media.

External programmer 20 may present posture state data stored in IMD 14 from the detected posture states of patient 12. The posture state data may be acquired by external programmer 20 to generate posture state information, e.g., therapy adjustment information. IMD 14 may also store any associations between the therapy adjustments and the posture states for which the therapy adjustments were intended, i.e., therapy adjustment information. By recording all therapy adjustments made for a program in each of the posture states, including each of the multiple instances of the sensed posture states, external programmer 20 may be able to present therapy adjustment information to the user that indicates patient 12 desired stimulation parameters based upon parameter use. For example, the user may be able to identify the most recent stimulation parameters desired by patient 12, the minimum and maximum allowable amplitudes, or even the quantified number of therapy adjustments to indicate that patient 12 is either satisfied with a program or cannot readily find suitable parameters for a program with many therapy adjustments.

The therapy adjustment information may be presented in any number of different manners. For example, an output device of the user interface may present each program of a group and the respective number of therapy adjustments and the range of such amplitudes defined by the therapy adjustments. Alternatively, an output device of the user interface may also, or instead, present the last (i.e., most recent) amplitude used by patient 12 to deliver therapy with each program. In any manner, the therapy adjustment information may be presented in a graphical, numerical, or textual mode on external programmer 20. The user may be able to customize the presentation of the therapy adjustment information in other examples. In addition, as discussed in further detail below with respect to FIGS. 13-25, the therapy adjustment information may be presented along a common timeline in combination with other therapy factors associated with delivering electrical stimulation therapy to patient 12.

In some examples, external programmer 20 may utilize the associations of the therapy adjustments to posture states in order to further minimize time needed to program all therapy programs. When presenting the amplitude ranges of the therapy adjustments for each therapy program, the user may be able to provide a single confirmation input that sets the amplitude for all programs to some nominal therapy parameter, for example. The nominal therapy parameter may be a minimum amplitude associated with the program and posture state, the last amplitude associated with the program and posture state, or some other therapy parameter already stored by IMD 14 in association with each therapy program and posture state. The therapy parameter may be referred to as nominal in the sense that it refers to a parameter value by a name that is descriptive of the value, rather than to a specific, absolute parameter value. In cases where a program has not been associated with any therapy adjustment, no new stimulation parameter may be programmed to the program.

In other examples, external programmer 20 may generate a suggested therapy parameter based upon the therapy adjustment information and a guided algorithm. The suggested therapy parameter may be a specific therapy parameter value that is visible to the user, but is signified as being suggested by the guided algorithm. The guided algorithm may be an equation, set of equations, look-up table, or other technique for generating a suggested therapy parameter that may define stimulation therapy effective to patient 12. In this manner, external programmer 20 analyzes the therapy adjustment information for the most appropriate stimulation parameters that fit the desires of the user. The guided algorithm may generate a low or high weighted average, a safe average that minimizes the chances of overstimulation, a trend target that weights more recent patient adjustments to therapy greater than older therapy adjustments, or even an intergroup average that looks to therapy adjustments to programs in different groups that provide stimulation therapy. In any case, the user may be able to program the plurality of programs with each suggested therapy parameter with the selection of a single confirmation input.

IMD 14 may be constructed with a biocompatible housing, such as titanium or stainless steel, or a polymeric material such as silicone or polyurethane, and surgically implanted at a site in patient 12 near the pelvis. IMD 14 may also be implanted in patient 12 at a location minimally noticeable to patient 12. Alternatively, IMD 14 may be external with percutaneously implanted leads. For SCS, IMD 14 may be located in the lower abdomen, lower back, upper buttocks, or other location to secure IMD 14. Leads 16 may be tunneled from IMD 14 through tissue to reach the target tissue adjacent to spinal cord 18 for stimulation delivery.

At the distal tips of leads 16 are one or more electrodes (not shown) that transfer the electrical stimulation from the lead to the tissue. The electrodes may be electrode pads on a paddle lead, circular (e.g., ring) electrodes surrounding the body of leads 16, conformable electrodes, cuff electrodes, segmented electrodes, or any other type of electrodes capable of forming unipolar, bipolar or multipolar electrode configurations for therapy. In general, ring electrodes arranged at different axial positions at the distal ends of leads 16 will be described for purposes of illustration.

Figure 1B:
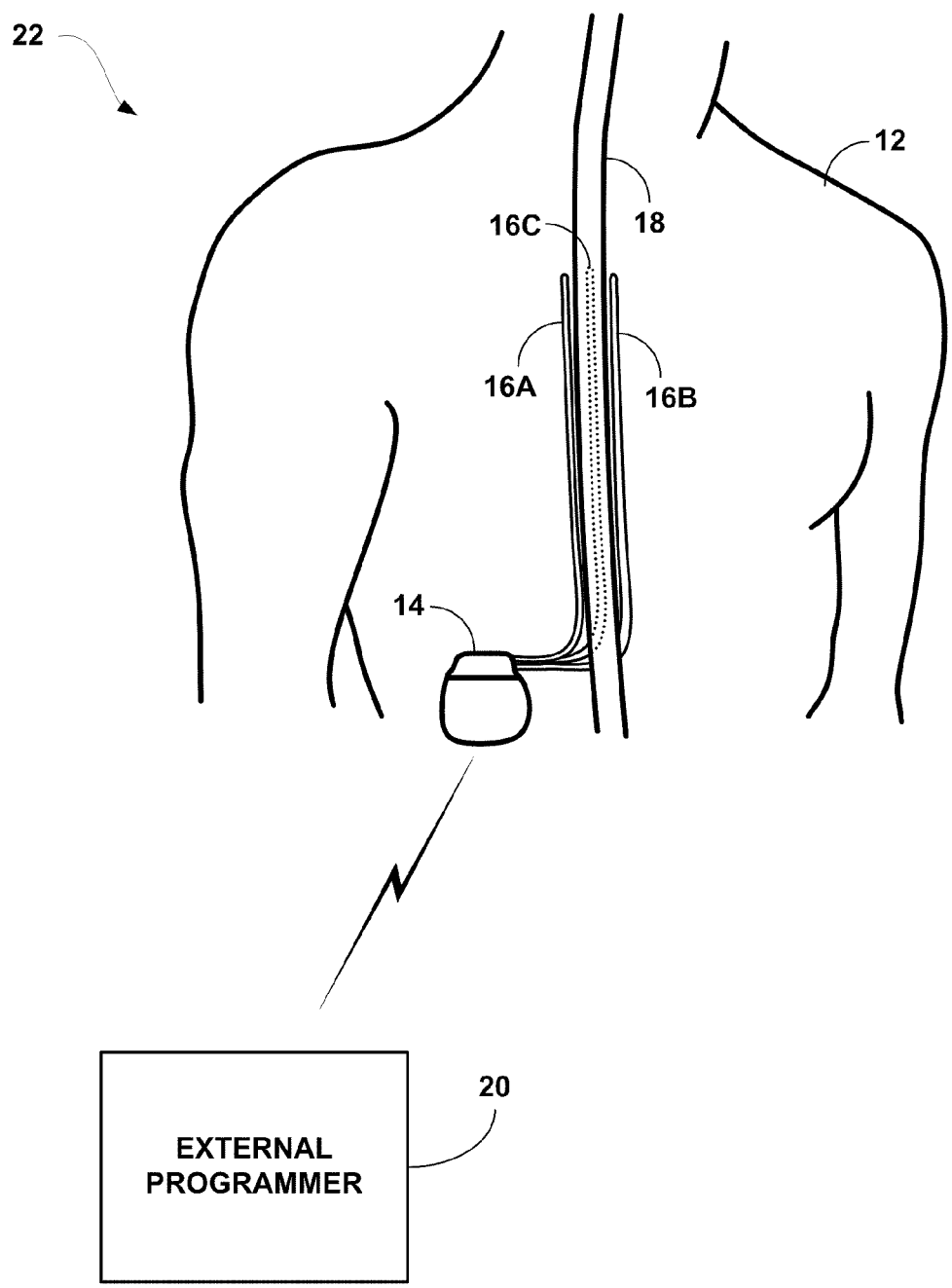
FIG. 1B is a conceptual diagram illustrating an implantable stimulation system including three implantable stimulation leads.

FIG. 1B is a conceptual diagram illustrating an implantable stimulation system 22 including three implantable stimulation leads 16A, 16B, 16C (collectively leads 16). System 22 generally conforms to system 10 of FIG. 1A, but includes a third lead along spinal cord 18. Accordingly, IMD 14 may deliver stimulation via combinations of electrodes carried by all three leads 16, or a subset of the three leads. The third lead, e.g., lead 16C, may include a greater number of electrodes than leads 16A and 16B and be positioned between leads 16A and 16B or on one side of either lead 16A or 16B. External programmer 20 may be initially told the number and configuration of leads 16 in order to appropriately program stimulation therapy.

For example, leads 16A and 16B could include four electrodes, while lead 16C includes eight or sixteen electrodes, thereby forming a so-called 4-8-4 or 4-16-4 lead configuration. Other lead configurations, such as 8-16-8, 8-4-8, 16-8-16, 16-4-16, are possible. In some cases, electrodes on lead 16C may be smaller in size and/or closer together than the electrodes of leads 16A or 16B. Movement of lead 16C due to changing activities or postures of patient 12 may, in some instances, more severely affect stimulation efficacy than movement of leads 16A or 16B. Patient 12 may further benefit from the ability of IMD 14 to detect posture states and associated changes and automatically adjust stimulation therapy to maintain therapy efficacy in a three lead system 22.

Figure 1C:
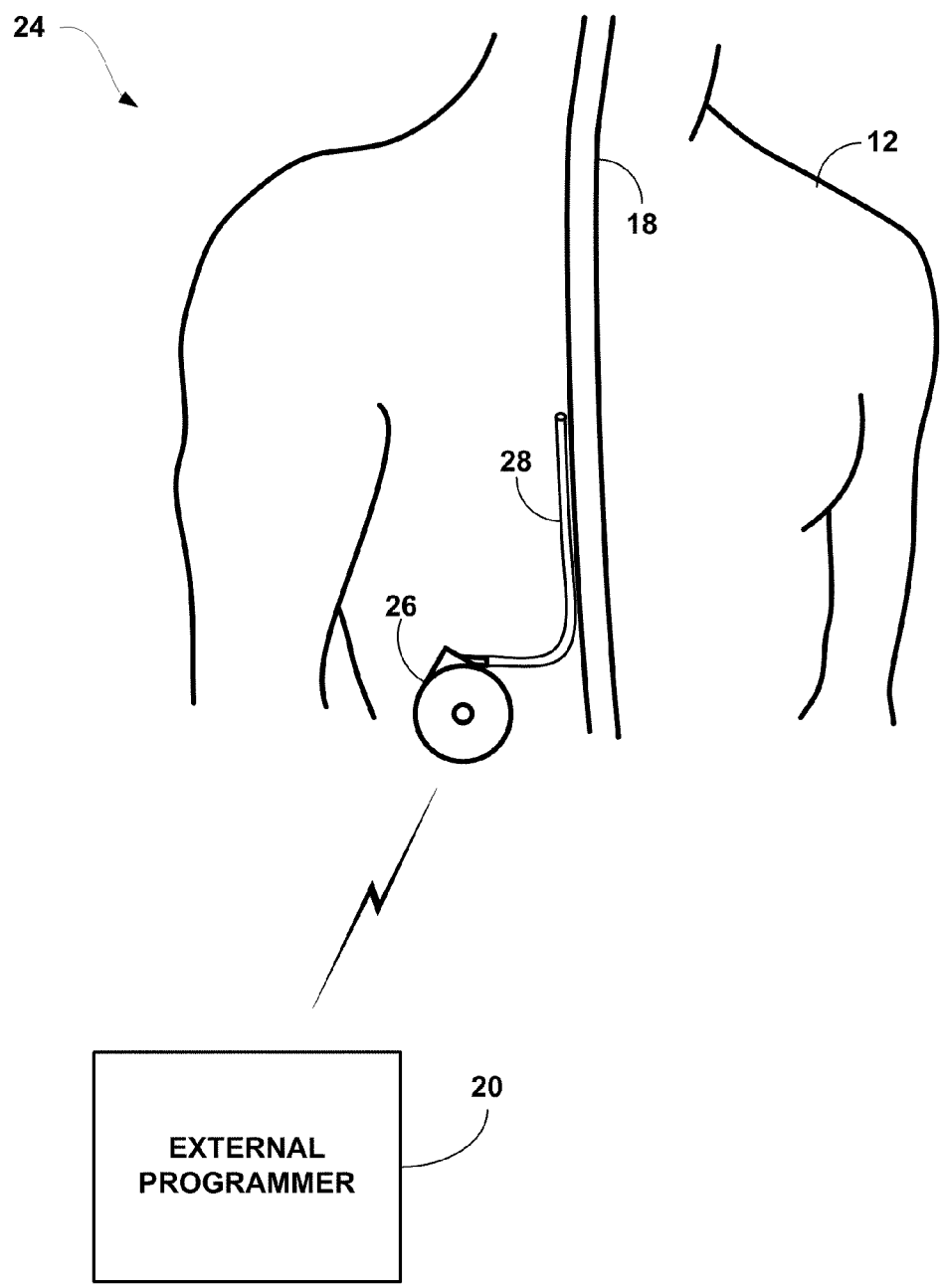
FIG. 1C is a conceptual diagram illustrating an implantable drug delivery system including a delivery catheter.

FIG. 1C is a conceptual diagram illustrating an implantable drug delivery system 24 including one delivery catheter 28 coupled to IMD 26. As shown in the example of FIG. 1C, drug delivery system 24 is substantially similar to systems 10 and 22. However, drug delivery system 24 performs the similar therapy functions via delivery of drug stimulation therapy instead of electrical stimulation therapy. IMD 26 functions as a drug pump in the example of FIG. 1C, and IMD 26 communicates with external programmer 20 to initialize therapy or modify therapy during operation. In addition, IMD 26 may be refillable to allow chronic drug delivery.

Although IMD 26 is shown as coupled to only one catheter 28 positioned along spinal cord 18, additional catheters may also be coupled to IMD 26. Multiple catheters may deliver drugs or other therapeutic agents to the same anatomical location or the same tissue or organ. Alternatively, each catheter may deliver therapy to different tissues within patient 12 for the purpose of treating multiple symptoms or conditions. In some examples, IMD 26 may be an external device which includes a percutaneous catheter that forms catheter 28 or that is coupled to catheter 28, e.g., via a fluid coupler. In other examples, IMD 26 may include both electrical stimulation as described in IMD 14 and drug delivery therapy.

IMD 26 may also operate using parameters that define the method of drug delivery. IMD 26 may include programs, or groups of programs, that define different delivery methods for patient 12. For example, a program that controls delivery of a drug or other therapeutic agent may include a titration rate or information controlling the timing of bolus deliveries. Patient 12 may use external programmer 20 to adjust the programs or groups of programs to regulate the therapy delivery.

Similar to IMD 14, IMD 26 may include a posture state module that monitors the patient 12 posture state and adjusts therapy accordingly. For example, the posture state module may indicate that patient 12 transitions from lying down to standing up. IMD 26 may automatically increase the rate of drug delivered to patient 12 in the standing position if patient 12 has indicated that pain increased when standing. This automated adjustment to therapy based upon posture state may be activated for all or only a portion of the programs used by IMD 26 to deliver therapy.

Figure 2:
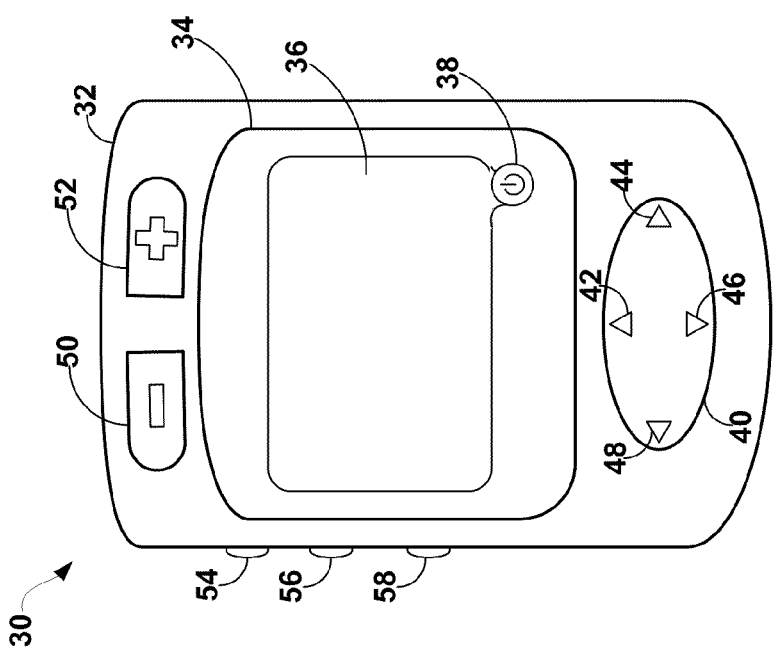
FIG. 2 is a conceptual diagram illustrating an example patient programmer for programming stimulation therapy delivered by an IMD.

FIG. 2 is a conceptual diagram illustrating an example patient programmer 30 for programming stimulation therapy delivered by an IMD. Patient programmer 30 is an example of external programmer 20 illustrated in FIGS. 1A, 1B and 1C and may be used with either IMD 14 or IMD 26. In alternative examples, patient programmer 30 may be used with an external medical device. As shown in FIG. 2, patient programmer 30 provides a user interface (not shown) for a user, such as patient 12, to manage and program stimulation therapy. Patient programmer 30 is protected by housing 32, which encloses circuitry necessary for patient programmer 30 to operate.

Patient programmer 30 also includes display 36, which may form part of an output device of a user interface, power button 38, increase button 52, decrease button 50, sync button 58, stimulation ON button 54, and stimulation OFF button 56. Cover 34 protects display 36 from being damaged during use of patient programmer 30. Patient programmer 30 also includes control pad 40 which forms part of an input device of a user interface and allows a user to navigate through items displayed on display 36 in the direction of arrows 42, 44, 46, and 48. In some examples, the buttons and pad 40 may take the form of soft keys (e.g., with functions and contexts indicated on display 36), with functionality that may change, for example, based on current programming operation or user preference. In alternative examples, display 36 may be a touch screen in which patient 12 may interact directly with display 36 without the use of control pad 40 or even increase button 52 and decrease button 50.

In the illustrated example, patient programmer 30 is a hand held device. Patient programmer 30 may accompany patient 12 throughout a daily routine. In some cases, patient programmer 30 may be used by a clinician when patient 12 visits the clinician in a hospital or clinic. In other examples, patient programmer 30 may be a clinician programmer that remains with the clinician or in the clinic and is used by the clinician and/or patient 12 when the patient is in the clinic. In the case of a clinician programmer, small size and portability may be less important. Accordingly, a clinician programmer may be sized larger than a patient programmer, and it may provide a larger screen for more full-featured programming.

Housing 32 may be constructed of a polymer, metal alloy, composite, or combination material suitable to protect and contain components of patient programmer 30. In addition, housing 32 may be partially or completely sealed such that fluids, gases, or other elements may not penetrate the housing and affect components therein. Power button 38 may turn patient programmer 300N or OFF as desired by patient 12. Patient 12 may control the illumination level, or backlight level, of display 36 by using control pad 40 to navigate through the user interface and increase or decrease the illumination level with decrease and increase buttons 50 and 52. In some examples, illumination may be controlled by a knob that rotates clockwise and counter-clockwise to control patient programmer 30 operational status and display 36 illumination. Patient programmer 30 may be prevented from turning OFF during telemetry with IMD 14 or another device to prevent the loss of transmitted data or the stalling of normal operation. Alternatively, patient programmer 30 and IMD 14 may include instructions that handle possible unplanned telemetry interruption, such as battery failure or inadvertent device shutdown.

Display 36 may be a liquid crystal display (LCD), dot matrix display, organic light-emitting diode (OLED) display, touch screen, or similar monochrome or color display capable of providing visible information to patient 12. Display 36 may provide a user interface regarding current stimulation therapy, posture state information, provide a user interface for receiving feedback or medication input from patient 12, display an active group of stimulation programs, and display operational status of patient programmer 30 or IMDs 14 or 26. For example, patient programmer 30 may provide a scrollable list of groups, and a scrollable list of programs within each group, via display 36.

Display 36 may present a visible posture state indication. In addition, display 36 may present therapy adjustment information stored with IMD 14 and even present nominal or suggested therapy parameters for a plurality of programs. Patient 12 may then selectively set the plurality of programs to the respective nominal or suggested therapy parameters via a single confirmation input. As described herein, patient programmer 30 may be configured to perform any tasks described with respect to clinician programmer 60 (described below in reference to FIG. 3) or another external programmer 20.

Control pad 40 allows patient 12 to navigate through items displayed on display 36. Patient 12 may press control pad 40 on any of arrows 42, 44, 46, and 48 in order to move to another item on display 36 or move to another screen not currently shown on the display. In some examples, pressing the middle of control pad 40 may select any item highlighted in display 36. In other examples, scroll bars, a scroll wheel, individual buttons, or a joystick may perform the complete or partial functions of control pad 40. In alternative examples, control pad 40 may be a touch pad that allows patient 12 to move a cursor within the user interface displayed on display 36 to manage therapy or review posture state information.

Decrease button 50 and increase button 52 provide an input mechanism for patient 12. In general, decrease button 50 may decrease the value of a highlighted stimulation parameter every time the decrease button is pressed. In contrast, increase button 52 may increase the value of a highlighted stimulation parameter one step every time the increase button is pressed. While buttons 50 and 52 may be used to control the value of any stimulation parameter, buttons 50 and 52 may also control patient feedback input. When either of buttons 50 and 52 is selected, patient programmer 30 may initialize communication with IMD 14 or 26 to change therapy accordingly.

When depressed by patient 12, stimulation ON button 54 directs programmer 30 to generate a command for communication to IMD 14 that turns on stimulation therapy. Stimulation OFF button 56 turns off stimulation therapy when depressed by patient 12. Sync button 58 forces patient programmer 30 to communicate with IMD 14. When patient 12 enters an automatic posture response screen of the user interface, pressing sync button 58 turns on the automatic posture response to allow IMD 14 to automatically change therapy according to the posture state of patient 12. Pressing sync button 58 again, when the automatic posture response screen is displayed, turns off the automatic posture response. In the example of FIG. 2, patient 12 may use control pad 40 to adjust the volume, contrast, illumination, time, and measurement units of patient programmer 30.

In some examples, buttons 54 and 56 may be configured to perform operational functions related to stimulation therapy or the use of patient programmer 30. For example, buttons 54 and 56 may control the volume of audible sounds produced by programmer 20, wherein button 54 increases the volume and button 56 decreases the volume. Button 58 may be pressed to enter an operational menu that allows patient 12 to configure the user interface of patient programmer 30 to the desires of patient 12. For example, patient 12 may be able to select a language, backlight delay time, display 36 brightness and contrast, or other similar options. In alternative examples, buttons 50 and 52 may control all operational and selection functions, such as those related to audio volume or stimulation therapy.

Patient programmer 30 may take other shapes or sizes not described herein. For example, patient programmer 30 may take the form of a clam-shell shape, similar to some cellular phone designs. When patient programmer 30 is closed, some or all elements of the user interface may be protected within the programmer. When patient programmer 30 is opened, one side of the programmer may contain a display while the other side may contain input mechanisms. In any shape, patient programmer 30 may be capable of performing the requirements described herein. Alternative examples of patient programmer 30 may include other input mechanisms such as a keypad, microphone, camera lens, or any other media input that allows the user to interact with the user interface provided by patient programmer 30.

In alternative examples, the buttons of patient programmer 30 may perform different functions than the functions provided in FIG. 2 as an example. In addition, other examples of patient programmer 30 may include different button layouts or different numbers of buttons. For example, patient programmer 30 may even include a single touch screen that incorporates all user interface functionality with a limited set of buttons or no other buttons.

Figure 3:
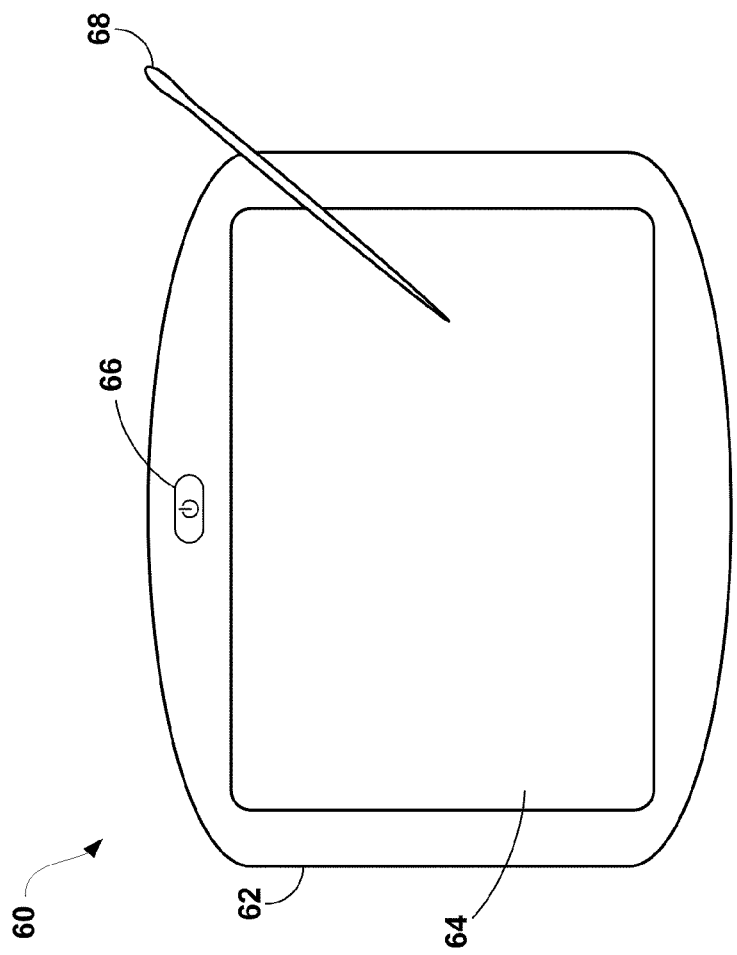
FIG. 3 is a conceptual diagram illustrating an example clinician programmer for programming stimulation therapy delivered by an IMD.

FIG. 3 is a conceptual diagram illustrating an example clinician programmer 60 for programming stimulation therapy delivered by an IMD. Clinician programmer 60 is an example of external programmer 20 illustrated in FIGS. 1A, 1B and 1C and may be used with either IMD 14 or IMD 26. In alternative examples, clinician programmer 60 may be used with an external medical device. Clinician programmer 60 is protected by housing 62, which encloses circuitry necessary for clinician programmer 60 to operate.

As shown in FIG. 3, clinician programmer 60 provides a user interface (not shown) for a user, such as a clinician, physician, technician, or nurse, to manage and program stimulation therapy. Clinician programmer 60 is used by the clinician or other user to modify and review therapy to patient 12. The clinician may define each therapy parameter value for each of the programs that define stimulation therapy. The therapy parameters, such as amplitude, may be defined specifically for each of the posture states that patient 12 will be engaged in during therapy. In addition, the clinician may use clinician programmer 60 to define each posture state of patient 12 by using the posture cones described herein or some other technique for associating posture state sensor output to the posture state of patient 12.

In addition, clinician programmer 60 may be used to simultaneously review two or more therapy factors. As an example, clinician programmer 60 may permit a user to review objective posture state information to monitor the progress and therapy efficacy of patient 12. As discussed in further detail below with respect to FIGS. 13-25, objective posture state information may be presented along a common timeline in combination with other therapy factors associated with delivering therapy to a patient. For example, such information may include two or more therapy factors such as an objective record of the electrical stimulation therapy delivered to the patient, a record of patient posture, a record of a battery charge history a battery of the neurostimulator, a subjective record of pain experienced by the patient, an objective record of one or more physiological conditions of the patient, and a record representative of electrode impedances for electrodes of medical leads associated with the neurostimulator. A clinician may select what therapy factors are presented on a common timeline on a screen of display 64. If not already available in memory of clinician programmer 60, therapy factors clinician programmer 60 retrieves the information from IMD 14, IMD 26 and/or patient programmer 30 following the request to present the information in order to present the information to the clinician or other user via display 64.

Clinician programmer 60 includes display 64 and power button 66. In the example of FIG. 3, display 64 is a touch screen that accepts user input via touching certain areas within display 64. The user may use stylus 68 to touch display 64 and select virtual buttons, sliders, keypads, dials, or other such representations presented by the user interface shown by display 64. In some examples, the user may be able to touch display 64 with a finger, pen, or any other pointing device. In alternative examples, clinician programmer 60 may include one or more buttons, keypads, control pads, touch pads, or other devices that accept user input, similar to patient programmer 30.

In the illustrated example, clinician programmer 60 is a hand held device. Clinician programmer 60 may be used within the clinic or on in-house patient calls. Clinician programmer 60 may be used to communicate with multiple IMDs 14 and 26 within different patients. In this manner, clinician programmer 60 may be capable of communicating with many different devices and retain patient data separate for other patient data. In some examples, clinician programmer 60 may be a larger device that may be less portable, such as a notebook computer, workstation, or event a remote computer that communicates with IMD 14 or 26 via a remote telemetry device.

Most, if not all, of clinician programmer 60 functions may be completed via the touch screen of display 64. The user may program stimulation therapy, modify programs or groups, retrieve stored therapy data, retrieve posture state information, define posture states and other activity information, change the contrast and backlighting of display 64, or any other therapy related function. In addition, clinician programmer 60 may be capable of communicating with a networked server in order to send or receive an email or other message, retrieve programming instructions, access a help guide, send an error message, or perform any other function that may be beneficial to prompt therapy.

Clinician programmer 60 may also allow the clinician to view historical therapy adjustment information stored in IMD 14 during therapy. As mentioned previously, the therapy adjustment information includes any associations created between therapy parameter value adjustments and posture states for each program that delivers automatic posture responsive stimulation. The clinician may initially orient IMD 14 to patient 12 and enable IMD 14 to store any associations as therapy adjustment information. Clinician programmer 60 may then acquire the therapy adjustment information from IMD 14 and present the information to the clinician in order to allow continued effective therapy modifications.

In some examples, clinician programmer 60 may also allow the clinician to adjust the search period of the posture search timer and the stability period of the posture stability timer. The posture search timer and the posture stability timer enable IMD 14 to determine the posture state with which a therapy adjustment should be associated. Depending upon the condition of patient 12 or the clinician preferences, the clinician may desire to adjust the search period and stability period to most accurately reflect the intentions of patient 12. For example, if patient 12 has a habit of adjusting therapy long before making a change to the posture state or patient 12 takes a long time to assume a desired posture state, the clinician may desire to increase the search period and stability period in order to properly associate the therapy adjustment with the intended posture state. In some examples, clinician programmer 60 may suggest appropriate search periods and stability periods for patients diagnosed with particular conditions that may hinder their movement or involve multiple oscillations in posture state before settling on the final posture state.

In addition, clinician programmer 60 may present nominal and suggested therapy parameters to the clinician based upon the stored therapy adjustment information in IMD 14. In one example, clinician programmer 60 may simply present an amplitude range determined by the therapy adjustments for each program and posture state. The clinician may then set the amplitude of each program to a nominal therapy parameter presented on display 64 of clinician programmer 60. For example, the nominal therapy parameter may be the minimum amplitude used by patient 12 for each program. Alternatively, clinician programmer 60 may present the last therapy adjustment for each program and posture state, or an average therapy adjustment. Clinician programmer 60 may then set the therapy parameter for all displayed programs with a single confirmation input from the clinician. This single input may decrease clinician programming time and overall programming complexity.

Further, clinician programmer 60 may present a suggested therapy parameter to the clinician for each program and posture state that is based upon the therapy adjustment information. The suggested therapy parameter may or may not be a parameter that was used from a therapy adjustment. Clinician programmer 60 may utilize a guided algorithm that attempts to generate a suggested therapy parameter that the clinician desires to free the clinician from manually determining the best therapy parameter for each program. Clinician programmer 60 may utilize one algorithm or receive a guided algorithm input from the clinician that customizes how clinician programmer 60 generates the suggested therapy parameters. For example, clinician programmer 60 may use a target trend guided algorithm that weights more recent therapy adjustments so that the suggested therapy parameters are more representative of recent patient 12 response to stimulation therapy.

In some cases, all processing may be performed in IMD 14 and distributed to clinician programmer 60 only for presentation to the clinician. Alternatively, IMD 14, clinician programmer 60, patient programmer 30, or another computing device may share in the processing duties of therapy adjustment information and any other data prior to presenting the information on clinician programmer 60. In other examples, IMD 14 may simply transfer raw data to an external programmer 20 or other computing device for data processing necessary to perform the tasks described herein. Accordingly, methods described in this disclosure may be implemented within IMD 14, programmer 30, programmer 60, or within a combination of such components.

Housing 62 may be constructed of a polymer, metal alloy, composite, or combination material suitable to protect and contain components of clinician programmer 60. In addition, housing 62 may be partially or completely sealed such that fluids, gases, or other elements may not penetrate the housing and affect components therein. Power button 66 may turn clinician programmer 60 ON or OFF as desired by the user. Clinician programmer 60 may require a password, biometric input, or other security measure to be entered and accepted before the user can use clinician programmer 60.

Clinician programmer 60 may take other shapes or sizes not described herein. For example, clinician programmer 60 may take the form of a clam-shell shape, similar to some cellular phone designs. When clinician programmer 60 is closed, at least a portion of display 64 is protected within housing 62. When clinician programmer 60 is opened, one side of the programmer may contain a display while the other side may contain input mechanisms. In any shape, clinician programmer 60 may be capable of performing the requirements described herein.

Figure 4:
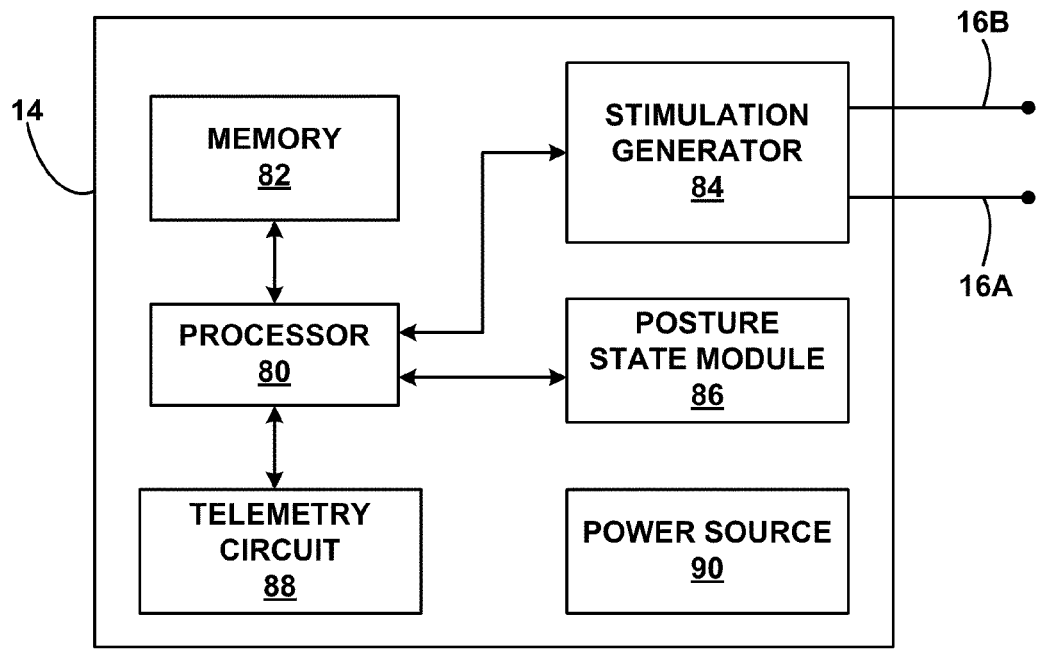
FIG. 4 is a functional block diagram illustrating various components of an implantable electrical stimulator.

FIG. 4 is a functional block diagram illustrating various components of an IMD 14. In the example of FIG. 4, IMD 14 includes a processor 80, memory 82, stimulation generator 84, posture state module 86, telemetry circuit 88, and power source 90. The stimulation generator 84 forms a therapy delivery module. Memory 82 may store instructions for execution by processor 80, stimulation therapy data, posture state information, posture state indications, and any other information regarding therapy or patient 12. Therapy information may be recorded for long-term storage and retrieval by a user, and the therapy information may include any data created by or stored in IMD 14. Memory 82 may include separate memories for storing instructions, posture state information, therapy adjustment information, program histories, other therapy factors associated with the delivery of therapy and any other data that may benefit from separate physical memory modules.

Processor 80 controls stimulation generator 84 to deliver electrical stimulation via electrode combinations formed by electrodes in one or more electrode arrays. For example, stimulation generator 84 may deliver electrical stimulation therapy via electrodes on one or more leads 16, e.g., as stimulation pulses or continuous waveforms. Components described as processors within IMD 14, external programmer 20 or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination.

Stimulation generator 84 may include stimulation generation circuitry to generate stimulation pulses or waveforms and switching circuitry to switch the stimulation across different electrode combinations, e.g., in response to control by processor 80. In particular, processor 80 may control the switching circuitry on a selective basis to cause stimulation generator 84 to deliver electrical stimulation to selected electrode combinations and to shift the electrical stimulation to different electrode combinations in a first direction or a second direction when the therapy must be delivered to a different location within patient 12. In other examples, stimulation generator 84 may include multiple current sources to drive more than one electrode combination at one time. In this case, stimulation generator 84 may decrease current to the first electrode combination and simultaneously increase current to the second electrode combination to shift the stimulation therapy.

An electrode configuration, e.g., electrode combination and associated electrode polarities, may be represented by a data stored in a memory location, e.g., in memory 82, of IMD 14. Processor 80 may access the memory location to determine the electrode combination and control stimulation generator 84 to deliver electrical stimulation via the indicated electrode combination. To adjust electrode combinations, amplitudes, pulse rates, or pulse widths, processor 80 may command stimulation generator 84 to make the appropriate changes to therapy according to instructions within memory 82 and rewrite the memory location to indicate the changed therapy. In other examples, rather than rewriting a single memory location, processor 80 may make use of two or more memory locations.

When activating stimulation, processor 80 may access not only the memory location specifying the electrode combination but also other memory locations specifying various stimulation parameters such as voltage or current amplitude, pulse width and pulse rate. Stimulation generator 84, e.g., under control of processor 80, then makes use of the electrode combination and parameters in formulating and delivering the electrical stimulation to patient 12.

According to examples described herein, such stimulation parameters may be adjusted to modify stimulation therapy delivered by IMD 14 based on the detected posture state of patient 12. In some examples, processor 80 may detect a posture state of patient 12 via posture state module 86 that indicates that a modification of the stimulation therapy is appropriate, e.g., according to instructions stored in memory 82. Processor 80 may access instructions for modifying the stimulation therapy based on the patient 12 posture state, e.g., by changing from a stimulation program appropriate for the previous posture state to a stimulation program appropriate for patient's current posture state.

An exemplary range of electrical stimulation parameters likely to be effective in treating chronic pain, e.g., when applied to spinal cord 18, are listed below. While stimulation pulses are described, stimulation signals may be of any of a variety of forms such as sine waves or the like.

1. Pulse Rate: between approximately 0.5 Hz and 1200 Hz, more preferably between approximately 5 Hz and 250 Hz, and still more preferably between approximately 30 Hz and 130 Hz.

2. Amplitude: between approximately 0.1 volts and 50 volts, more preferably between approximately 0.5 volts and 20 volts, and still more preferably between approximately 1 volt and 10 volts. In other embodiments, a current amplitude may be defined as the biological load in the voltage that is delivered. For example, the range of current amplitude may be between approximately 0.1 milliamps (mA) and 50 mA.

3. Pulse Width: between about 10 microseconds and 5000 microseconds, more preferably between approximately 100 microseconds and 1000 microseconds, and still more preferably between approximately 180 microseconds and 450 microseconds.

In other applications, different ranges of parameter values may be used. For deep brain stimulation (DBS), as one example, alleviation or reduction of symptoms associated with Parkinson's disease, essential tremor, epilepsy or other disorders may make use of stimulation having a pulse rate in the range of approximately 0.5 to 1200 Hz, more preferably 5 to 250 Hz, and still more preferably 30 to 185 Hz, and a pulse width in the range of approximately 10 microseconds and 5000 microseconds, more preferably between approximately 60 microseconds and 1000 microseconds, still more preferably between approximately 60 microseconds and 450 microseconds, and even more preferably between approximately 60 microseconds and 150 microseconds. Amplitude ranges such as those described above with reference to SCS, or other amplitude ranges, may be used for different DBS applications.

Processor 80 accesses stimulation parameters in memory 82, e.g., as programs and groups of programs. Upon selection of a particular program group, processor 80 may control stimulation generator 84 to deliver stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate. In addition, each program may specify a particular electrode combination for delivery of stimulation. Again, the electrode combination may specify particular electrodes in a single array or multiple arrays, e.g., on a single lead or among multiple leads. Processor 80 also may control telemetry circuit 88 to send and receive information to and from external programmer 20. For example, telemetry circuit 88 may send information to and receive information from patient programmer 30.

Posture state module 86 allows IMD 14 to sense the patient posture state, e.g., posture, activity or any other static position or motion of patient 12. In the example of FIG. 4, posture state module 86 may include one or more posture state sensors, e.g., one or more accelerometers such as three-axis accelerometers, capable of detecting static orientation or vectors in three-dimensions. Example accelerometers may include micro-electro-mechanical accelerometers. In other examples, posture state module 86 may alternatively or additionally include one or more gyroscopes, pressure transducers or other sensors to sense the posture state of patient 12. Posture state information generated by posture state module 86 and processor 80 may correspond to an activity, posture, or posture and activity undertaken by patient 12 or a gross level of physical activity, e.g., activity counts based on footfalls or the like.

Posture state information from posture state module 86 may be stored in memory 82 to be later reviewed by a clinician, used to adjust therapy, presented as a posture state indication to patient 12, or some combination thereof. As an example, processor 80 may record the posture state parameter value, or output, of the 3-axis accelerometer and assign the posture state parameter value to a certain predefined posture indicated by the posture state parameter value. In this manner, IMD 14 may be able to track how often patient 12 remains within a certain posture defined within memory 82. IMD 14 may also store which group or program was being used to deliver therapy when patient 12 was in the sensed posture. Further, processor 80 may also adjust therapy for a new posture when posture state module 86 indicates that patient 12 has in fact changed postures. Therefore, IMD 14 may be configured to provide posture state-responsive stimulation therapy to patient 12. Stimulation adjustments in response to posture state may be automatic or semi-automatic (subject to patient approval). In many cases, fully automatic adjustments may be desirable so that IMD 14 may react more quickly to posture state changes.

As described herein, the posture state data, or raw data of the posture state information, is stored by system 10 to be used at a later time. The posture state information may also be used in addition to the therapy adjustment information when the user desires to view more detailed information related to the posture states engaged by patient 12. Memory 82 may store all of the posture state data detected during therapy or use of IMD 14, or memory 82 may periodically offload the posture state data to clinician programmer 60 or a different external programmer 20 or device. In other examples, memory 82 may reserve a portion of the memory to store recent posture state data easily accessible to processor 80 for analysis. In addition, older posture state data may be compressed within memory 82 to require less memory storage until later needed by external programmer 20 or processor 80.

A posture state parameter value from posture state module 86 that indicates the posture state of patient 12 may constantly vary throughout the daily activities of patient 12. However, a certain activity (e.g., walking, running, or biking) or a posture (e.g., standing, sitting, or lying down) may include multiple posture state parameter values from posture state module 86. In this manner, a posture state may include a broad range of posture state parameter values. Memory 82 may include definitions for each posture state of patient 12. In one example, the definitions of each posture state may be illustrated as a cone in three-dimensional space. Whenever the posture state parameter value, e.g., a sensed coordinate vector, from the three-axis accelerometer of posture state module 86 resides within a predefined cone, processor 80 indicates that patient 12 is in the posture state of the cone. In other examples, posture state parameter value from the 3-axis accelerometer may be compared to a look-up table or equation to determine the posture state in which patient 12 currently resides.

Posture state-responsive stimulation may allow IMD 14 to implement a certain level of automation in therapy adjustments. Automatically adjusting stimulation may free patient 12 from the constant task of manually adjusting therapy parameters each time patient 12 changes posture or starts and stops a certain posture state. Such manual adjustment of stimulation parameters can be tedious, requiring patient 12 to, for example, depress one or more keys of patient programmer 30 multiple times during the patient posture state to maintain adequate symptom control. Alternatively, patient 12 may be unable to manually adjust the therapy if patient programmer 30 is unavailable or patient 12 is preoccupied. In some embodiments, patient 12 may eventually be able to enjoy posture state responsive stimulation therapy without the need to continue making changes for different postures via patient programmer 30. Instead, patient 12 may transition immediately or over time to fully automatic adjustments based on posture state.

Although posture state module 86 is described as containing the 3-axis accelerometer, posture state module 86 may contain multiple single-axis accelerometers, dual-axis accelerometers, 3-axis accelerometers, or some combination thereof. In some examples, an accelerometer or other sensor may be located within or on IMD 14, on one of leads 16 (e.g., at the distal tip or at an intermediate position), an additional sensor lead positioned somewhere within patient 12, within an independent implantable sensor, or even worn on patient 12. For example, one or more microsensors may be implanted within patient 12 to communicate posture state information wirelessly to IMD 14. In this manner, the patient 12 posture state may be determined from multiple posture state sensors placed at various locations on or within the body of patient 12.

In other examples, posture state module 86 may additionally or alternatively be configured to sense one or more physiological parameters of patient 12. For example, physiological parameters may include heart rate, electromyography (EMG), an electroencephalogram (EEG), an electrocardiogram (ECG), temperature, respiration rate, or pH. These physiological parameters may be used by processor 80, in some embodiments, to confirm or reject changes in sensed posture state that may result from vibration, patient travel (e.g., in an aircraft, car or train), or some other false positive of posture state.

In some examples, processor 80 processes the analog output of the posture state sensor in posture state module 86 to determine activity and/or posture data. For example, where the posture state sensor comprises an accelerometer, processor 80 or a processor of posture state module 86 may process the raw signals provided by the posture state sensor to determine activity counts. In some examples, processor 80 may process the signals provided by the posture state sensor to determine velocity of motion information along each axis.

In one example, each of the x, y, and z signals provided by the posture state sensor has both a DC component and an AC component. The DC components describes the gravitational force exerted upon the sensor and can thereby be used to determine orientation of the sensor within the gravitational field of the earth. Assuming the orientation of the sensor is relatively fixed with respect to the patient, the DC components of the x, y and z signals may be utilized to determine the patient's orientation within the gravitational field, and hence to determine the posture of the patient.

The AC component of the x, y and z signals yields information about patient motion. In particular, the AC component of a signal may be used to derive a value for an activity describing the patient's motion, or activity. This activity may involve a level, direction of motion, or acceleration of the patient.

One method for determining the activity is an activity count. An activity count may be used to indicate the activity or activity level of patient 12. For example, a signal processor may sum the magnitudes of the AC portion of an accelerometer signal for N consecutive samples. For instance, assuming sampling occurs as 25 Hz, N may be set to 25, so that count logic provides the sum of the samples that are obtained in one second. This sum may be referred to as an "activity count." The number "N" of consecutive samples may be selected by the processor based on the current posture state, if desired. The activity count may be the activity portion of the activity parameter value that is added to the posture portion. The resulting activity parameter value may then incorporate both activity and posture to generate an accurate indication of the motion of patient 12.

As another example, the activity parameter value may be defined describing direction of motion. This activity parameter value may be associated with a vector and an associated tolerance, which may be a distance from the vector. Another example of an activity parameter value relates to acceleration. The value quantifying a level of change of motion over time in a particular direction may be associated with this parameter referenced in the activity parameter value.

Processor 80 may monitor the posture state of patient 12 and associate any therapy adjustments that patient 12 makes to the posture state currently occupied by patient 12. However, processor 80 may also employ techniques that allow a therapy adjustment to be associated with a later posture state in cases when patient 12 makes a therapy adjustment in anticipation of changing the posture state. Patient 12 may desire to make this preemptory adjustment to avoid being over-stimulated or under-stimulated when the patient assumes the new posture state.

Processor 80 may employ multiple timers that monitor therapy adjustments and when a new posture state occurs, as a result of a posture state transition. Processor 80 may use a posture search timer having a search period, where the search timer begins upon the detection of the therapy adjustment and expires when the search period lapses. The posture search timer allows a certain amount of time, or the search period, for patient 12 to finally engage in the intended posture state. In addition, processor 80 uses a posture stability timer, where the posture stability timer begins upon the sensing of a different posture state and requires a certain amount of time, the stability period, to elapse while patient 12 is in the same posture state before the posture state can be considered the final posture state. A therapy adjustment is only associated with a posture state when the final posture state is started, i.e., the stability timer is started, prior to the expiration of the search period and the final posture state lasts at least as long as the stability period. Any other therapy adjustments are either associated with the initial posture state patient 12 was engaged in when the therapy was adjusted or not associated with any posture state, depending upon the instructions stored in memory 82.

Processor 80 may record numerous therapy factors including but not limited to, therapy adjustments, therapy parameters, including separate parameters and adjustments for each slot, physiological conditions of a patient, electrode impedances, patient posture and activity, lying transitions. These and other therapy factors may then be transferred to a programmer for presentation to a user.

Although external programmer 20 may perform any processing on the therapy adjustment information, such as the association of therapy adjustments to posture states, processor 80 of IMD 14 may be configured to analyze the information and generate desired information. For example, processor 80 may generate nominal therapy parameters or suggested therapy parameters based upon the therapy adjustment information stored in memory 82. In this manner, IMD 14 may transmit the nominal or suggested therapy parameters directly to external programmer 20 for presentation to the user. Any other shared processing between IMD 14 and external programmer 20 is also contemplated.

Wireless telemetry in IMD 14 with external programmer 20, e.g., patient programmer 30 (FIG. 2) or clinician programmer 60 (FIG. 3), or another device may be accomplished by radio frequency (RF) communication or proximal inductive interaction of IMD 14 with external programmer 20. Telemetry circuit 88 may send information to and receive information from external programmer 20 on a continuous basis, at periodic intervals, at non-periodic intervals, or upon request from the stimulator or programmer. To support RF communication, telemetry circuit 88 may include appropriate electronic components, such as amplifiers, filters, mixers, encoders, decoders, and the like.

Power source 90 delivers operating power to the components of IMD 14. Power source 90 may include a small rechargeable or non-rechargeable battery and a power generation circuit to produce the operating power. Recharging may be accomplished through proximal inductive interaction between an external charger and an inductive charging coil within IMD 14. In some embodiments, power requirements may be small enough to allow IMD 14 to utilize patient motion and implement a kinetic energy-scavenging device to trickle charge a rechargeable battery. In other embodiments, traditional batteries may be used for a limited period of time. As a further alternative, an external inductive power supply could transcutaneously power IMD 14 when needed or desired.

Figure 5:
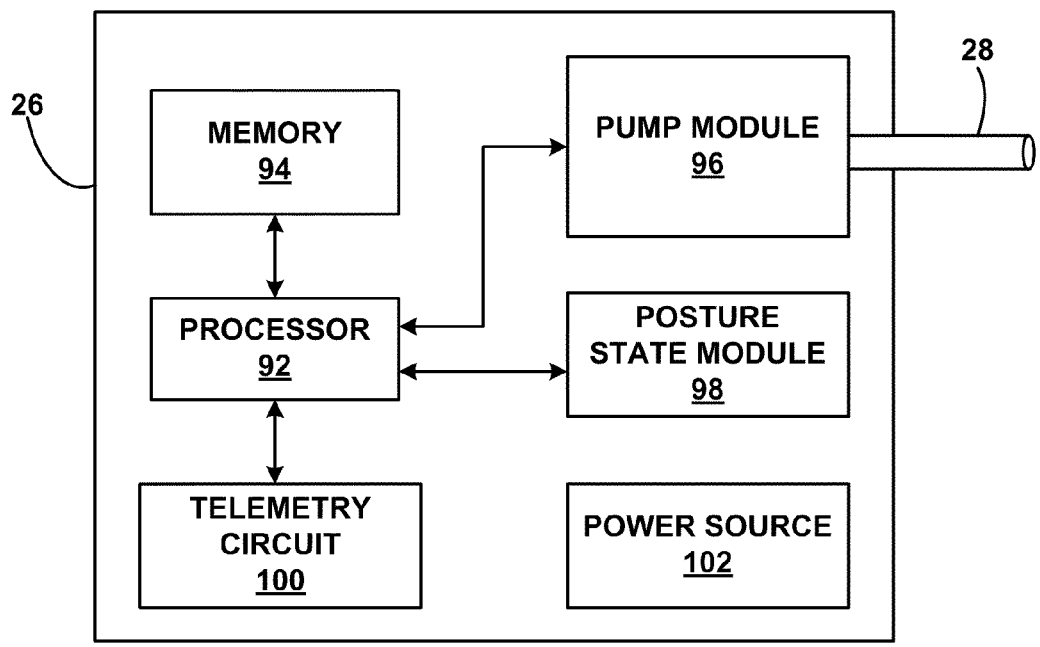
FIG. 5 is a functional block diagram illustrating various components of an implantable drug pump.

FIG. 5 is a functional block diagram illustrating various components of an IMD 26 that is a drug pump. IMD 26 is a drug pump that operates substantially similar to IMD 14 of FIG. 4. IMD 26 includes processor 92, memory 94, pump module 96, posture state module 98, telemetry circuit 100, and power source 102. Instead of stimulation generator 84 of IMD 14, IMD 26 includes pump module 96 for delivering drugs or some other therapeutic agent via catheter 28. Pump module 96 may include a reservoir to hold the drug and a pump mechanism to force drug out of catheter 28 and into patient 12.

Processor 92 may control pump module 96 according to therapy instructions stored within memory 94. For example, memory 94 may contain the programs or groups of programs that define the drug delivery therapy for patient 12. A program may indicate the bolus size or flow rate of the drug, and processor 92 may accordingly deliver therapy. Processor 92 may also use posture state information from posture state module 98 to adjust drug delivery therapy when patient 12 changes posture states, e.g., adjusts his or her posture. In alternative embodiments, system 10 may be employed by an IMD that delivers therapy via both electrical stimulation therapy and drug delivery therapy as a combination of IMD 14 and IMD 26.

Processor 92 may record numerous therapy factors including but not limited to, therapy adjustments, therapy parameters, including separate parameters and adjustments for each slot, physiological conditions of a patient, electrode impedances, patient posture and activity, lying transitions. These and other therapy factors may then be transferred to a programmer for presentation to a user.

Figure 6:
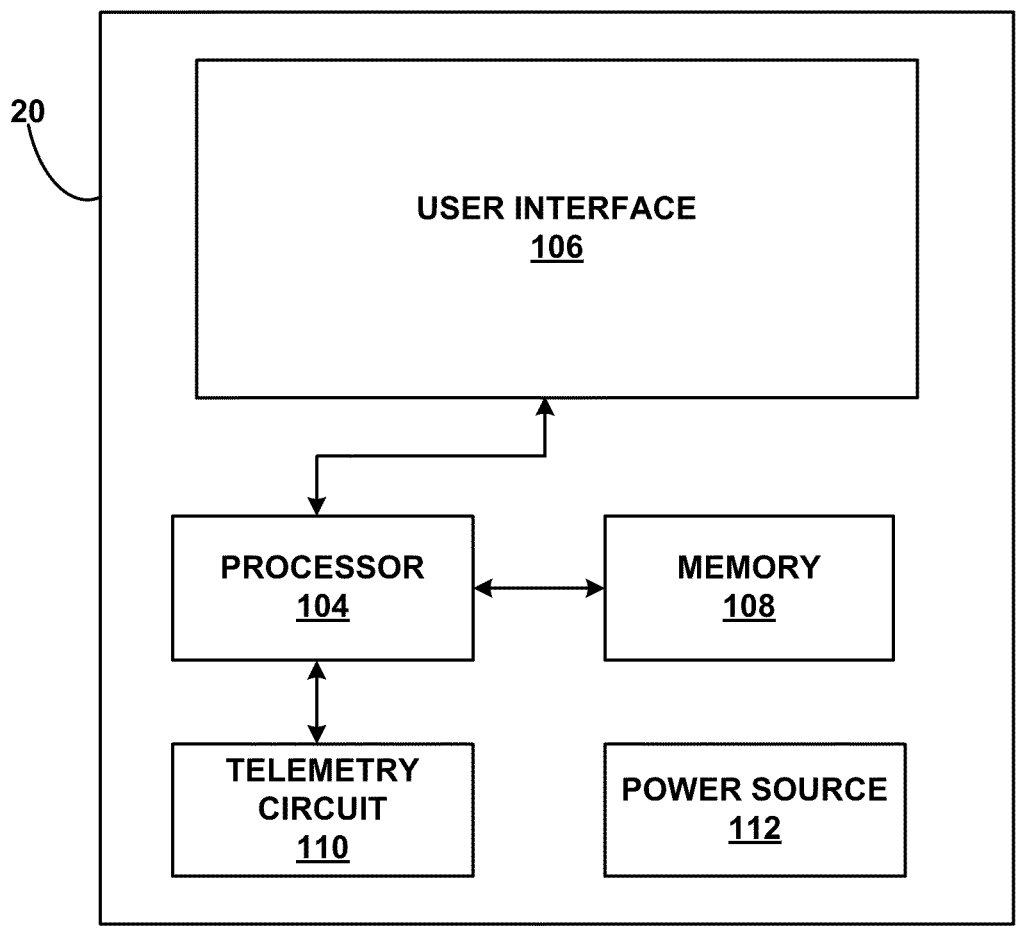
FIG. 6 is a functional block diagram illustrating various components of an external programmer for an IMD.

FIG. 6 is a functional block diagram illustrating various components of an external programmer 20 for IMDs 14 or 26. As shown in FIG. 6, external programmer 20 includes processor 104, memory 108, telemetry circuit 110, user interface 106, and power source 112. External programmer 20 may be embodied as patient programmer 30 or clinician programmer 60. A clinician or patient 12 interacts with user interface 106 in order to manually change the stimulation parameters of a program, change programs within a group, turn posture responsive stimulation ON or OFF, view therapy information, view posture state information, or otherwise communicate with IMDs 14 or 26.

User interface 106 may include a screen and one or more input buttons, as in the example of patient programmer 30, that allow external programmer 20 to receive input from a user. Alternatively, user interface 106 may additionally or only utilize a touch screen display, as in the example of clinician programmer 60. The screen may be a liquid crystal display (LCD), dot matrix display, organic light-emitting diode (OLED) display, touch screen, or any other device capable of delivering and/or accepting information. For visible posture state indications, a display screen may suffice. For audible and/or tactile posture state indications, programmer 20 may further include one or more audio speakers, voice synthesizer chips, piezoelectric buzzers, or the like.

Input buttons for user interface 106 may include a touch pad, increase and decrease buttons, emergency shut off button, and other buttons needed to control the stimulation therapy, as described above with regard to patient programmer 30. Processor 104 controls user interface 106, retrieves data from memory 108 and stores data within memory 108. Processor 104 also controls the transmission of data through telemetry circuit 110 to IMDs 14 or 26. Memory 108 includes operation instructions for processor 104 and data related to therapy for patient 12.

User interface 106 is configured to present therapy adjustment information to the user for monitoring adjustments made by patient 12 and allowing single input and guided programming options for the user. After IMD 14 has associated therapy adjustments to posture states, user interface 106 of external programmer 20 may present the associations to the user as a range of therapy adjustments, maximum and minimum values of the adjusted parameters, last adjustments made, number of adjustments made for each program and posture state, or any other details of the associations. The number of patient therapy adjustments may be recorded based on the cumulative number of adjustments made by the patient 12 over the course of a therapy session when the patient may occupy each of the posture states multiple times. In particular, the number of adjustments may be a cumulative number of adjustments over multiple instances of the sensed posture state, i.e., multiple times in which the patient occupied the posture state. In addition, user interface 106 may display the therapy adjustment information as graphical bar graphs or charts, numerical spread sheets, or any other manner in which information may be displayed. Further, user interface 106 may present nominal or suggested therapy parameters that the user may accept for all programs by making one confirmation input to user interface 106.

The therapy adjustment information may also be stored within memory 108 periodically during therapy, whenever external programmer 20 communicates within IMD 14, or only when the user desired to use the therapy adjustment information. Memory 108 may include a separate memory for therapy adjustment information as opposed to other posture state information or operational instructions. In addition, if memory 108 does store posture state information from patient 12, memory 108 may use one or more hardware or software security measures to protect the identify of patient 12. For example, memory 108 may have separate physical memories for each patient or the user may be required to enter a password to access each patient's posture state data.

Telemetry circuit 110 allows the transfer of data to and from IMD 14, or IMD 26. Telemetry circuit 110 may communicate automatically with IMD 14 at a scheduled time or when the telemetry circuit detects the proximity of the stimulator. Alternatively, telemetry circuit 110 may communicate with IMD 14 when signaled by a user through user interface 106. To support RF communication, telemetry circuit 110 may include appropriate electronic components, such as amplifiers, filters, mixers, encoders, decoders, and the like. Power source 112 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

In some examples, external programmer 20 may be configured to recharge IMD 14 in addition to programming IMD 14. Alternatively, a recharging device may be capable of communication with IMD 14. Then, the recharging device may be able to transfer programming information, data, or any other information described herein to IMD 14. In this manner, the recharging device may be able to act as an intermediary communication device between external programmer 20 and IMD 14. The techniques described in this disclosure may be communicated between IMD 14 via any type of external device capable of communication with IMD 14.

Figure 7:
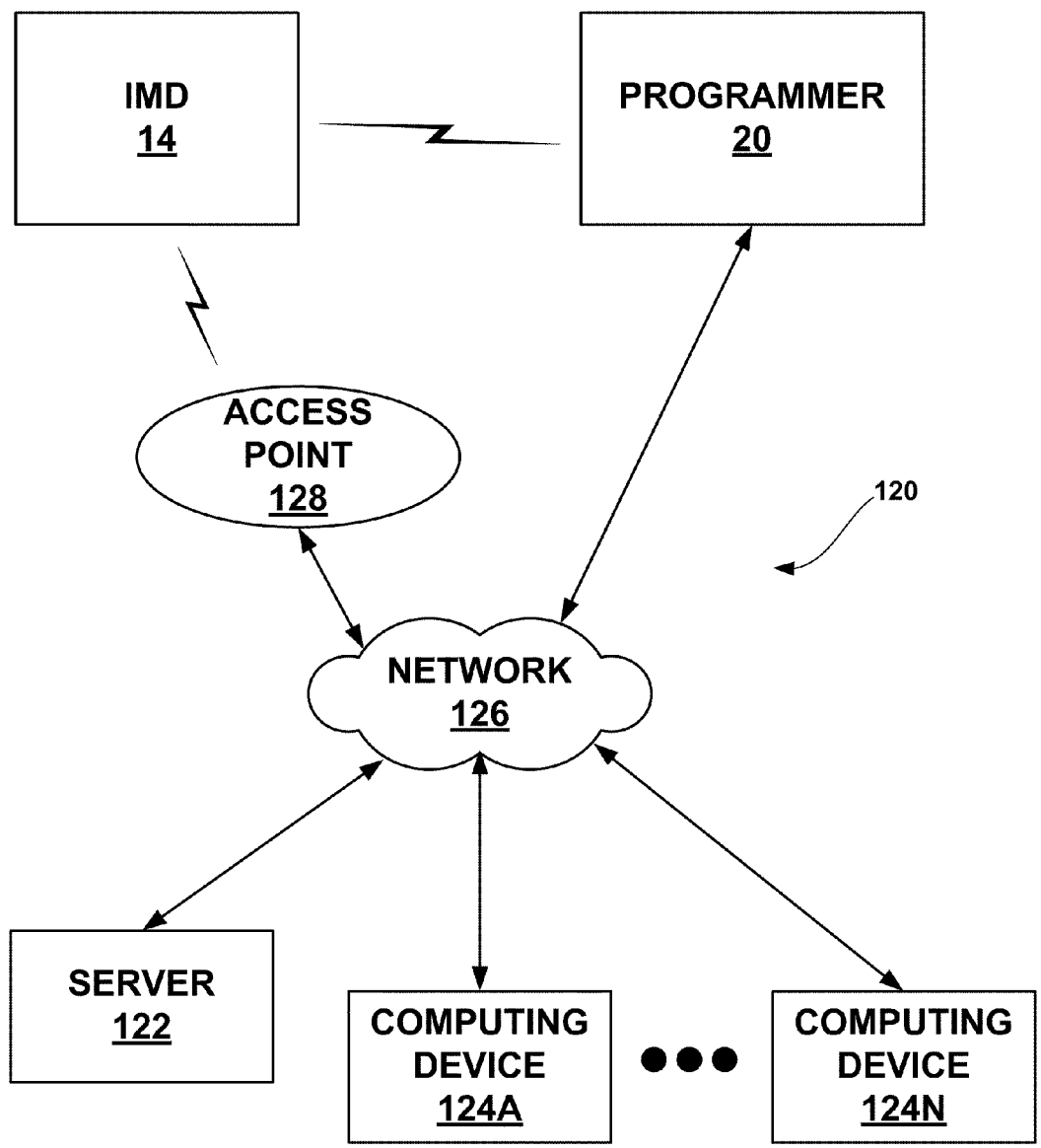
FIG. 7 is a block diagram illustrating an example system that includes an external device, such as a server, and one or more computing devices that are coupled to an IMD and external programmer shown in FIGS. 1A-1C via a network.

FIG. 7 is a block diagram illustrating an example system 120 that includes an external device, such as a server 122, and one or more computing devices 124A-124N, that are coupled to IMD 14 and external programmer 20 shown in FIGS. 1A-1C via a network 126. In this example, IMD 14 may use its telemetry circuit 88 to communicate with external programmer 20 via a first wireless connection, and to communication with an access point 128 via a second wireless connection. In other examples, IMD 26 may also be used in place of IMD 14, and external programmer 20 may be either patient programmer 30 or clinician programmer 60.

In the example of FIG. 7, access point 128, external programmer 20, server 122, and computing devices 124A-124N are interconnected, and able to communicate with each other, through network 126. In some cases, one or more of access point 128, external programmer 20, server 122, and computing devices 124A-124N may be coupled to network 126 through one or more wireless connections. IMD 14, external programmer 20, server 122, and computing devices 124A-124N may each comprise one or more processors, such as one or more microprocessors, digital signal processors (DSPs), application specific integrated circuits (ASICs), field programmable gate arrays (FPGAs), programmable logic circuitry, or the like, that may perform various functions and operations, such as those described in this disclosure.

Access point 128 may comprise a device, such as a home monitoring device, that connects to network 126 via any of a variety of connections, such as telephone dial-up, digital subscriber line (DSL), or cable modem connections. In other embodiments, access point 128 may be coupled to network 126 through different forms of connections, including wired or wireless connections.

During operation, IMD 14 may collect and store various forms of data, including therapy factors associated with delivering electrical stimulation therapy with a neurostimulator to a patient. For example, IMD 14 may collect sensed posture state information during therapy that indicate how patient 12 moves throughout each day. In some cases, IMD 14 may directly analyze the collected data to evaluate the posture state of patient 12, such as what percentage of time patient 12 was in each identified posture. In other cases, however, IMD 14 may send stored data relating to posture state information to external programmer 20 and/or server 122, either wirelessly or via access point 128 and network 126, for remote processing and analysis. For example, IMD 14 may sense, process, trend and evaluate the sensed posture state information. This communication may occur in real time, and network 126 may allow a remote clinician to review the current patient posture state by receiving a presentation of a posture state indication on a remote display, e.g., computing device 124A. Alternatively, processing, trending and evaluation functions may be distributed to other devices such as external programmer 20 or server 122, which are coupled to network 126. In addition, posture state information may be archived by any of such devices, e.g., for later retrieval and analysis by a clinician.

In some cases, IMD 14, external programmer 20 or server 122 may process posture state information or raw data and/or therapy information into a displayable posture state report, which may be displayed via external programmer 20 or one of computing devices 124A-124N. The posture state report may contain trend data for evaluation by a clinician, e.g., by visual inspection of graphic data. In some cases, the posture state report may include the number of activities patient 12 conducted, a percentage of time patient 12 was in each posture state, the average time patient 12 was continuously within a posture state, what group or program was being used to deliver therapy during each activity, the number of adjustments to therapy during each respective posture state, or any other information relevant to patient 12 therapy, based on analysis and evaluation performed automatically by IMD 14, external programmer 20 or server 122. In addition, as discussed in further detail below with respect to FIGS. 13-25, patient posture information may be presented along a common timeline in combination with other therapy factors associated with delivering electrical stimulation therapy to the patient. A clinician or other trained professional may review and/or annotate the posture state report, and possibly identify any problems or issues with the therapy that should be addressed. Further, server 122 may process therapy adjustment information and generate suggested therapy parameters for each program and posture state based upon the therapy adjustment information. If a guided algorithm is computationally intensive, server 122 may be best suited for generating the necessary parameters for therapy.

Using system 120 of FIG. 7, a clinician, physician, technician, or even patient 12, may review therapy adjustment information from IMD 14. The user may remotely monitor the progress and trends of patient 12, limiting the number of times that patient 12 may need to physically visit the clinician. This monitoring may also reduce the time needed to find efficacious therapy parameters by allowing the clinician to more frequently monitor how patient 12 is using patient programmer 30 and how often changes to therapy must be made. Any of the user interfaces described herein with respect to patient programmer 30 or clinician programmer 60 may also be presented via any of computing devices 124A-124N.

In some cases, server 122 may be configured to provide a secure storage site for archival of posture state information that has been collected from IMD 14 and/or external programmer 20. Network 126 may comprise a local area network, wide area network, or global network, such as the Internet. In some cases, external programmer 20 or server 122 may assemble posture state information in web pages or other documents for viewing by trained professionals, such as clinicians, via viewing terminals associated with computing devices 124A-124N. System 120 may be implemented, in some examples, with general network technology and functionality similar to that provided by the Medtronic CareLink® Network developed by Medtronic, Inc., of Minneapolis, Minn.

Although some examples of the disclosure may involve posture state information and data, system 120 may be employed to distribute any information relating to the treatment of patient 12 and the operation of any device associated therewith. For example, system 120 may allow issues with the therapy or device to be immediately reported to the clinician. In addition, system 120 may allow the clinician to remotely intervene in the therapy and reprogram IMD 14, patient programmer 30, or communicate with patient 12. In an additional example, the clinician may utilize system 120 to monitor multiple patients and share data with other clinicians in an effort to coordinate rapid evolution of effective treatment of patients. Further, posture state detection may also be used to provide notifications, such as providing notification via a wireless link to a care giver that a patient has potentially experienced a fall.

Figure 8A:
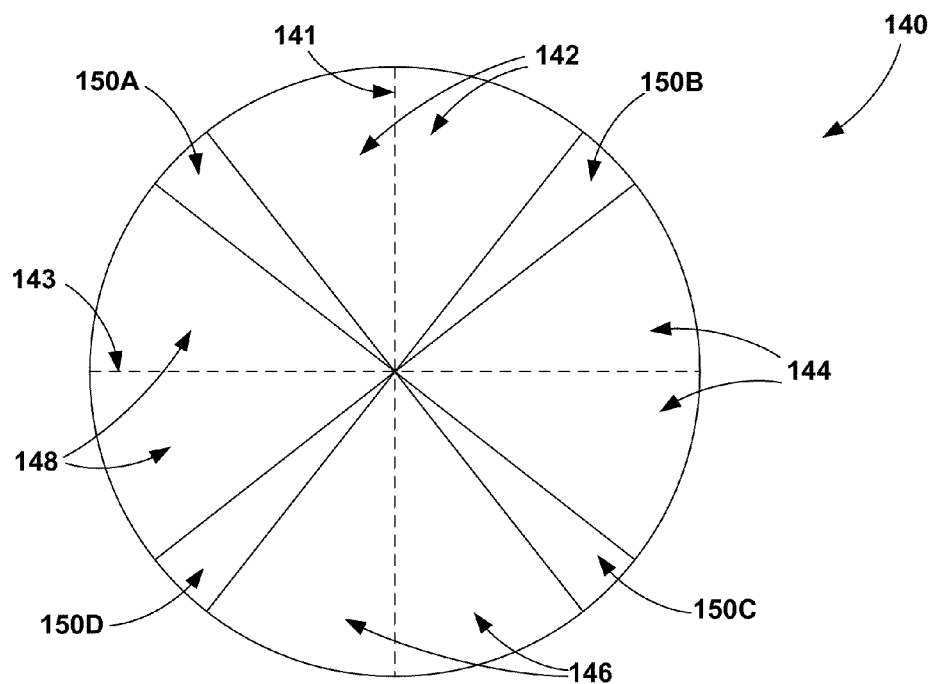
FIGS. 8A-8C are conceptual illustrations of posture cones that may be used to define a posture state of a patient based on signals sensed by a posture state sensor.
Figure 8B:
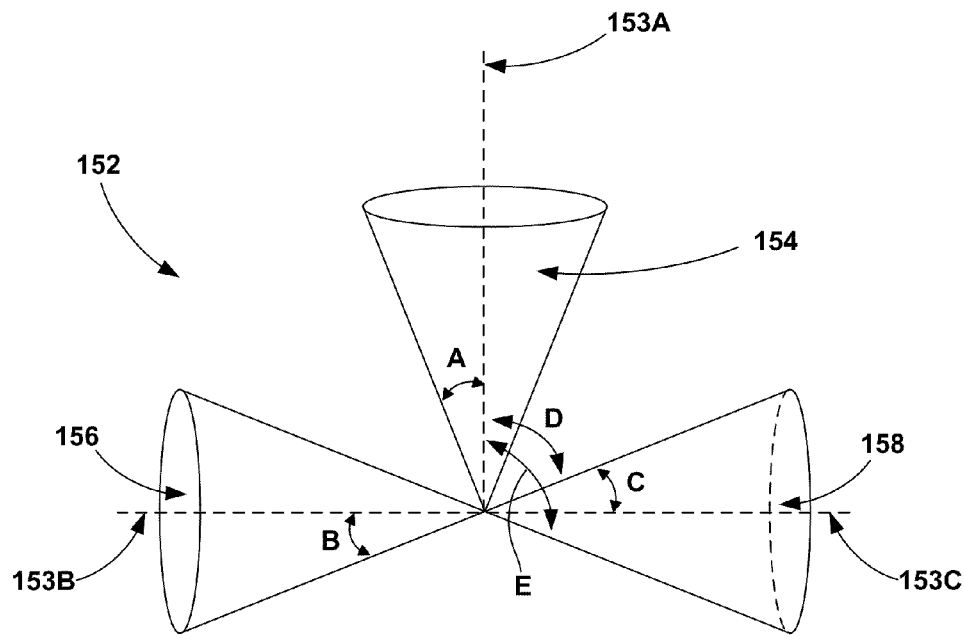
Figure 8C:
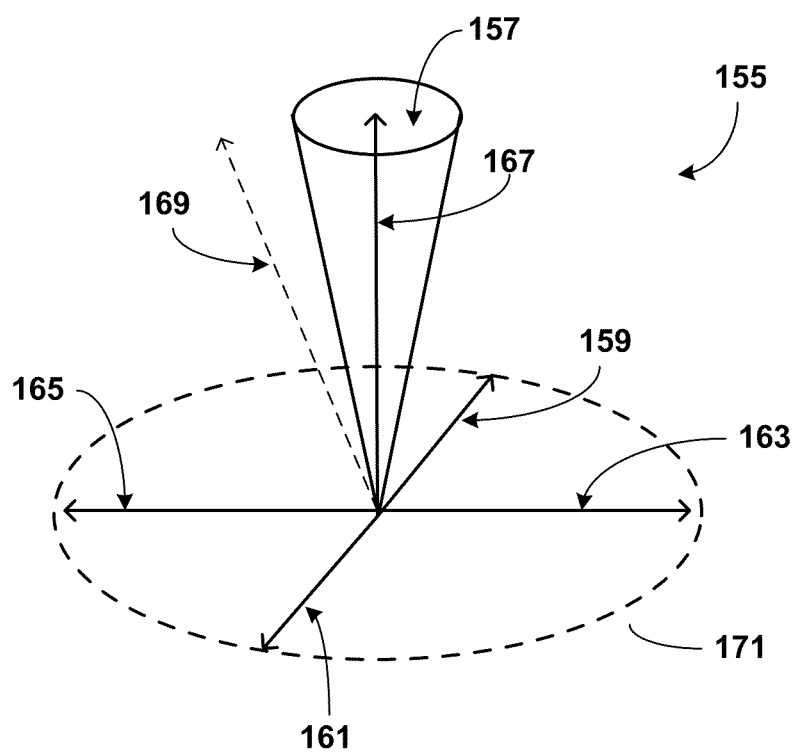

FIGS. 8A-8C are conceptual illustrations of posture state spaces 140, 152, 155 within which posture state reference data may define the posture state of patient 12. Posture state reference data may define certain regions associated with particular posture states of patient 12 within the respective posture state spaces 140, 152, 155. The output of one or more posture state sensors may be analyzed by posture state module 86 with respect to posture state spaces 140, 152, 155 to determine the posture state of patient 12. For example, if the output of one or more posture state sensors is within a particular posture region defined by posture state reference data, posture state module 86 may determine that patient 12 is within the posture state associated with the respective posture state region.

In some cases, one or more posture state regions may be defined as posture state cones. Posture state cones may be used to define a posture state of patient 12 based on the output from a posture state sensor of a posture state according to an example method for posture state detection. A posture state cone may be centered about a posture state reference coordinate vector that corresponds to a particular posture state. In the examples of FIGS. 8A and 8B, the posture state module 86 of IMD 14 or IMD 26 may use a posture state sensor, e.g., a three-axis accelerometer that provides data indicating the posture state of patient 12, to sense posture vectors.

While the sensed data may be indicative of any posture state, postures of patient 12 will generally be used below to illustrate the concept of posture cones. As shown in FIG. 8A, posture state space 140 represents a vertical plane dividing patient 12 from left and right sides, or the sagittal plane. A posture state parameter value from two axes of the posture state sensor may be used to determine the current posture state of patient 12 according to the posture state space 140. The posture state data may include x, y and z coordinate values.

A posture cone may be defined by a reference coordinate vector for a given posture state in combination with a distance or angle defining a range of coordinate vectors within a cone surrounding the posture reference coordinate vector. Alternatively, a posture cone may be defined by a reference coordinate vector and a range of cosine values computed using the reference coordinate vector as an adjacent vector and any of the outermost vectors of the cone as a hypotenuse vector. If a sensed posture state vector is within an applicable angle or distance of the reference coordinate vector, or if the sensed posture state vector and the reference coordinate vector produce a cosine value in a specified cosine range, then posture state vector is determined to reside within the posture cone defined by the reference coordinate vector.

Posture state space 140 is segmented into different posture cones that are indicative of a certain posture state of patient 12. In the example of FIG. 8A, upright cone 142 indicates that patient 12 is sitting or standing upright, lying back cone 148 indicates that patient 12 is lying back down, lying front cone 144 indicates that patient 12 is lying chest down, and inverted cone 146 indicates that patient 12 is in an inverted position. Other cones may be provided, e.g., to indicate that patient 12 is lying on the right side or left side. For example, a lying right posture cone and a lying left posture cone may be positioned outside of the sagittal plane illustrated in FIG. 8A. In particular, the lying right and lying left posture cones may be positioned in a coronal plane substantially perpendicular to the sagittal plane illustrated in FIG. 8A. For ease of illustration, lying right and lying left cones are not shown in FIG. 8A.

Vertical axis 141 and horizontal axis 143 are provided for orientation of posture state space 140, and are shown as orthogonal for purposes of illustration. However, posture cones may have respective posture reference coordinate vectors that are not orthogonal in some cases. For example, individual reference coordinate vectors for cones 142 and 146 may not share the same axis, and reference coordinate vectors for cones 144 and 148 may not share the same axis. Also, reference coordinate vectors for cones 144 and 148 may or may not be orthogonal to reference coordinates vectors for cones 142, 146. Moreover, the reference coordinate vectors need not reside in the same plane. Therefore, although orthogonal axes are shown in FIG. 8A for purposes of illustration, respective posture cones may be defined by individualized reference coordinate vectors for the cones.

IMD 14 may monitor the posture state parameter value of the posture state sensor to produce a sensed coordinate vector and identify the current posture of patient 12 by identifying which cone the sensed coordinated vector of the posture state sensor module 86 resides. For example, if the posture state parameter value corresponds to a sensed coordinate vector that falls within lying front cone 144, IMD 14 determines that patient 12 is lying down on their chest. IMD 14 may store this posture information as a determined posture state or as raw output from the posture state sensor, change therapy according to the posture, or both. Additionally, IMD 14 may communicate the posture information to patient programmer 30 so that the patient programmer can present a posture state indication to patient 12.

In addition, posture state space 140 may include hysteresis zones 150A, 150B, 150C, and 150D (collectively "hysteresis zones 150"). Hysteresis zones 150 are positions within posture state space 140 where no posture cones have been defined. Hysteresis zones 150 may be particularly useful when IMD 14 utilizes the posture state information and posture cones to adjust therapy automatically. If the posture state sensor indicates that patient 12 is in upright cone 142, IMD 14 would not detect that patient 12 has entered a new posture cone until the posture state parameter value indicates a different posture cone. For example, if IMD 14 determines that patient 12 moves to within hysteresis zone 150A from upright cone 142, IMD 14 retains the posture as upright. In this manner, IMD 14 does not change the corresponding therapy until patient 12 fully enters a different posture cone. Hysteresis zones 150 prevent IMD 14 from continually oscillating between different therapies when patient 12's posture state resides near a posture cone boundary.

Each posture cone 142, 144, 146, 148 may be defined by an angle in relation to a reference coordinate vector defined for the respective posture cone. Alternatively, some posture cones may be defined by an angle relative to a reference coordinate vector for another posture cone. For example, lying postures may be defined by an angle with respect to a reference coordinate vector for an upright posture cone. In each case, as described in further detail below, each posture cone may be defined by an angle in relation to a reference coordinate posture vector defined for a particular posture state. The reference coordinate vector may be defined based on posture sensor data generated by a posture state sensor while patient 12 occupies a particular posture state desired to be defined using the reference coordinate vector. For example, a patient may be asked to occupy a posture so that a reference coordinate vector can be sensed for the respective posture. In this manner, vertical axis 141 may be specified according to the patient's actual orientation. Then, a posture cone can be defined using the reference coordinate vector as the center of the cone.

Vertical axis 141 in FIG. 8A may correspond to a reference coordinate vector sensed while the patient was occupying an upright posture state. Similarly, a horizontal axis 143 may correspond to a reference coordinate vector sensed while the patient is occupying a lying posture state. A posture cone may be defined with respect to the reference coordinate vector. Although a single axis is shown extending through the upright and inverted cones 142, 146, and another single axis is shown extending through the lying down and lying up cones 144, 148, individual reference coordinate vectors may be used for respective cones, and the reference coordinate vectors may not share the same axes, depending on differences between the reference coordinate vectors obtained for the posture cones.

Posture cones may be defined by the same angle or different angles, symmetrical to either axis, or asymmetrical to either axis. For example, upright cone 142 may have an angle of eighty degrees, +40 degrees to −40 degrees from the positive vertical axis 141. In some cases, lying cones may be defined relative to the reference coordinate vector of the upright cone 142. For example, lying up cone 148 may have an angle of eighty degrees, −50 degrees to −130 degrees from the positive vertical axis 141. Inverted cone 146 may have an angle of eighty degrees, −140 degrees to +140 degrees from vertical axis 141. In addition, lying down cone 144 may have an angle of eighty degrees, +50 degrees to +130 degrees from the positive vertical axis 141. In other examples, each posture cone may have varying angle definitions, and the angles may change during therapy delivery to achieve the most effective therapy for patient 12.

Alternatively or additionally, instead of an angle, posture cones 144, 146, 148, 148 may be defined by a cosine value or range of cosine values in relation to vertical axis 141, horizontal axis 143, or some other axis, such as, e.g., individual reference coordinate vectors for the respective cones. For example, a posture cone may be defined by a cosine value that defines the minimum cosine value, calculated using a reference coordinate vector and a respective coordinate vector sensed by a posture state sensor at any point in time. In the cosine computation, the value (adjacent/hypotenuse) can be computed using the magnitude of the coordinate reference vector as the adjacent and a vector at the outermost extent of the cone as the hypotenuse to define a range of cosine values consistent with the outer bound of the cone.

For upright cone 142, the cosine range may extend from the maximum cosine value of 1.0, corresponding to a sensed vector that matches the reference coordinate vector of the upright cone, to a minimum cosine value that corresponds to a sensed vector at the outer limit of the upright cone. As another example, for lying cone 144, the cosine range may extend from the maximum cosine value of 1.0, corresponding to a sensed vector that matches the reference coordinate vector of the lying cone, to a minimum cosine value that corresponds to a sensed vector at the outer limit of the lying cone. Alternatively, the lying cone 144 may be defined with reference to the upright cone 142, such that the cosine range may extend between a maximum and minimum values determined relative to the reference coordinate vector for the upright cone.

In other examples, posture state space 140 may include additional posture cones than those shown in FIG. 8A. For example, a reclining cone may be located between upright cone 142 and lying back cone 148 to indicate when patient 12 is reclining back (e.g., in a dorsal direction). In this position, patient 12 may need a different therapy to effectively treat symptoms. Different therapy programs may provide efficacious therapy to patient 12 when patient 12 is in each of an upright posture (e.g., within upright cone 142), lying back posture (e.g., within lying back cone 148), and a reclining back posture. Thus, a posture cone that defines the reclining back posture may be useful for providing efficacious posture-responsive therapy to patient 12. In other examples, posture state space 140 may include fewer posture cones than cones 142, 144, 146, 148 shown in FIG. 8A. For example, inverted cone 146 may be replaced by a larger lying back cone 148 and lying front cone 144.

FIG. 8B illustrates an example posture state space 152 that is a three-dimensional space in which the posture state parameter value from the posture state sensor is placed in relation to the posture cones. Posture state space 152 is substantially similar to posture state space 140 of FIG. 8A. However, the posture state parameter value derived from all three axes of a 3-axis accelerometer may be used to accurately determine the posture state of patient 12. In the example of FIG. 8B, posture state space 152 includes upright cone 154, lying back cone 156, and lying front cone 158. Posture state space 152 also includes hysteresis zones (not shown) similar to those of posture state space 140. In the example of FIG. 8B, the hysteresis zones are the spaces not occupied by a posture cone, e.g., upright cone 154, lying back cone 156, and lying front cone 158.

Posture cones 154, 156 and 158 also are defined by a respective center line 153A, 153B, or 153C, and associated cone angle A, B or C. For example, upright cone 154 is defined by center line 153A that runs through the center of upright cone 154. Center line 153A may correspond to an axis of the posture state sensor or some other calibrated vector. In some embodiments, each center line 153A, 153B, 153C may correspond to a posture reference coordinate vectors defined for the respective postures, e.g., the upright posture. For instance, assuming that patient 12 is standing, the DC portion of the x, y, and z signals detected by the posture state sensor of posture state module 86 define a posture vector that corresponds to center line 153A. The x, y, and z signals may be measured while patient 12 is known to be in a specified position, e.g., standing, and the measured vector may be correlated with the upright posture state. Thereafter, when the DC portions of the posture state sensor signal are within some predetermined cone tolerance or proximity, e.g., as defined by an angle, distance or cosine value, of the posture reference coordinate vector (i.e., center line 153A), it may be determined that patient 12 is in the upright posture. In this manner, a sensed posture coordinate vector may be initially measured based on the output of one or more posture state sensors of posture state module 86, associated with a posture state, such as upright, as a reference coordinate vector, and then later used to detect a patient's posture state.

As previously indicated, it may be desirable to allow some tolerance to be associated with a defined posture state, thereby defining a posture cone or other volume. For instance, in regard to the upright posture state, it may be desirable to determine that a patient who is upright but leaning slightly is still in the same upright posture state. Thus, the definition of a posture state may generally include not only a posture reference coordinate vector (e.g., center line 153A), but also a specified tolerance. One way to specify a tolerance is by providing an angle, such as cone angle A, relative to coordinate reference vector 153A, which results in posture cone 154 as described herein. Cone angle A is the deflection angle, or radius, of upright cone 154. The total angle that each posture cone spans is double the cone angle. The cone angles A, B, and C may be generally between approximately 1 degree and approximately 70 degrees. In other examples, cone angles A, B, and C may be between approximately 10 degrees and 30 degrees. In the example of FIG. 8B, cone angles A, B, and C are approximately 20 degrees. Cone angles A, B, and C may be different, and center lines 153A, 153B, and 153C may not be orthogonal to each other.

In some examples, a tolerance may be specified by a cosine value or range of cosine values. The use of cosine values, in some cases, may provide substantial processing efficiencies. As described above, for example, a minimum cosine value, determined using the reference coordinate vector as adjacent and sensed coordinate vector as hypotenuse, indicates the range of vectors inside the cone. If a sensed coordinate vector, in conjunction with the reference coordinate vector for a posture cone, produces a cosine value that is less than the minimum cosine value for the posture cone, the sensed coordinate vector does not reside within the pertinent posture cone. In this manner, the minimum cosine value may define the outer bound of a range of cosine values within a particular posture cone defined in part by a reference coordinate vector.

While center lines 153A, 153B, 153C of each of the posture cones 154, 156, 158, respectively, are shown in FIG. 8B as being substantially orthogonal to each other, In other examples, center lines 153A, 153B, and 153C may not be orthogonal to each other, and need not even reside within the same plane. Again, the relative orientation of center lines 153A, 153B, 153C may depend on the actual reference coordinate vector output of the posture state sensor of posture state module 86 of IMD 14 when patient 12 occupies the respective postures.

In some cases, all of the posture cones may be individually defined based on actual reference coordinate vectors. Alternatively, in some cases, some posture cones may be defined with reference to one or more reference coordinate vectors for one or more other posture cones. For example, lying reference coordinate vectors could be assumed to be orthogonal to an upright reference coordinate vector. Alternatively, lying reference coordinate vectors could be individually determined based on sensed coordinate vectors when the patient is in respective lying postures. Hence, the actual reference coordinate vectors for different postures may be orthogonal or non-orthogonal with respect to one another, and need not reside within a same plane.

In addition to upright cone 154, lying back cone 156, and lying front cone 158, posture state space 152 may include additional posture cones. For example, a lying right cone may be provided to define a patient posture in which patient 12 is lying on his right side and a lying left cone may be provided to define a patient posture in which patient 12 is lying on his left side. In some cases, the lying right cone and lying left cone may be positioned approximately orthogonal to upright cones 154, in approximately the same plane as lying back cone 156 and lying front cone 158. Moreover, posture state space 152 may include an inverted cone positioned approximately opposite of upright cone 154. Such a cone indicates that the patient's posture is inverted from the upright posture, i.e., upside down.

In some examples, to detect the posture state of a patient, posture state module 86 of IMD 14 may determine a sensed coordinate vector based on the posture sensor data generated by one or more posture state sensors, and then analyze the sensed coordinate vector with respect to posture cones 154, 156, 158 of FIG. 8B. For example, in a case in which a posture cone is defined by a reference coordinate vector and a tolerance angle, e.g., tolerance angle "A," posture state module 86 may determine whether the sensed coordinate vector is within upright posture cone 154 by calculating the angle between the sensed coordinate vector and reference coordinate vector, and then determine whether the angle is less than the tolerance angle "A." If so, posture state module 86 determines that the sensed coordinate vector is within upright posture cone 154 and detects that patient 12 is in the upright posture. If posture state module 86 determines that sensed coordinate vector is not within upright posture cone 154, posture state module 86 detects that patient 12 is not in the upright posture.

Posture state module 86 may analyze the sensed coordinate vector in posture state space 152 with respect to each individual defined posture cone, such as posture cones 156 and 158, in such a manner to determine the posture state of patient 12. For example, posture state module 86 may determine the angle between the sensed coordinate vector and reference coordinate vector of individual posture cones defined for the posture state, and compare the determined angle to the tolerance angle defined for the respective posture cone. In this manner, a sensed coordinate vector may be evaluated against each posture cone until a match is detected, i.e., until the sensed coordinate vector is found to reside in one of the posture cones. Hence, a cone-by-cone analysis is one option for posture detection.

In other examples, different posture detection analysis techniques may be applied. For example, instead of testing a sensed coordinate vector against posture cones on a cone-by-cone basis, a phased approach may be applied where the sensed coordinate vector is classified as either upright or not upright. In this case, if the sensed coordinate vector is not in the upright cone, posture state module 86 may determine whether the sensed coordinate vector is in a lying posture, either by testing the sensed coordinate vector against individual lying posture cones or testing the sensed coordinate vector against a generalized lying posture volume, such as a donut- or toroid-like volume that includes all of the lying postures, and may be defined using an angle or cosine range relative to the upright vector, or relative to a modified or virtual upright vector as will be described. In some cases, if lying postures are defined by cones, the lying volume could be defined as a logical OR of the donut- or toroid-like volume and the volumes of the lying posture cones. If the cones are larger such that some portions extend beyond the lying volume, then those portions can be added to the lying volume using the logical OR-like operation.

If the sensed coordinate vector resides within the donut- or toroid-like lying volume, then the sensed coordinate vector may be tested against each of a plurality of lying posture cones in the lying volume. Alternatively, the posture detection technique may not use lying cones. Instead, a posture detection technique may rely on a proximity test between the sensed coordinate vector and each of the reference coordinate vectors for the respective lying postures. The proximity test may rely on angle, cosine value or distance to determine which of the lying posture reference coordinate vectors is closest to the sensed coordinate vector. For example, the reference coordinate vector that produces the largest cosine value with the sensed coordinate vector as hypotenuse and the reference coordinate vector as adjacent is the closest reference coordinate vector. In this case, the lying posture associated with the reference coordinate vector producing the largest cosine value is the detected posture. Hence, there are a variety of ways to detect posture, such as using posture cones, using an upright posture cone with lying volume and lying posture cone test, or using an upright posture cone with lying volume and lying vector proximity test.

As a further illustration of an example posture detection technique, posture state module 86 may first determine whether patient 12 is generally in a lying posture state or upright posture state by analyzing the sensed coordinate vector in posture state space 152 with respect to an axis 153A for the upright posture state. Axis 153A may correspond to the upright reference coordinate vector. For example, angle "A" may be used to define upright posture cone 154, as described above, and angles "D" and "E" may be used to define the vector space in which patient 12 may be generally considered to be in the lying posture state, regardless of the particular posture state cone, e.g., lying front cone 158, lying back cone 156, lying right cone (not shown), or lying left cone (not shown), in which the sensed coordinate vector falls.

If it is determined that a sensed coordinate vector is not within an angle A of the axis 153A, then it may be determined that the patient is not in the upright posture indicated by the upright posture cone. In this case, it may next be determined whether a sensed coordinated vector is generally in a lying posture space volume, which may be considered somewhat donut- or toroid-like, and may be defined relative to the upright reference coordinate vector 153A. As shown, angles "D" and "E" define the minimum and maximum angle values, respectively, that a sensed vector may form with respect to axis 153A of patient 12 for a determination to be made that the patient is generally in the lying posture state. Again, cosine values may be used instead of angles to determine the positions of sensed coordinate vectors relative to posture cones or other posture volumes, or relative to reference coordinate vectors.

As illustrated, angles "D" and "E" may be defined with respect to vertical axis 153A (which may correspond to an upright reference coordinate vector), which is the reference coordinate vector for the upright posture cone, rather than with respect to a reference coordinate vector of a lying posture state cone. If a sensed vector is within the angular range of D to E, relative to axis 153A, then it can be determined by posture state module 86 that the patient is generally in a lying posture. Alternatively, in some examples, an angle C could be defined according to a generally horizontal axis 153C (which may correspond to one of the lying reference coordinate vectors). In this case, if a sensed vector is within angle C of axis 153C, it can be determined by posture state module 86 that the patient is in a lying posture. In each case, the region generally defining the lying posture state may be referred to as a posture donut or posture toroid, rather than a posture cone. The posture donut may generally encompass a range of vectors that are considered to be representative of various lying down postures.

As an alternative, posture state module 86 may rely on cosine values or a range of cosine values to define the posture donut or toroid with respect to axis 153A. When the sensed vector falls within the vector space defined by axis 153A and angles "D" and "E", or produces a cosine value with the reference coordinate vector 153A in a prescribed range, posture state module 86 may determine that patient 12 is generally in a lying posture state. For example, if the sensed vector and reference coordinate vector 153 produce a cosine value in a first range, the posture is upright. If the cosine value is in a second range, the posture is lying. If the cosine value is outside of the first and second ranges, the posture may be indeterminate. The first range may correspond to the range of cosine values that would be produced by vectors in posture cone 154 defined by angle A, and the second range may be correspond to cosine values that would be produced by vectors in the posture donut defined by angles D and E.

When the sensed vector falls within the vector space defined by axis 153A and angles "D" and "E", as indicated by angle or cosine value, posture state module 86 may then determine the particular lying posture state occupied by patient 12, e.g., lying front, lying back, lying right, or lying left. To determine the particular lying posture state occupied by patient 12, posture state module 86 may analyze the sensed vector with respect to reference coordinate vectors for individual lying posture state cones, e.g., lying front cone 156, lying back cone 158, lying right cone (not shown), and lying left cone (not shown), using one more techniques previously described, such as angle or cosine techniques. For example, posture state module 86 may determine whether the sensed coordinated vector resides within one of the lying posture state cones and, if so, select the posture state corresponding to that cone as the detected posture state.

FIG. 8C illustrates an example posture state space 155 that is a three-dimensional space substantially similar to posture state space 152 of FIG. 8B. Posture state space 155 includes upright posture cone 157 defined by reference coordinate vector 167. The tolerance that defines upright posture cone 157 with respect to reference coordinate vector 167 may include a tolerance angle or cosine value, as described above. In contrast to determining whether a sensed coordinate vector resides in a lying cone, FIG. 8C illustrates a method for detecting a lying posture based on proximity of a sensed coordinate vector to one of the reference coordinate vectors for the lying postures.

As shown in FIG. 8C, posture state space 155 includes four reference coordinate vectors 159, 161, 163, 165, which are associated with lying left, lying right, lying front, and lying back posture states, respectively. Posture state module 86 may have defined each of the four reference coordinate vectors 159, 161, 163, 165 based on the output of one or more posture sensors while patient 12 occupied each of the corresponding posture states. Unlike lying front and lying back posture cones 158, 156 in the example of FIG. 8B, the posture state reference data for the four defined posture states corresponding to reference vectors 159, 161, 163, 165 need not include angles defined relative to the respective reference vector in a manner that defines a posture cone. Rather, as will be described below, the respective posture state reference vectors may be analyzed with respect to one another in terms of cosine values to determine which particular reference coordinate vector is nearest in proximity to a sensed coordinate vector.

In some examples, to determine the posture state of patient 12, posture state module 85 may determine whether a sensed coordinate vector is within upright posture cone 157 by analyzing the sensed coordinate vector in view of the tolerance angle or cosine value(s) defined with respect to upright posture reference coordinate vector 167, or whether the sensed vector is within a posture donut or toroid defined by a range of angles (as in FIG. 8B) or cosine values with respect to upright posture reference coordinate vector 167, in which case posture state module 86 may determine that patient 12 is in a general lying posture state.

If posture state module 86 determines that patient 12 is occupying a general lying posture state, posture state module 86 may then calculate the cosine value of the sensed coordinate vector with respect to each lying reference coordinate vectors 159, 161, 163, 165. In such a case, posture state module 86 determines the particular lying posture state of patient 12, i.e., lying left, lying right, lying front, lying back, based on which cosine value is the greatest of the four cosine values. For example, if the cosine value calculated with the sensed vector as the hypotenuse and the lying front reference vector 163 as the adjacent vector is the largest value of the four cosine values, the sensed vector may be considered closest in proximity to lying front reference vector out of the four total reference vectors 159, 161, 163, 165. Accordingly, posture state module 85 may determine that patient 12 is occupying a lying front posture state.

In some examples, posture state module 86 may determine whether patient 12 is generally in a lying posture state based on the relationship of a sensed vector to upright reference vector 167. For example, as described above, a lying posture donut or toroid may be defined with respect to upright posture reference vector 167, e.g., using angles D and E as in FIG. 8B. Such a technique may be appropriate when lying posture reference vectors 159, 161, 163, 165 define a common plane substantially orthogonal to upright posture reference vector 167. However, the lying posture reference vectors 159, 161, 163, 165 may not in fact be orthogonal to the upright reference coordinate vector 167. Also, the lying posture reference vectors 159, 161, 163, 165 may not reside in the same plane.

To account for non-orthogonal reference vectors, in other examples, a lying posture donut or toroid may be defined with respect to a modified or virtual upright reference vector 169 rather than that actual upright posture reference vector 167. Again, such a technique may be used in situations in which the lying reference vectors 159, 161, 163, 165 are not in a common plane, or the common plane of reference vector 159, 161, 163, 165 is not substantially orthogonal to upright reference vector 167. However, use of the example technique is not limited to such situations.

To define virtual upright reference vector 169, posture state module 86 may compute the cross-products of various combinations of lying reference vectors 159, 161, 163, 165 and average the cross product values. In the example of FIG. 8C, posture state module 86 may compute four cross products and average the four cross product vectors to yield the virtual upright vector. The cross product operations that may be performed are: lying left vector 159×lying back vector 165, lying back vector 165×lying right vector 161, lying right vector 161×lying front vector 163, and lying front vector 163×lying left vector 159. Each cross product yields a vector that is orthogonal to the two lying reference vectors that were crossed. Averaging each of the cross product vectors yields a virtual upright reference vector that is orthogonal to lying plane 171 approximately formed by lying reference vectors 159, 161, 163, 165.

Using virtual upright reference vector 169, posture state module 86 may define a lying posture donut or toroid in a manner similar to that described with respect to upright reference vector 167, but instead with respect to virtual upright reference vector 169. In particular, when posture state module 86 determines that the patient is not in the upright posture, the posture state module determines whether the patient is in a lying posture based on an angle or cosine value with respect to the virtual upright reference vector 169.

Posture state module 86 may still determine whether patient 12 is in an upright posture state using upright posture cone 157. If posture state module 86 determines that patient 12 is occupying a general lying posture state based on the analysis of the sensed coordinate vector with respect to virtual upright reference vector 169, posture state module 86 may then calculate the cosine value of the sensed coordinate vector (as hypotenuse) with respect to each lying reference coordinate vectors 159, 161, 163, 165 (as adjacent).

In such a case, posture state module 86 determines the particular lying posture state of patient 12, i.e., lying left, lying right, lying front, lying back, based on which cosine value is the greatest of the four cosine values. For example, if the cosine value calculated with the lying front reference vector 163 is the largest value of the four cosine values, the sensed vector may be considered closest in proximity to lying front reference vector out of the four total reference vectors 159, 161, 163, 165. Accordingly, posture state module 85 may determine that patient 12 is occupying a lying front posture state.

Additionally, posture state definitions are not limited to posture cones. For example, a definition of a posture state may involve a posture vector and a tolerance, such as a maximum distance from the posture vector. So long as a detected posture vector is within this maximum distance from the posture vector that is included in the definition of the posture state, patient 12 may be classified as being in that posture state. This alternative method may allow posture states to be detected without calculating angles, as is exemplified above in the discussion related to posture cones.

Further to the foregoing, posture states may be defined that are specific to a particular patient's activities and/or profession. For instance, a bank teller may spend a significant portion of his working day leaning forward at a particular angle. A patient-specific "Leaning Forward" posture state including this angle may be defined. The cone angle or other tolerance value selected for this posture state may be specific to the particular posture state definition for this patient. In this manner, the defined posture states may be tailored to a specific user, and need not be "hard-coded" in the IMD.

In some examples, individual posture states may be linked together, thereby tying posture states to a common set of posture reference data and a common set of therapy parameter values. This may, in effect, merge multiple posture cones for purposes of posture state-based selection of therapy parameter values. For example, all lying posture state cones (back, front, left, right) could be treated as one cone or a donut/toroid, e.g., using a technique the same as or similar to that described with respect to FIGS. 8B and 8C to define a donut, toroid or other volume. One program group or common set of therapy parameter values may apply to all posture states in the same merged cone, according to the linking status of the posture states, as directed via external programmer 20.

Merging posture cones or otherwise linking a plurality of posture states together may be useful for examples in which a common set of therapy parameter values provides efficacious therapy to patient 12 for the plurality of posture states. In such an example, linking a plurality of posture states together may help decrease the power consumption required to provide posture-responsive therapy to patient 12 because the computation required to track patient posture states and provide responsive therapy adjustments may be minimized when a plurality of posture states are linked together.

Linking of posture states also may permit a therapy parameter value adjustment in one posture state to be associated with multiple posture states at the same time. For example, the same amplitude level for one or more programs may be applied to all of the posture states in a linked set of posture states. Alternatively, the lying down posture states may all reside within a "donut" or toroid that would be used instead of separate comes 156 and 158, for example. The toroid may be divided into sectional segments that each correspond to different posture states, such as lying (back), lying (front), lying (right), lying (left) instead of individual cones. In this case, different posture reference data and therapy parameter values may be assigned to the different sectional segments of the toroid.

Figure 9:
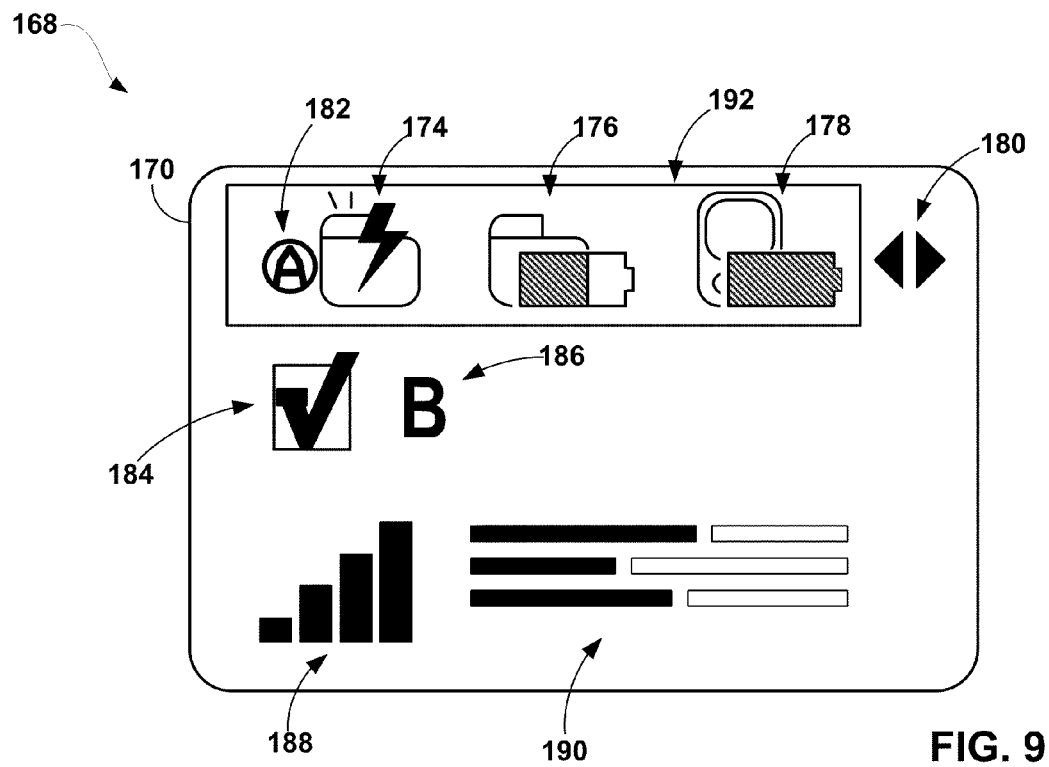
FIG. 9 is a conceptual diagram illustrating an example user interface of a patient programmer for delivering therapy information to the patient.

FIG. 9 is a conceptual diagram illustrating an example user interface 168 of a patient programmer 30 for delivering therapy information to patient 12. In other examples, a user interface similar to user interface 168 may also be shown on clinician programmer 60. In the example of FIG. 9, display 36 of patient programmer 30 provides user interface 168 to the user, such as patient 12, via screen 170. Screen 170 includes stimulation icon 174, IMD battery icon 176, programmer battery icon 178, navigation arrows 180, automatic posture response icon 182, group selection icon 184, group identifier 186, program identifier 188, amplitude graph 190, and selection box 192. User interface 168 provides information to patient 12 regarding group, program, amplitude, and automatic posture response status. User interface 168 may be configurable, such that more or less information may be provided to patient 12, as desired by the clinician or patient 12.

Selection box 192 allows patient 12 to navigate to other screens, groups, or programs using navigation arrows 180 to manage the therapy. In the example, of screen 170, selection box 192 is positioned so that patient 12 may use arrows 44 and 48 to move to the automatic posture response screen, the volume screen, the contrast or illumination screen, the time screen, and the measurement unit screen of patient programmer 30. In these screens, patient 12 may be able to control the use of the automatic posture response feature and adjust the patient programmer 30 features. Patient 12 may only adjust the features surrounded by selection box 192.

Group identifier 186 indicates one of possibly several groups of programs that can be selected for delivery to patient 12. Group selection icon 184 indicates whether the displayed group, e.g., group B in FIG. 9, is actually selected for delivery to patient 12. If a presently displayed group is selected, group selection icon 184 includes a box with a checkmark. If a presently displayed group is not selected, group selection icon 184 includes a box without a checkmark. To navigate through the program groups, a user may use control pad 40 to move selection box 192 to select the group identifier 186 and then use control pad 40 to scroll through the various groups, e.g., A, B, C, and so forth. IMD 14 may be programmed to support a small number of groups or a large number of groups, where each group contains a small number of programs or a large number of programs that are delivered simultaneously, in sequence, or on a time-interleaved basis.

For each group, group selection icon 184 indicates the appropriate status. For a given group, program identifier 188 indicates one of the programs associated with the group. In the example of FIG. 9, no program number is indicated in program identifier 188 because all of the programs' amplitudes are shown in each bar of amplitude graph 190. Solid portions of the bars indicate the relative amplitude IMD 14 currently is using to deliver stimulation therapy to patient 12, while open portions of the bars indicate the remaining amplitude available to each program. In some embodiments, numerical values of each program's amplitude may be shown in addition to or in place of amplitude graph 190. In other embodiments of user interface 168 specific to drug delivery using IMD 26, amplitude graph 190 may show the flow rate of drugs or frequency of bolus delivery to patient 12. This information may be show in numerical format as well. Patient 12 may encompass group selection icon 184 with selection box 192 to scroll between the different programs of the selected group.

Automatic posture response icon 182 indicates that IMD 14 is generally activated to automatically change therapy to patient 12 based upon the posture state detected by posture state module 86. In particular, automatic posture responsive therapy may involve adjusting one or more therapy parameter values, selecting different programs or selecting different program groups based on the detected posture state of the patient. However, automatic posture response icon 182 is not present next to group identifier 186. Therefore, group "B" does not have automatic posture responsive therapy activated for any of the programs within group "B."

Some groups or individual programs in groups may support automatic posture responsive therapy. For example, automatic adjustment of one or more therapy parameters in response to posture state indication may be selectively activated or deactivated based on settings entered by a clinician, or possibly patient 12. Hence, some programs or groups may be configured for use with posture responsive therapy while other programs or groups may not be configured for use with posture responsive therapy. In some cases, if posture responsive therapy supported by the automatic posture response feature is desired, patient 12 may need to switch therapy to a different group that has automatic posture responsive therapy activated for IMD 14 to adjust therapy according to the patient 12 posture state.

Figure 10:
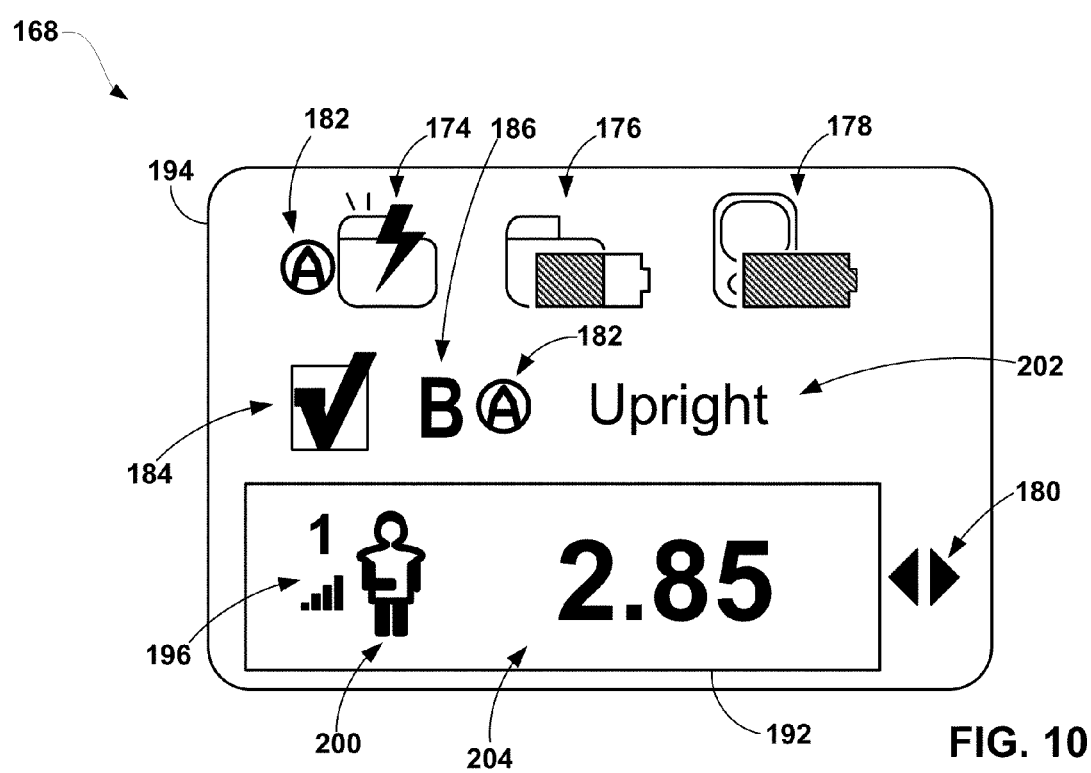
FIG. 10 is a conceptual diagram illustrating an example user interface of a patient programmer for delivering therapy information that includes posture information to the patient.

FIG. 10 is a conceptual diagram illustrating an example user interface 168 of a patient programmer 30 for delivering therapy information that includes posture information to the patient. In other examples, user interface 168 may also be shown on clinician programmer 60. In the example of FIG. 10, display 36 of patient programmer 30 provides user interface 168 to the user, such as patient 12, via screen 194. Screen 194 includes stimulation icon 174, IMD battery icon 176, programmer battery icon 178, and automatic posture response icon 182, similar to screen 170 of FIG. 9. In addition, screen 194 includes group selection icon 184, group identifier 186, supplementary posture state indication 202, program identifier 196, posture state indication 200, amplitude value 204, selection box 192, and selection arrows 180. User interface 168 provides information to patient 12 regarding group, program, amplitude, automatic posture response status, and posture state information. More or less information may be provided to patient 12, as desired by the clinician or patient 12.

Group identifier 186 indicates that group "B" is active, and automatic posture response icon 182 indicates group "B" (containing one or more programs) is activated to allow IMD 14 to automatically adjust therapy according to the posture state of patient 12. Specifically, the posture state of patient 12 is the posture state in the example of FIG. 10. Program identifier 196 illustrates that information regarding program "1" of group "B" is displayed on screen 194, such as amplitude value 204 illustrating the current voltage amplitude of program "1" is 2.85 Volts. Patient 12 may scroll through different programs of the group by using navigation arrows 180 via arrows 44 and 48 of control pad 40.

In addition, posture state indication 200 shows that IMD 14 has detected that patient 12 is in the upright or standing posture. Supplementary posture state indication 202 supplements posture state indication 200 by illustrating in words to patient 12 the exact posture being detected by posture state module 86 of IMD 14. Posture state indication 200 and supplementary posture state indication 202 change according to the sensed, or detected, posture state detected by IMD 14. The posture state may be communicated to external programmer 20 immediately when IMD 14 detects a posture change, or communicated periodically or non-periodically by IMD 14 unilaterally or upon receiving a request from programmer 20. Accordingly, the posture state indication 200 and/or supplementary posture state indication 202 may represent a current, up-to-the minute status, or a status as of the most recent communication of posture state from IMD 14. Posture state indication 200 is shown as a graphical representation, but the posture state indication may alternatively be presented as any one of a symbolic icon, a word, a letter, a number, an arrow, or any other representation of the posture state. In some cases, posture state indication 200 may be presented without supplementary posture state indication 202.

Selection box 192 indicates that patient 12 view other programs within group "B" using selection arrows 208. Selection box 192 may be moved to select other screen levels with control pad 40 in order to navigate through other stimulation groups or adjustable elements of the therapy. When patient 12 selects a different program with control pad 40, program identifier 196 will change number to correctly identify the current program viewed on screen 194.

In addition to graphical, textual or other visible indications of posture state, the external programmer may present audible and/or tactile indications of posture state via any of a variety of audible or tactile output media. An audible indication may be spoken words stating a posture state, or different audible tones, different numbers of tones, or other audible information generated by the programmer to indicate posture state. A tactile indication may be, for example, different numbers of vibratory pulses delivered in sequence or vibratory pulses of different lengths, amplitudes, or frequencies.

IMD 14 provides posture-responsive therapy. I.e., IMD 14 or an external programmer 20 detects changes in patient posture and automatically adjusts therapy based on the patient posture. These therapy adjustments may be manually programmed in IMD 14 or an external programmer 20, e.g., a clinician may specify one or more therapy programs for each patient posture. In addition, as discussed with respect to FIGS. 11 and 12, automatic therapy adjustments due to changes in patient posture may also be based on recorded associations between manual patient therapy adjustments and patient posture. I.e., IMD 14 or an external programmer 20 associate manual patient therapy adjustments with patient postures and then automatically repeat those therapy adjustments for the corresponding patient postures.

Figure 11:
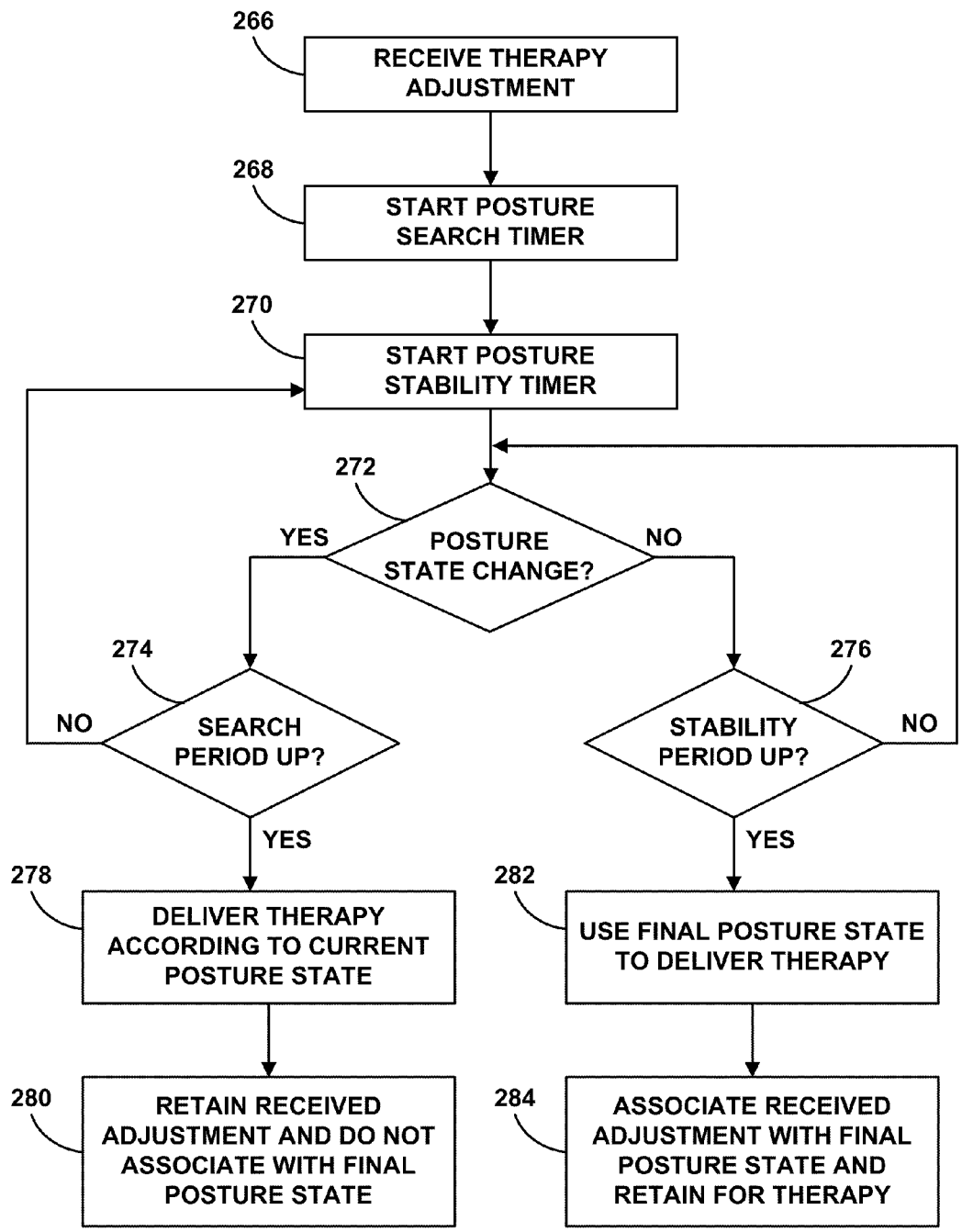
FIG. 11 is a flow diagram illustrating an example method for associating a received therapy adjustment with a posture state.

FIG. 11 is a flow diagram illustrating an example method for associating a received therapy adjustment with a posture state. In general, IMD 14 or an external programmer 20 detects patient adjustments to electrical stimulation therapy delivered to a patient during multiple instances of a sensed posture state, and associating the detected patient adjustments with the sensed posture state of the patient. The associations are stored in memory for later retrieval to view associations and/or support various programming techniques for programming of therapy parameters for posture state-responsive therapy. Although the example of FIG. 11 will be described with respect to patient programmer 30 and IMD 14, the technique may be employed in any external programmer 20 and IMD or other computing device. As shown in FIG. 11, user interface 106 receives the therapy adjustment from patient 12 (266) and processor 80 of IMD 14 immediately starts the posture search timer (268) and the posture stability timer (270).

If the posture state of patient 12 does not change (272), processor 80 checks to determine if the stability period has expired (276). If the stability period has not expired (276), processor 80 continues to sense for a posture state change (272). If the stability period has expired (276), the processor 80 uses the final posture state, i.e., the currently sensed posture state, to select therapy parameters to deliver therapy (282). Processor 80 then associates the therapy adjustment with the final posture state and retains the therapy adjustment for current therapy (284).

If processor 80 senses a posture state change (272), processor 80 determines if the search period has expired (274). If the search period has not expired (274), then processor 80 restarts the posture stability timer (270). If the search period has expired (274), then processor 80 delivers therapy to patient 12 according to the current posture state (278). Processor 80 retains the therapy adjustment and does not associate the therapy adjustment with the final posture state because the search period did not overlap with the stability period (280). Using the search and stability timers, each of the detected adjustments is associated with a sensed posture state if the sensed posture state is sensed within a search period following the detection of the adjustment and if the sensed posture state does not change during a stability period following the sensing of the sensed posture state.

In some examples, as an alternative, a posture stability timer may be employed without the use of a posture search timer. As described with respect to posture stability timer 260, the posture stability timer may be started after a therapy adjustment and reset each time patient 12 changes posture states prior to expiration of the posture stability timer. When the posture stability timer 260 expires, the therapy adjustment may be associated with the posture state that patient 12 is occupying at that time. In this manner, the therapy adjustment may be associated with the first stable posture state, i.e., the first posture state that remains stable for the duration of the posture stability timer, after the therapy adjustment, regardless of the amount of time that has passed since the therapy adjustment. Hence, in some implementations, processor 80 may apply only a stability timer without a search timer. In some cases, the use of only a stability timer, without a search timer, may be approximated by setting the search timer value to a large value, such as 24 hours. The effect of a very large search timer value is to operate with only a stability timer.

It should be noted that, in an example implementation, processor 80 may not change therapy to patient 12 at any time until the stability period expires. In other words, the posture stability timer may run independently of the posture search timer to always track posture states independently of therapy adjustments. Therefore, IMD 14 may not perform any automatic posture state-responsive stimulation until the posture state of patient 12 is stable and the stability period has expired. In this manner, patient 12 may not be subjected to rapidly changing therapy when transitioning between multiple posture states. Alternatively, IMD 14 may employ a separate posture stability timer for changing therapy during automatic posture response from the therapy adjustment related posture stability timer described herein.

Figure 12:
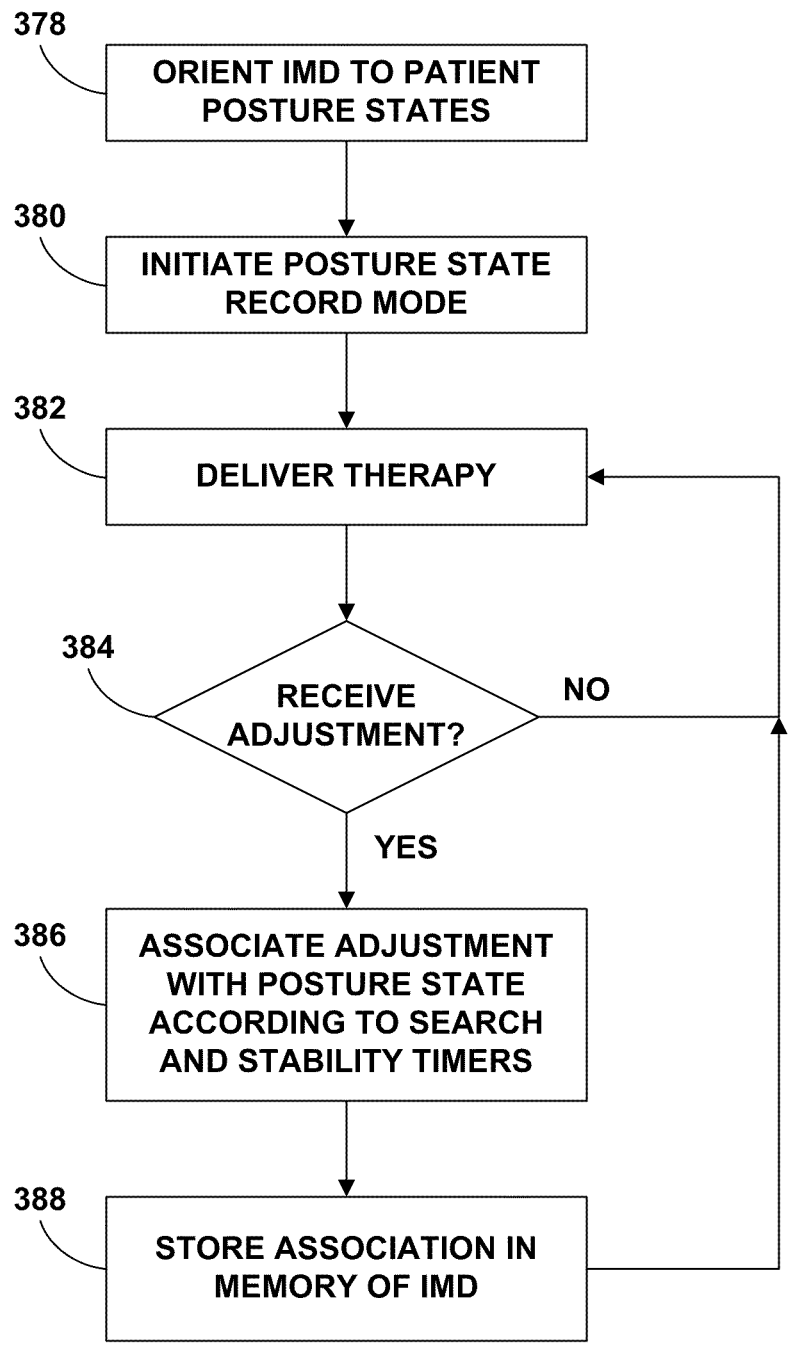
FIG. 12 is a flow diagram illustrating an example method for associating therapy adjustments with posture states.

FIG. 12 is a flow diagram illustrating an example method for associating therapy adjustments with posture states. As shown in FIG. 12, the clinician uses clinician programmer 60 to orient the posture state sensor in the IMD to posture states of patient 12 (378). For example, sensed vectors can be obtained for each of a plurality of posture states, and used as reference coordinate vectors either alone or to define posture state cones or other volumes, such as lying posture donut- or toroid-like volumes, as described in this disclosure. Next, clinician programmer 60 receives input to initiate the posture state recording that associates therapy adjustments made by the patient to posture states (380). Alternatively, posture state recording may occur in a substantially continuous manner, and may rely upon memory in IMD 14. For example, when a sensed vector indicates a particular posture state, e.g., by reference to cones, vectors, or the like, and a patient makes a therapy adjustment, that therapy adjustment may be associated with the indicated posture state. After all other programming is completed, IMD 14 delivers therapy to patient 12 according to the therapy parameters stored as groups of programs (382).

If IMD 14 does not receive a therapy adjustment from patient 12 via patient programmer 30 (384), IMD 14 continues delivering therapy to patient 12 (382). However, if IMD 14 does receive a therapy adjustment from patient 12 via patient programmer 30 (384), processor 80 of IMD 14 associates the therapy adjustment with the appropriate posture state as determined by the posture search timer and the posture stability timer (386), or only the posture stability timer in other examples. In addition, IMD 14 may immediately modify the therapy based on the patient therapy adjustment, and deliver the therapy to the patient 12. Processor 80 then stores the association in memory 82 of IMD 14 (388) in addition to any other associates made for the same posture state. The stored association may be retrieved by an external programmer for viewing by a user such as a clinician, e.g., for use in analysis of therapeutic efficacy and programming of the IMD. IMD 14 then continues delivering therapy to patient 12 (382). Alternatively, patient programmer 30 may perform the associations and/or store the associations instead of IMD 14. A clinician programmer 60 may retrieve the associations from patient programmer 30.

As a refinement to the process of associating therapy adjustments with posture states, IMD 14 and/or an external programmer 20 may be configured to apply a more stringent posture state detection requirement. A posture state detection process may detect a posture state based on any of the processes described in this disclosure, including those described with reference to FIGS. 8A-8C. As one example, a posture state may be detected if a sensed coordinate vector resides within a specified angle, cosine value, or distance of a particular reference coordinate vector for a particular posture state. However, a process for associating therapy adjustments with posture states may require that the sensed coordinate vector be located more closely to the reference coordinate vector. In this case, even if a particular posture is detected based on the location of the sensed coordinate vector within a first tolerance range of the reference coordinate vector, patient therapy adjustments are associated with the detected posture state only if the sensed coordinate vector is located within a second, tighter tolerance range of the reference coordinate vector. The second range for association is smaller than the first range for detection, requiring closer proximity of the sensed coordinate vector to the reference coordinate vector for an association to be made.

Hence, in this alternative implementation, IMD 14 or programmer 20 makes an association between a patient therapy adjustment and a posture state if a more stringent posture detection criteria is met. For example, in the example of a cone-based posture detection scheme, where each posture state is defined by a reference coordinate vector and a cone defining a tolerance angle, a patient may be detected as being in the face up posture state if he is plus or minus 30 degrees from the reference coordinate vector for the face up cone. For purposes of associating patient therapy adjustments with posture state, however, IMD 14 or programmer 20 makes the association only if the patient is detected in the face up posture state, and the patient is within plus or minus 15 degrees from the coordinate reference vector for the face up posture state cone.

In a toroid-based detection scheme, the patient would be classified as lying if he is greater than 60 degrees, for example, away from an upright reference coordinate vector or virtual upright reference coordinate vector. For purposes of association of patient therapy adjustments with posture states, however, IMD 14 or programmer 20 may be configured to only associate a therapy adjustment with a lying posture state if the patient is greater than 75 degrees, for example, from an upright reference coordinate vector or virtual upright reference coordinate vector. In each of these examples, in determining whether to associated patient therapy adjustments with posture states, IMD 14 or programmer 20 applies association criteria or logic with an increasing specificity applying more conservative tolerance criteria than the posture state detection in general.

During clinician visits, it is useful for the clinician to receive, comprehend and evaluate information relating to electrical stimulation therapy as efficiently as possible. For example, when a patient visits a clinician, there are some basic questions the clinician may ask the patient: "(1) Is your device working? (2) Is your pain being covered? (3) Have you been able to recharge?" FIGS. 13-25 demonstrate presentation techniques for therapy factors, i.e., information relating to the therapy that can factor into the clinician's evaluation of the condition of the patient, the effectiveness of the therapy, and whether there should be any adjustments for continuing therapy. The presentation techniques for therapy factors disclosed with respect to FIGS. 13-25 may allow the physician to quickly determine if therapy is effective for a patient, if the patient is using their device, the condition of the patient, and whether there should be any adjustments for continuing therapy.

Data for therapy factors presented in FIGS. 13-25 is generally recorded by circuitry of an implanted medical device (IMD) and then transferred to a programmer, e.g., clinician programmer 60 (FIG. 3) for presentation. In some cases, the data may be intermediately transferred from an IMD to a patient programmer, e.g., patient programmer 30 (FIG. 2) before transferred to a clinician programmer. In addition, some therapy factors may be stored directly in either a patient programmer 30 or clinician programmer 60. For example, subjective information, such as information used to produce pain/paresthesia maps, may be stored directly on a patient programmer 30 before transferred to a clinician programmer 60 for presentation to a clinician or other user.

Figure 13:
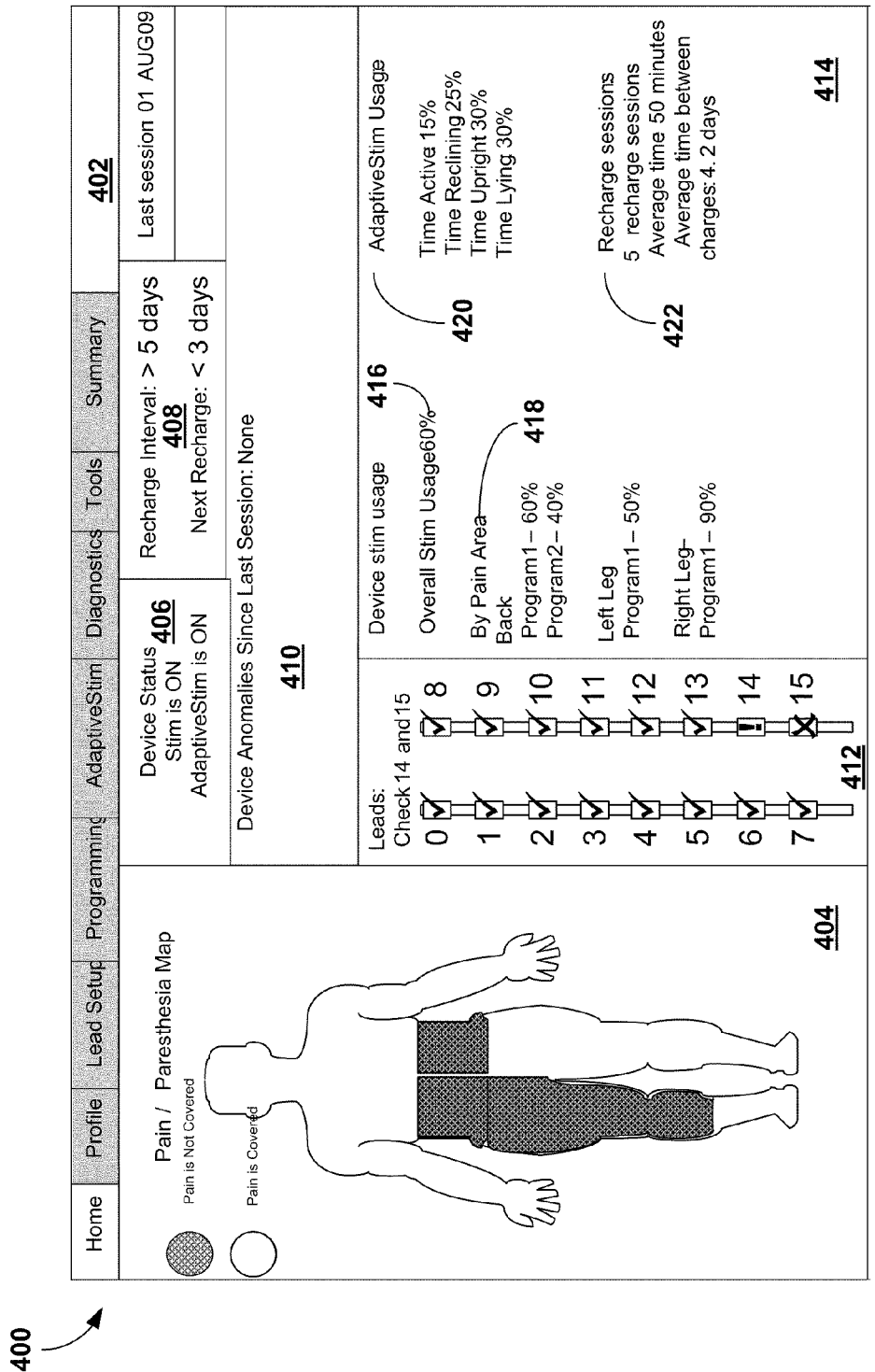
FIG. 13 illustrates an exemplary home screen for a clinician programmer displaying a variety of information relating to electrical stimulation therapy for chronic pain.

FIG. 13 illustrates an exemplary home screen 400 for a clinician programmer, e.g., clinician programmer 60 (FIG. 3) displaying a variety of information relating to electrical stimulation therapy for chronic pain. Home screen 400 provides a multitude of information to assist a clinician in evaluating the condition of the patient, the effectiveness of the electrical stimulation therapy, and whether there should be any adjustments for continuing therapy. Specifically, home screen 400 includes navigation toolbar 402, pain/paresthesia map 404, device status 406, recharge interval information 408, device anomalies information 410, lead electrode status indication 412 and stimulation usage information 414. The tabs of navigation toolbar 402 allow the user to set up and program the parameters of the stimulator as well as view therapy factors. Pain/paresthesia map 404, device status 406, recharge interval information 408, device anomalies information 410, lead electrode status indication 412 and stimulation usage information 414 present different therapy factors, i.e., information relating to the therapy that can factor into a user's evaluation of the condition of the patient, the effectiveness of the therapy, and whether there should be any adjustments for continuing therapy.

During a clinician-patient visit for a patient receiving electrical stimulation therapy for chronic pain, the clinician may first want to know if the patient's pain is being covered. Pain/paresthesia map 404 graphically represents areas of pain felt by a patient as well as areas of paresthesia felt by the patient due to electrical stimulation therapy. Populating pain/paresthesia map 404 may include receiving subjective inputs from the patient regarding pain and paresthesia felt by the patient. The subject inputs could include an identification of locations of pain and paresthesia as well as an indication of the amount of pain or paresthesia experienced by the patient. In this manner, pain/paresthesia map 404 includes a subjective record of pain experienced by the patient. Techniques for producing pain/paresthesia maps are described in U.S. Pat. No. 6,308,102 to Sieracki et al., which is incorporated herein by reference in its entirety.

During a clinician-patient visit for a patient receiving electrical stimulation therapy for chronic pain, the clinician may also want to know if the lead electrodes are experiencing any problems. Such information is relevant in determining suitable electrical stimulation therapy programs for the patient. Lead electrode status indication 412 includes a graphical representation of two leads and electrodes 0:15. As shown in electrode status indication 412, electrodes 14 and 15 are experiencing degraded performance, specifically electrode 14 is experiencing a high impedance, whereas electrode 15 is open, i.e., very high or infinite impedance, making it unsuitable for use in stimulation. Data for used to display electrode status indication 412 is initially obtained by the medical device, such as an implantable electrical stimulator, and then transmitted to the programmer via telemetry. For this reason, the implantable electrical stimulator includes impedance measurement circuitry.

Stimulation usage information 414 includes a variety of information associated with delivering electrical stimulation therapy to a patient. Specifically, stimulation usage information 414 includes an indication of the overall rate of stimulation usage 416 as recorded by the electrical stimulator since a previous programming session as well as indications of the overall program usage rates 418 for three different slots: back, left leg and right leg, as recorded by the electrical stimulator. In the example of FIG. 13, stimulation usage information 414 also includes indications of the overall rate of patient posture 420, which is used for adaptive stimulation. In other examples, the overall rate of patient posture occupied by the patient, as detected by the electrical stimulator, can be represented using a pie chart, bar graph, or similar graphical depiction. Finally, stimulation usage information 414 includes recharge summary 422. Recharge summary 422 provides lists the number of recharge sessions, the average time for each recharge session and the average time between recharge sessions.

Figure 14:
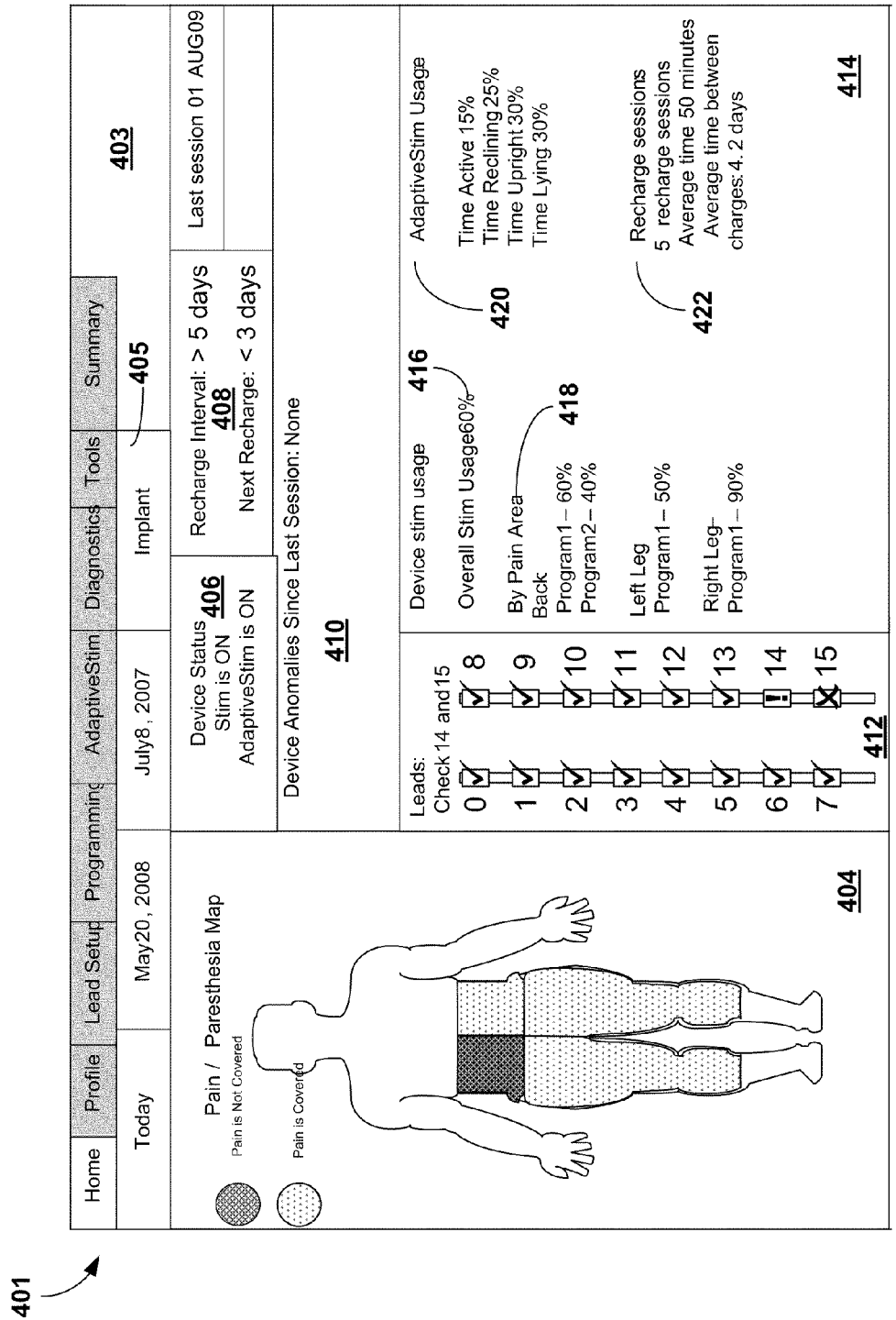
FIG. 14 illustrates an exemplary home screen for a clinician programmer including a set of sub-tabs allowing a user to quickly review information relating to electrical stimulation therapy for chronic pain for different time periods.

FIG. 14 illustrates an exemplary home screen 401 for a clinician programmer. Home screen 401 is substantially similar to home screen 400 (FIG. 13), except that navigation toolbar 403 includes a set of sub-tabs 405 allowing a user to quickly review information relating to neurostimulator treatments for chronic pain for different time periods, such as, e.g., today, a previous clinician visits or at implantation of an implantable neurostimulator. The today tab brings up information recorded since the most recent clinician visit, and the dated tabs brings up information recorded prior to those clinician visits. Similarly, the implant tab brings up information of the patient conditions at implantation of the medical device, such as an implantable electrical stimulator. For example, clicking the implant tab may bring up a pain/paresthesia map similar to pain/paresthesia map 432 in FIG. 15.

Figure 15:
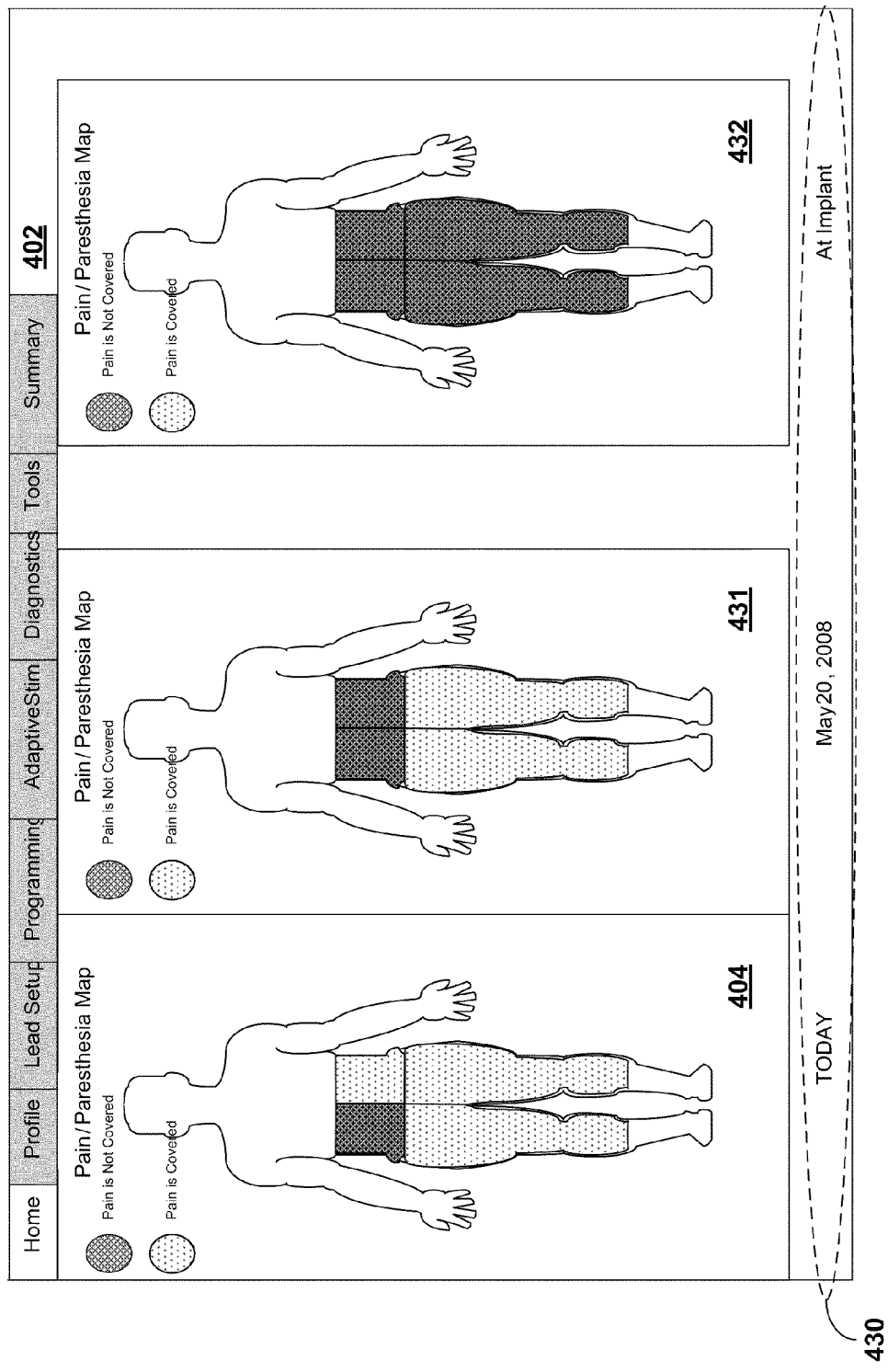
FIG. 15 illustrates an exemplary screen shot of a clinician programmer simultaneously displaying pain paresthesia maps for three different time periods during delivery of electrical stimulation therapy.

FIG. 15 illustrates an exemplary screen shot of a clinician programmer simultaneously displaying pain/paresthesia maps for three different time periods along timeline 430. As referred to herein, a timeline is representation of a time interval or a plurality of specific time periods. FIG. 15 illustrates three discrete time periods along timeline 430. Specifically, FIG. 15 includes pain/paresthesia maps 404, 431 and 432. Pain/paresthesia map 404 indicates areas of pain felt by a patient as well as areas of paresthesia felt by the patient today; pain/paresthesia map 404 was also shown in home screen 400 (FIG. 13) and home screen 401 (FIG. 14). Similarly, pain/paresthesia map 431 indicates areas of pain felt by a patient as well as areas of paresthesia felt by the patient on May 20, 2008, during a previous programming session. Finally, pain/paresthesia map 432 indicates areas of pain felt by a patient prior to the beginning of electrical stimulation therapy by an implanted neurostimulator. For this reason, pain/paresthesia map 432 does not include any areas of paresthesia. In particular, electrical stimulation therapy was not applied prior to collection of subjective pain map data for map 432.

Figure 16:
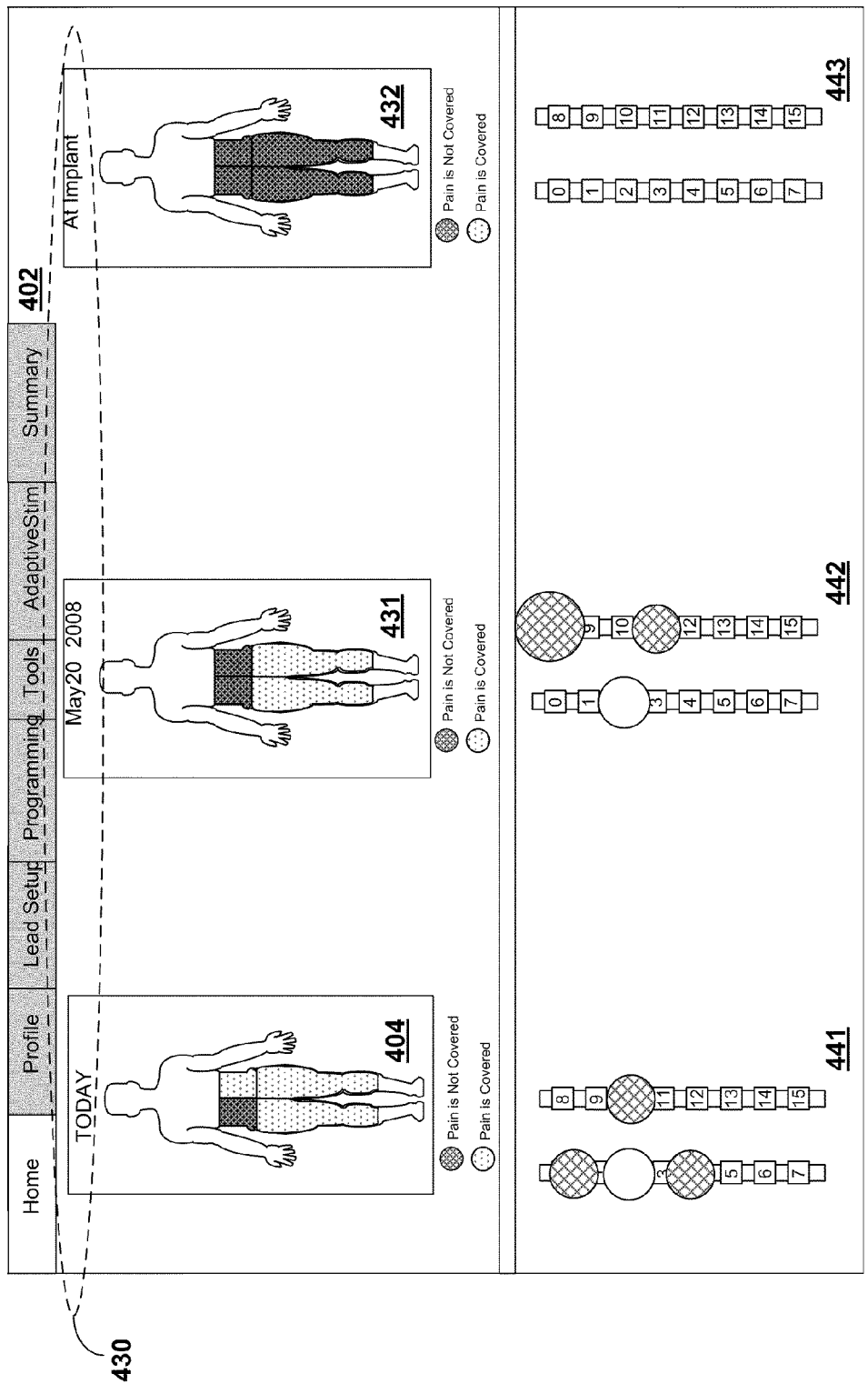
FIG. 16 illustrates an exemplary screen shot of a clinician programmer simultaneously displaying pain paresthesia maps for three different time periods during delivery of electrical stimulation therapy as well as corresponding active stimulation programs along a common timeline.

FIG. 16 illustrates an exemplary screen shot of a clinician programmer simultaneously displaying pain paresthesia maps 404, 431 and 432 as well as corresponding graphical representations of active stimulation programs 441, 442 and 443 along a common timeline 430. Pain/paresthesia maps 404, 431 and 432 present the combined effect of multiple slots, each slot may be provided to target different anatomical regions, e.g., slot 1 may target left leg pain, slot 2 may target right leg pain, slot 3 may target right knee pain, etc.

In stimulation programs 441, 442 and 443, the circles represent active electrodes on respective leads carrying multiple electrodes, wherein the white circles represent anodes and the shaded or hashed circles represent cathodes. Larger circles may represent higher voltage or current amplitudes (depending on whether controlled voltage or controlled current pulses are used for electrical stimulation) of active electrodes, whereas smaller circles may represent lower voltage or current amplitudes. For ease of illustration, FIG. 16 shows bipolar and multipolar lead configurations. However, unipolar or omnipolar lead configurations may also be used.

As shown in FIG. 16, no stimulation was applied for stimulation program 443. Stimulation programs 441, 442 and 443 only represent a single program from a single slot. In other examples, programs for multiple slots could also be shown along common timeline 430 simultaneously or by toggling between the multiple slots on a selective basis. In addition, other therapy factors associated with delivering electrical stimulation therapy may also be presented along common timeline 430 in combination with pain paresthesia maps 404, 431 and 432 and the corresponding graphical representations of active stimulation programs 441, 442 and 443. Such therapy factors associated with delivering electrical stimulation therapy includes, but is not limited to, indications of patient posture, battery charge information for the neurostimulator, and one or more physiological conditions of the patient. Presenting multiple therapy factors associated with delivering electrical stimulation therapy to the user simultaneously, and along a common timeline, can allow the user to quickly recognize interrelationships between the presented therapy factors.

Figure 17:
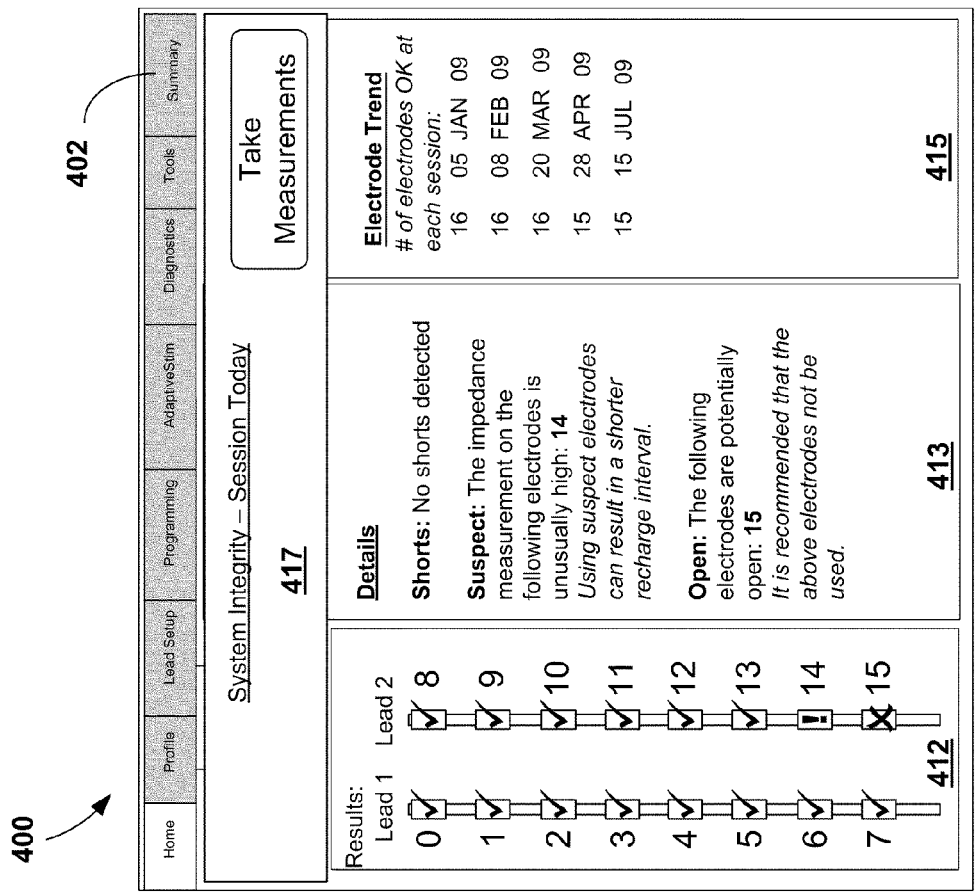
FIG. 17 illustrates an exemplary screen shot of a clinician programmer showing lead diagnostic information and history.

FIG. 17 illustrates an exemplary screen shot of a clinician programmer showing lead diagnostic information and history. FIG. 17 includes electrode status indication 412, which was also shown in FIG. 13. Electrode status indication 412 illustrates two leads, each having eight electrodes. Selecting electrode status indication 412 on home screen 400, navigates to the lead diagnostic information and history detail screen shown in FIG. 17. Included in FIG. 17 is electrode status indication 412, electrode status detailed explanation 413, electrode trend information 415 and selectable electrode system integrity test activation 417. Electrode status detailed explanation 413 provides details of potential issues of electrodes. Specifically, electrode status detailed explanation 413 lists any shorts between electrode, electrodes having high impedances (out of specifications) and electrodes having even higher impedances (open electrodes).

When activated, electrode system integrity test activation 417 causes the neurostimulator to test each of the electrodes. The results of previous tests are shown as electrode trend information 415. More specifically, electrode trend information 415 lists a list of the number of electrodes that met preferred impedance specifications for a plurality of previous electrode integrity tests.

Figure 18:
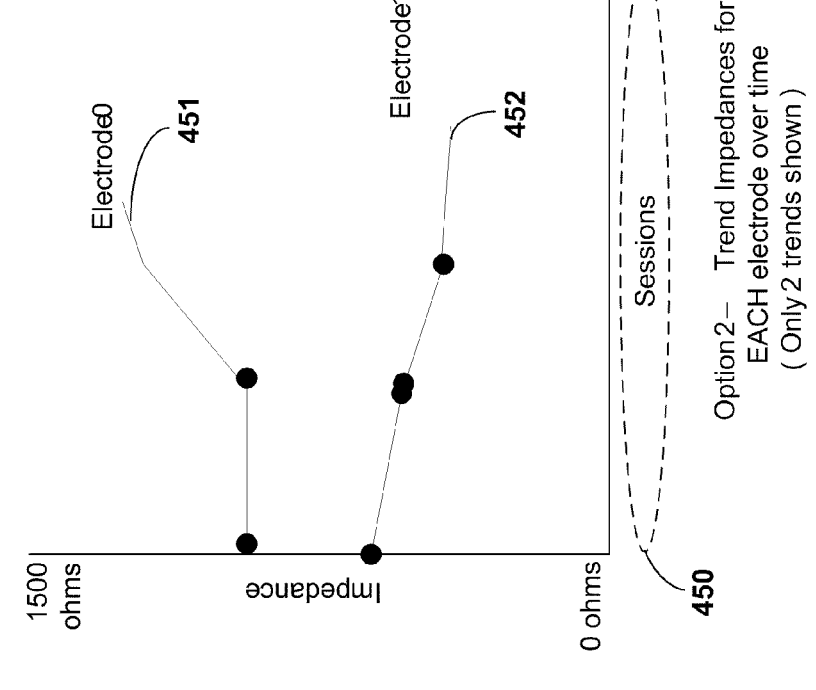
FIG. 18 illustrates a chart illustrating electrode impedance history.

FIG. 18 is a portion of a screen shot that may be used in place of electrode trend information 415 in the screen shot displayed in FIG. 17. As an alternative to impedance trends of one or more electrodes as shown in FIG. 18, in a medical system comprising a catheter, trends of a catheter pressure can be illustrated. As illustrated in FIG. 18, impedance trends of one or more electrodes could be shown as a line graph in place of electrode trend information 415. Impedance trend 451 provides additional detail relative to electrode trend information 415. Specifically, impedance trend 451 presents the actual impedances of electrodes over time, whereas electrode trend information 415 merely provides a count of electrodes that meet impedance specifications over time. FIG. 18 illustrates impedance trend 451 for electrode 0 and impedance trend 452 for electrode 1 along common timeline 450. In other examples, impedance trend information for additional or different electrode could be shown along a common timeline. For example, impedance trend information could be shown for only those electrodes experiencing problems, e.g., electrodes 14 and 15 (as indicated by electrode status indication 412).

Figure 19:
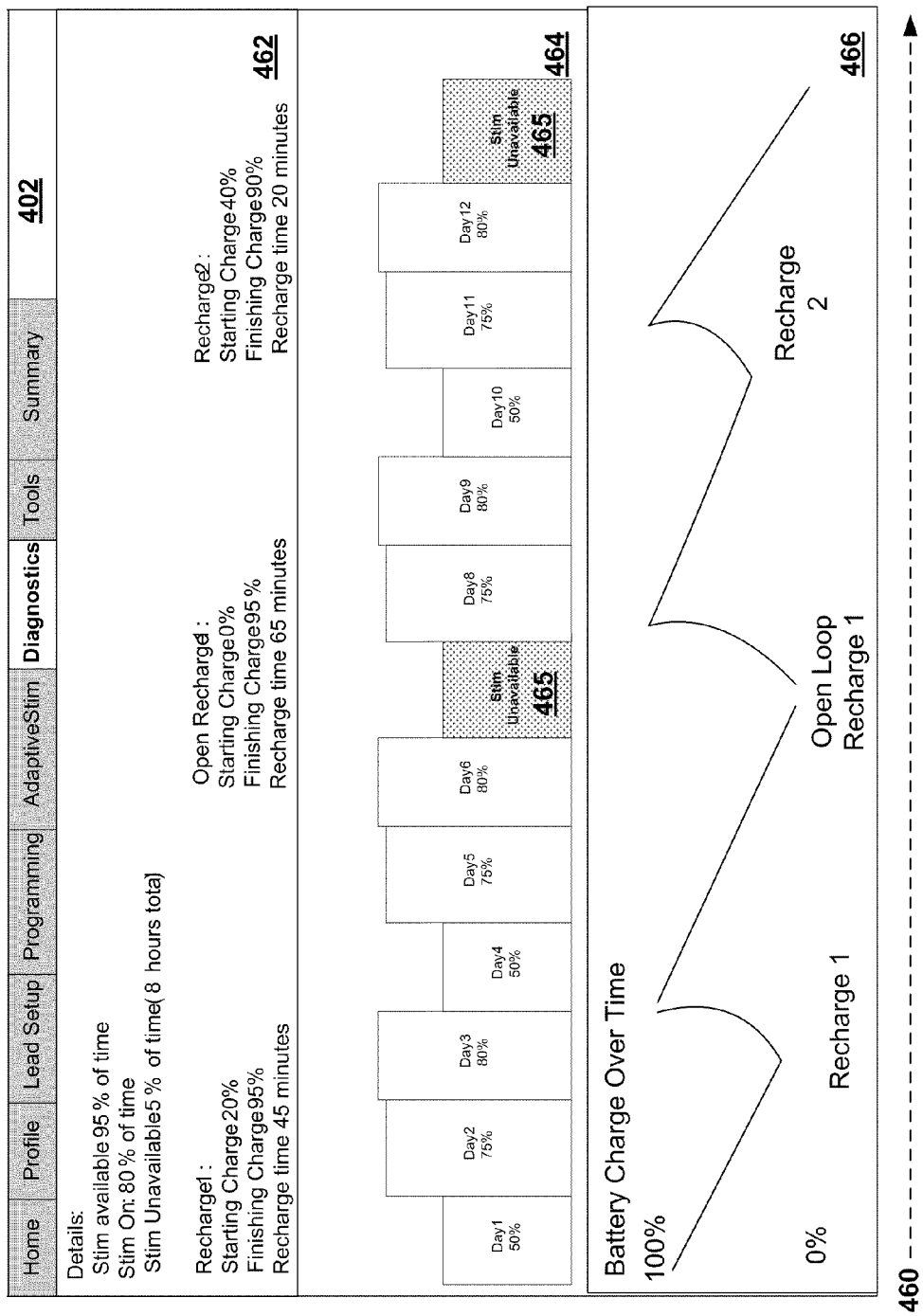
FIG. 19 illustrates an exemplary screen shot of a clinician programmer simultaneously displaying daily stimulation activity as well as corresponding battery charge levels along a common timeline.

FIG. 19 illustrates an exemplary screen shot of a clinician programmer simultaneously displaying daily stimulation activity 464 as well as corresponding battery charge levels 466 along common timeline 460. As referred to herein, a timeline is representation of a time interval or a plurality of specific time periods. FIG. 19 illustrates continuous time period of days 1-13 along timeline 430. Daily stimulation activity 464 represents the percentage of time in a day that at least one stimulation program was being applied. FIG. 19 provides an integrated view of the amount of time stimulation is used each day versus the battery charge level of the medical device for that day along timeline 460. Selecting the diagnostic tab of navigation toolbar 402 from the home screen navigates to the screen shown in FIG. 19.

FIG. 19 includes a summary of battery charging history as well as stimulation activity in diagnostic summary 462. In addition, FIG. 19 as provides a series of graphical indications of daily stimulation activity 464 and battery charge history using indications of battery charge level 466 along common timeline 460. Daily stimulation activity 464 is presented as a series of daily values representing the percentage of time that at least one stimulation program was delivered for each day along common timeline 460. Stimulation unavailable indications 465 for days 7 and 13 in daily stimulation activity 464 represent days in which no stimulation was applied.

Battery charge level 466 is presented as a continuous line graph along common timeline 460. Battery charge level 466 demonstrates that normal recharging occurred on day 3 and day 11. In addition, as shown in battery charge level 466, there was one occurrence of an open loop recharge, on day 7. This circumstance occurred when the neurostimulator battery level was too low for the neurostimulator to communicate with the charger. In particular, the open loop recharge indicates a condition in which neurostimulator battery level is so low that a closed loop recharge process in which the neurostimulator may communicate charge status and/or recharge control signals to the external recharge device. In this case, before and/or during the open loop recharge cycle, the charge level may be so low that stimulation is unavailable, as further shown in FIG. 19.

Presenting stimulation activity and battery charge history information along a common timeline allows a user to quickly recognize that a period of non-stimulation activity may have occurred due to a low battery charge level. After recognizing that a period of non-stimulation activity may have occurred due to a low battery charge level, a clinician might advise a patient to charge the neurostimulator more frequently to prevent such periods of non-stimulation activity in the future.

While daily stimulation activity 464 is displayed as a bar chart, other display techniques may be used such a line graph or a numerical list stimulation activity for each day (or other time period). Likewise, while battery charge level 466 is displayed as a line graph, other display techniques may be used such a bar chart or a numerical list of maximum and minimum battery charge levels for each day (or other time period). Any other suitable techniques may be used to present stimulation activity, battery charge history information, and other information associated with delivering electrical stimulation therapy along a common timeline.

Figure 20:
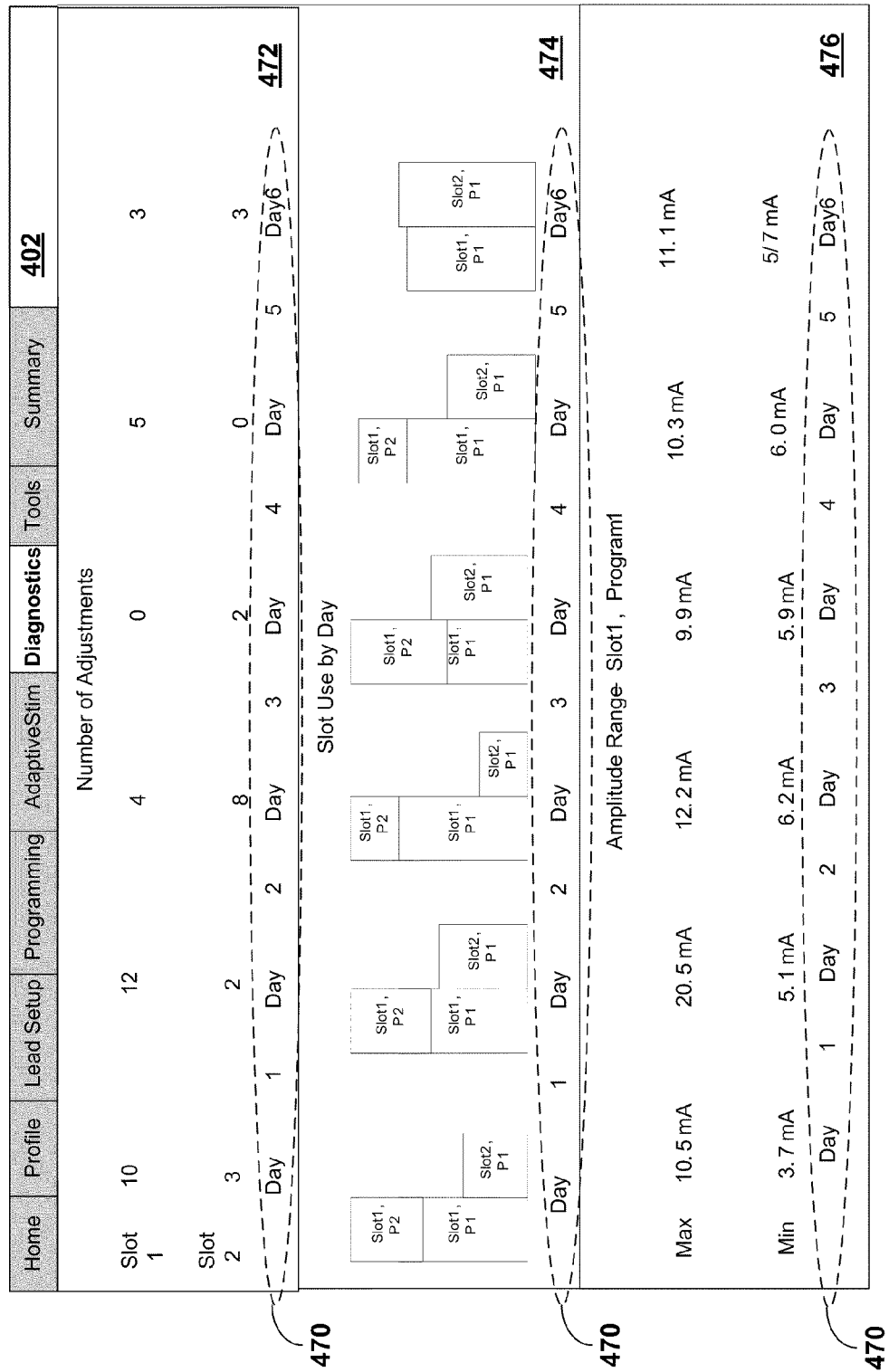
FIG. 20 illustrates an exemplary screen shot of a clinician programmer simultaneously displaying daily stimulation adjustments, daily stimulation program usage, and daily stimulation amplitude ranges along a common timeline.

FIG. 20 illustrates an exemplary screen shot of a clinician programmer simultaneously displaying a count of daily stimulation adjustments 472, daily stimulation program usage 474, and daily stimulation amplitude ranges 476 along common timeline 470. Daily stimulation adjustments 472 represent the number of manual adjustments of therapy by the patient for each of two program slots: slot 1 and slot 2. For example, in day 1, the patient adjusted stimulation associated with slot 1 ten times, e.g., by switching programs or adjusting the stimulation amplitude. In contrast, the patient only adjusted stimulation associated with slot 2 three times.

Daily stimulation program usage 474 provides a series of graphical representations of the program usage rates for each of each of the two program slots: slot 1 and slot 2. As can be seen from in daily stimulation program usage 474, each day, the patient used two different programs in slot 1 and only a single program in slot 2. In addition, on days 1 to 5, electrical stimulation associated with slot 1 was delivered for a greater percentage of the day than electrical stimulation associated with slot 2. For example, electrical stimulation associated with slot 1 could have been delivered near-continuously on days 1, 2, 3 and 4. In contrast, on day 6, electrical stimulation associated with slot 2 was delivered a slightly greater percentage of the day than electrical stimulation associated with slot 1.

Daily stimulation amplitude ranges 476 are shown as lists of the minimum and maximum amplitudes used in days 1-6 for slot 1, program 1. The minimum and maximum values include therapy program amplitude parameters as modified by manual therapy adjustments by a patient (when applicable). In other examples, amplitude ranges for additional programs and/or slots could also be shown along common timeline 470.

Presenting daily stimulation adjustments, daily stimulation program usage 474, and daily stimulation amplitude ranges along common timeline allows a user to evaluate the effectiveness of therapy. While an IMD may automatically adjust therapy based on patient posture, a patient may still perform manual adjustments to the selected program or program amplitudes in attempt to improve the efficacy of the therapy. In this manner, more adjustments might indicate a higher level of patient discomfort with the automatically applied therapy parameters.

While daily stimulation program usage 474 is displayed as a bar chart, other display techniques may be used such a line graph or a numerical list stimulation program usage for each day (or other time period). Likewise, while daily stimulation adjustments 472 and daily stimulation amplitude ranges 476 are displayed numerical lists, other display techniques may be used such a bar chart or a line graph. Any other suitable techniques may be used to present daily stimulation adjustments, daily stimulation program usage, and daily stimulation amplitude ranges and other information associated with delivering electrical stimulation therapy along a common timeline.

Additional types of therapy factors associated with delivering electrical stimulation therapy to a patient can be presented to a user on a common timeline. For example, such information may include two or more of therapy factors, including but not limited to, an objective record of the electrical stimulation therapy delivered to the patient, a record of patient posture, a record of a battery charge history a battery of the neurostimulator, a subjective record of pain experienced by the patient, an objective record of one or more physiological conditions of the patient, and a record representative of electrode impedances for electrodes of medical leads associated with the neurostimulator. The therapy factors presented on a screen of a programmer on a common timeline may be selected by a user, such as a clinician or a patient.

Figure 21:
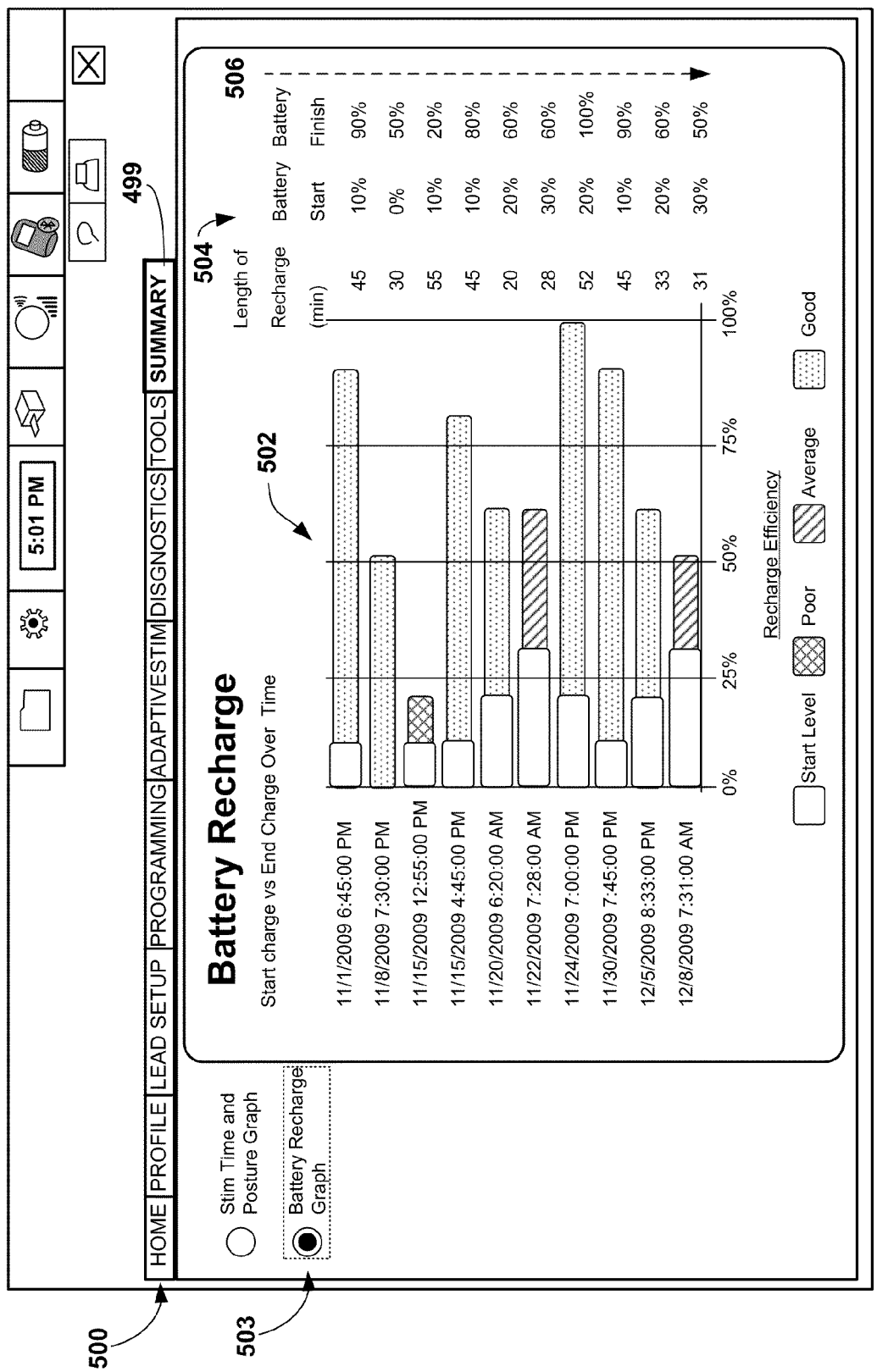
FIG. 21 illustrates an exemplary screen shot of a detailed summary of battery recharging sessions.

FIG. 21 illustrates an exemplary screen shot of a detailed summary of battery recharging sessions including bar chart 502 and table 504 along common timeline 506. A user navigates to the screen shot shown in FIG. 21 by selecting summary tab 499 in navigation toolbar 500, as battery recharge circle 503 is selected by default. The other tabs of navigation toolbar 500 allow the user to set up and program the parameters of the stimulator. FIG. 21 represents a troubleshooting tool to evaluate battery charging performance. Questions that the screen shot of FIG. 21 may help answer include, "Is the user recharging their battery effectively? (i.e. is coupling good/average/bad)," "Is the user completely draining the battery, which can result in loss of stimulation?" and "Is the user completely recharging the battery, which can indicate proper charging techniques?"

Bar chart 502 illustrates the battery charge at the beginning and end of each charging session. The thicker bars represent the battery charge at the beginning of each session, whereas the thinner bars represent the battery charge at the end of each session. For example, for the charging session of Nov. 1, 2009, the battery started with a 10 percent charge and ended with a 90 percent charge. Bar chart 502 may be color-coded to indicate the coupling quality between the charger and the battery. Since the battery is part of an IMD, charging occurs inductively. Misalignment between the charger and the charging coil of the IMD can significantly degrade charging performance. This is represented by the color-coded bars indicating the coupling quality between the charger and the battery for each of the charging sessions. Table 504 shows the battery charge at the beginning of each session, the battery charge at the end of each session and the length of the recharge.

Figure 22:
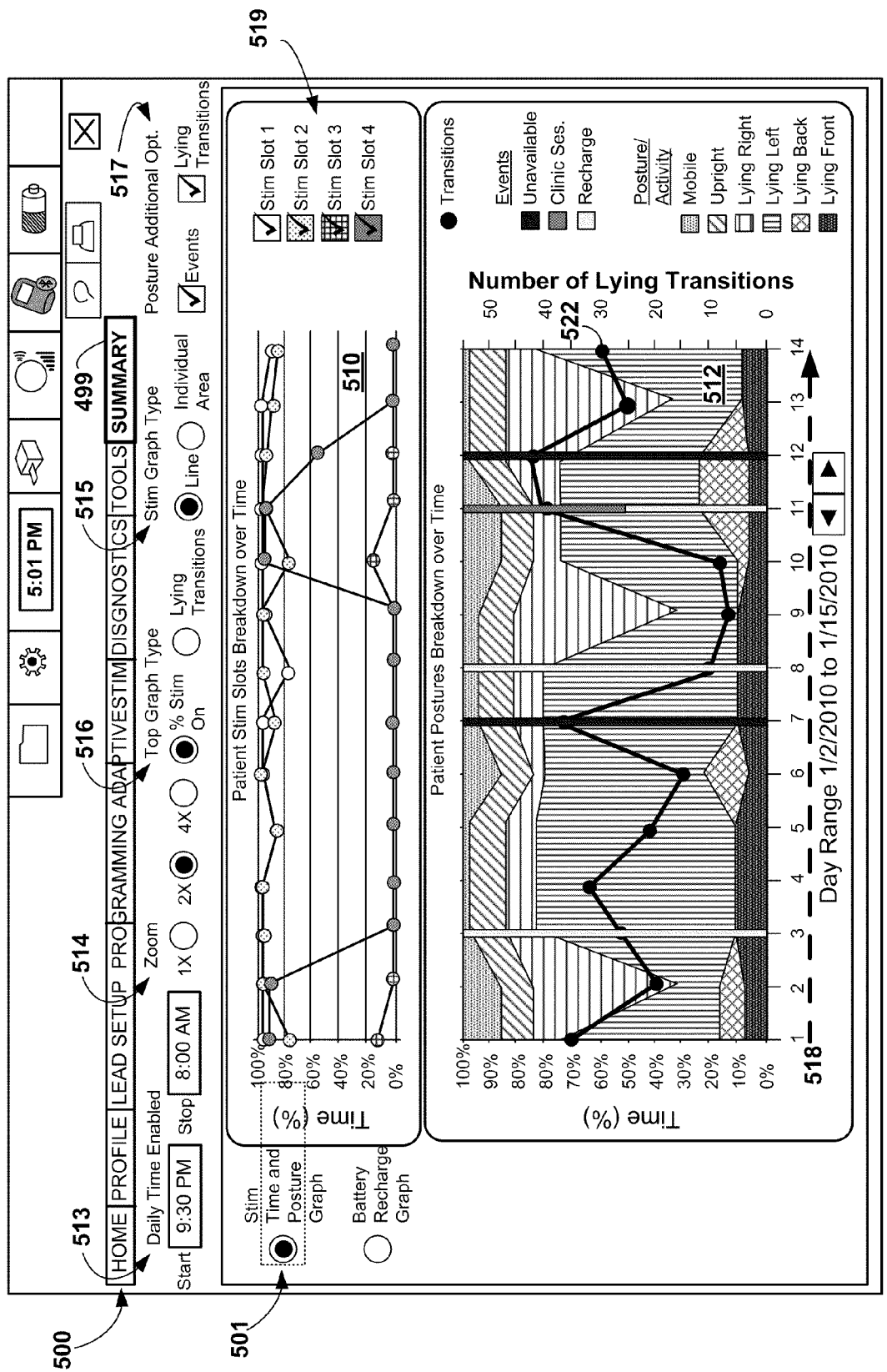
FIG. 22 illustrates an exemplary screen shot including two graphs: a breakdown of stimulation slot usage, and a patient postures graph with an overlay of showing occurrences of three significant events: recharging, clinician sessions (e.g., programming sessions) and device unavailability.

FIG. 22 is an exemplary screen shot of a programmer configured to present information corresponding to more than one therapy factor associated with delivery of medical therapy to a user, such as a clinician or patient, along common timeline 518. In addition, the user can select a subset of the information for presentation on the programmer. For example, a user can select specific portions of the data set, e.g., portions representing a daily time period or a patient activity level, in order to more easily interpret the data set. The user may use his or her interpretation of the data set in order to evaluate the efficacy of the therapy and/or adjust the therapy.

When at summary tab 499, a user navigates to the screen shown in FIG. 22 by selecting stim time and posture circle 501. The main goal of this screen is to allow the clinician to determine what postures the patient has been in over a recent period of time and if the patient has been using stimulation over time. The user can also present the number of lying transitions over some time period, which in this example is the last 14 days. A lying transition occurs when a user switches from one lying zone (e.g. lying left) to another (e.g. lying back).

FIG. 22 includes two graphs: stimulation slots breakdown 510 and patient postures 512. Stimulation slots breakdown 510 and patient postures 512 share the same x-axis, i.e., common timeline 518 and provide up to 30 days' worth of data by selecting the 1× zoom with zoom control 514.

Stimulation slots breakdown 510 displays the percentage of time that stimulation was active for each slot over a day. Stimulation slots breakdown 510 is presented as a line, but could also be displayed by either a line or area graph by selecting graph stim type 515.

Patient postures 512 presents the percentage of time each posture is being used over the last 14 days. This graph helps the clinician answer the following questions: "How often is the user lying down?" and "Is the user becoming more active (greater mobility, more reclining)?"

FIG. 22 also illustrates the controls available to the user. The times enabled control 513 facilitates, for any data series (stimulation, lying transitions, or postures) a user's select daily start and stop time periods. For example, if a user selects time periods from 9:30 PM to 8:00 AM, only data taken daily from 9:30 PM to 8:00 AM is presented.

Times enabled control 513 illustrates one example of a user selectable control that facilitates user selection of a subset of a data set associated with present therapy factors. Such user selectable controls allow a user to view less than all the information relating to the therapy factors in the data set. In other examples, other selectable controls may facilitate selection of therapy factors associated with one or more of the following: a therapeutic element in the medical system; a therapy setting associated with delivering a portion of the medical device therapy to the patient with the medical system, such a unipolar stimulation, bipolar simulation and/or omnipolar stimulation, a patient activity level, a patient posture, a patient posture and activity level, a patient mobility, a patient record of therapy outcome, an objective record of therapy outcome, an event recorded during the delivery of the medical device therapy to the patient with the medical system, and/or a recharge status of the implantable medical device.

The zoom control 514 allows a user to select three different time period intervals with different levels of resolution: 1× zoom=30 days, 2× zoom=15 days with scrollbar, 4× zoom=7 days with scrollbar. Short time period intervals provide relatively higher levels of resolution in the presentation of the data.

The top graph type control 516 allows a user to select the data shown in the top graph. If the "% Stim On" circle is checked, the top graph shows the patient stimulation slots breakdown over time with one of two graphs, based on the "Stim graph type" control 515. A user can enable/disable the display of particular slots by selecting checkboxes in legend 519.

Alternatively the top graph shows lying transitions when the "# of lying transitions" is selected in top graph type control 516. As shown in FIG. 22, when this checkbox is enabled, a line graph with the lying transitions is overlaid across the patient postures graph. The lying transitions data is subject to the same filtering rules based on time of day just like postures and stimulation data is filtered, e.g. 9:30 PM to 8:00 AM. Lying transitions represent the number of times a patient changes positing while lying down, such as when a patient is sleeping. Every time a patient rolls over, for example, would be counted as a lying transition. Higher lying transition may represent a patient has trouble sleeping, possibly due to patient discomfort. For this reason, a count of lying transitions may represent one way to evaluate the relative effectiveness of therapy, e.g., to compare the relative efficacy of different therapy programs.

The presentation of lying transitions 522 may help a clinician answer the following questions: "Can I determine if stimulation has helped to improve patient postures? (compare patient stimulation graph to patient posture graph)," "How is the patient sleeping? (look at patient postures with only times the patient is expected to be sleeping and analyze the number of lying transitions)," "How is the patient during the day? (look at the postures and stimulation graph times the patient is expected to be awake)." In addition, a patient could run a comparison over time, e.g., turn on stimulation for 7 days and turn off stimulation for 7 days, and then compare patient activity with stimulation on versus stimulation off.

"Stim graph type" control 515 allows a user to select between two different settings: "Line," which displays a line graph showing all 4 stimulation slots simultaneously, and "Individual area," which displays an area graph of 1 of the 4 stimulation slots. In this example, only one of the 1 stimulation slots can be shown at a time, they are mutually exclusive.

The posture add-ons control 517 has two checkable boxes: events and lying transitions. Checking the events box enables 3 additional series of data: recharging, clinician sessions (e.g., programming sessions) and device unavailability. The data for these events is shown in Table 1.

TABLE 1

| Recharge Times | Clinician Sessions | Device Unavailable |
|---|---|---|
| Day 3 | Day 11 | Day 7 |
| Day 8 | | Day 12 |
| Day 11 | | |

As illustrated in FIG. 22, the events are displayed as a narrow stacked bar chart lying on top of the patient postures chart. If one event is present, it will take 100% of the space. If more than one event is present, the values will be equally weighted, as shown for the data of Day 11. (50% if 2 are present, 33% if 3 are present). In this example, multiple events occurring on one day will only be counted once: one or more events of a certain type sets the "Boolean value" of the event to true. For example, if we had 3 recharge events on Day 11 and also had a clinician session on Day 11, we would still show a 50% white and 50% shaded line as shown in FIG. 22.

Presenting one or more events in combination with other therapy factors can help a user understand interrelationships between therapy factors. For example, with respect to Days 7 and 12, the relatively high number of lying transitions may be associated with the unavailability events. The unavailability events may be due to a patient failing to adequately recharge an IMD, leading to the unavailability of therapy and thus more restless sleep (as indicated by the number of lying transitions). In this example, a clinician may provide addition instructions on charging the IMD to the patient to mitigate the occurrence of unavailability events in the future.

In other examples, the display of one or more events may be selectable. Such selectable events may include any combination of the following: programming sessions, device resets, MRI mode, an impedance or catheter pressure jump, falls (as indicated by a high acceleration), hospital admissions (as indicated by a manual user entry), periods of epileptic seizures or other epileptic events, patient entries such as an indication of an uncomfortable shock from an electrical stimulation therapy and/or clinician entries. In a further example, presented data may be filtered according to its association with selected events. For example, a user may select an event such as unavailability, and the presented data may be limited to periods of unavailability. As another example, a user may select an event such as falls, and the presented data may be limited to periods immediately prior to and/or after the selected events. Such a presentation may allow a user to find a strong correlation between events and other therapy factors.

FIG. 22 illustrates one example of therapy factors that can be presented along a common timeline. In other examples, other therapy factors can be presented along a common timeline. Such therapy factors include: patient posture and/or activity level, stimulation therapy factors (including amplitude, programs and slot usage), recharge time, battery charge history, battery temperature, patient programmer usage (e.g., manual therapy adjustments), a subjective record of pain experienced by the patient, an objective record of one or more physiological conditions of the patient, a record representative of electrode impedances for electrodes of medical leads associated with the neurostimulator, lying transitions, sleep duration and/or events.

Figure 23:
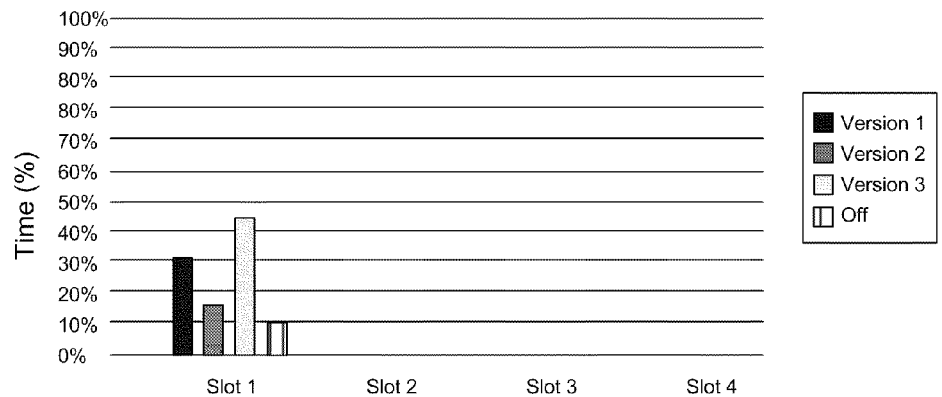
FIG. 23 illustrates an exemplary bar chart illustrating stimulation slot usage.

FIG. 23 illustrates an exemplary bar chart illustrating stimulation slot usage. FIG. 23 only illustrates data for a single slot, but the chart of FIG. 23 may also be populated with the data for additional slots. The data used to create the chart of FIG. 23 is same 90 pieces of 8-hour data used to create patient postures 512 (FIG. 22). Each bar % (shown as X %, Y % and Z %) is a sum of the time over the time period (e.g., last 90 days) that a version (therapy program) was active on a slot, divided by the total amount of time it was possible to have a version on. In addition, the chart of FIG. 23 also illustrates a sum of the time over the time period (e.g., last 90 days) that no therapy was applied for slot 1 (shown as A %). The sum total of X %, Y %, Z % and A % is 100%.

As an example: a user turns on only slot 1 and versions (therapy programs) 1 & 2. For the first 5 days he uses version 1, the next 10 days he uses version 2. The following 5 days he uses version 1 again, and the final 10 days he uses version 2. Then Slot 1 would have only 2 bars: Version 1 would have (5+5)/30=33% of the time, while version 2 has (10+10)/30=66%.

Figure 24:
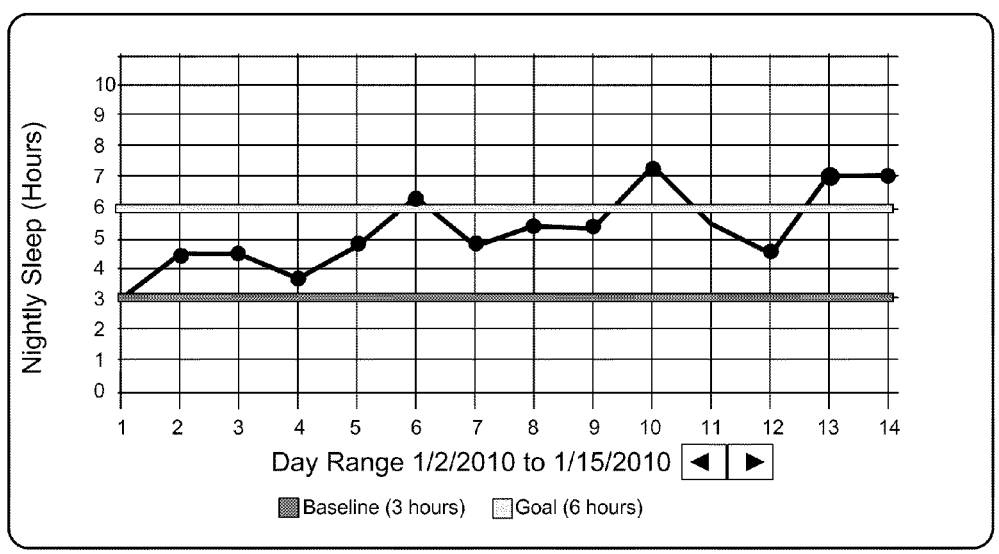
FIG. 24 illustrates an exemplary line chart illustrating daily sleep duration with indications of baseline sleep duration and goal sleep duration.

FIG. 24 illustrates an exemplary line chart illustrating daily sleep duration with indications of baseline sleep duration and goal sleep duration. The line chart illustrated in FIG. 24 provides objective evidence that the patient's condition has improved relative to a baseline average of sleep duration. FIG. 24 illustrates an objective representation of the effectiveness of a therapy, i.e., an increase in daily sleep duration over time. This can be useful to evaluate the effectiveness of a therapy as well as to provide patient and clinician perspective on the benefits of their therapy. For example over a long period of time, a patient or clinician may forget a baseline status of the patient and may not comprehend the effectiveness of a therapy.

The exemplary line chart illustrated in FIG. 24 provides one technique to establish the patient's baseline capabilities and track/trend outcomes over time. Such trend data may be stored either in an IMD that delivers the therapy or in a programmer associated with the IMD. Having the information stored in the IMD allows different programmers or clinics to review the data. Having the data stored in the programmer would enable remote retrieval of the data daily or weekly. This data could be analyzed by a clinic without the patient needing to come to the clinic.

In different examples, a line chart similar to that illustrated in FIG. 24 could correlate objective data such as the amount of time lying down (at night) with subjective data (such as the patient's goal to sleep 7 hours per night) or a subjective goal (become more active) to objective data (patient is walking 27 minutes per day).

While FIG. 24 illustrates a daily sleep duration, other therapy factors may be presented in a similar manner. Such therapy factors include, but are not limited to, factors such as therapy parameters for therapy applied to the patient, patient posture and/or activity level, lying transitions, a subjective record of pain experienced by the patient, an objective record of one or more physiological conditions of the patient and/or a measure of daily pain medication delivered to the patient. Any combination of these factors may be presented along a common timeline, e.g., as illustrated with respect to FIG. 22. Providing baseline and/or goals in combination with these factors provides context for a user to evaluate the effectiveness of a therapy over time.

Figure 25A:
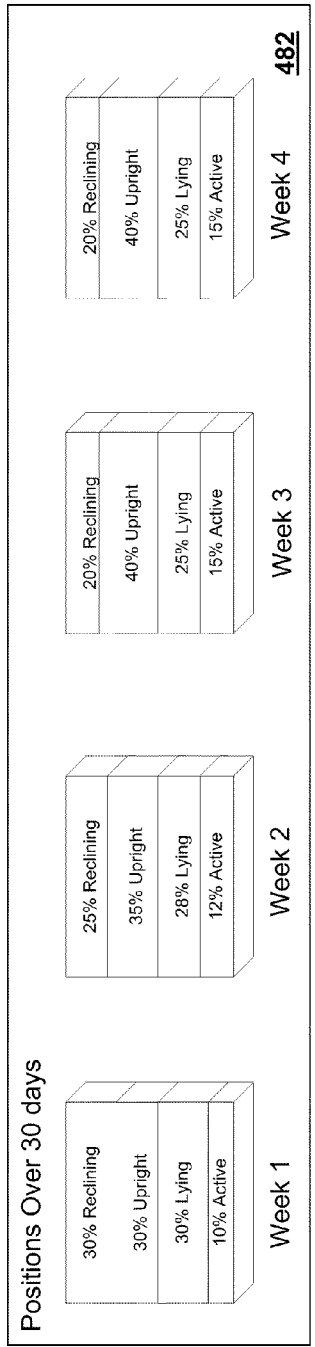
FIGS. 25A-25C illustrate patient posture rates over different intervals of the same data set.
Figure 25B:
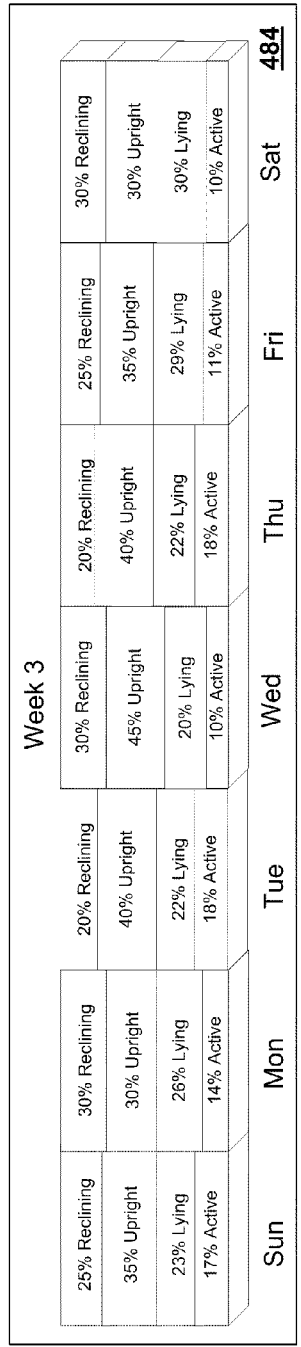
Figure 25C:
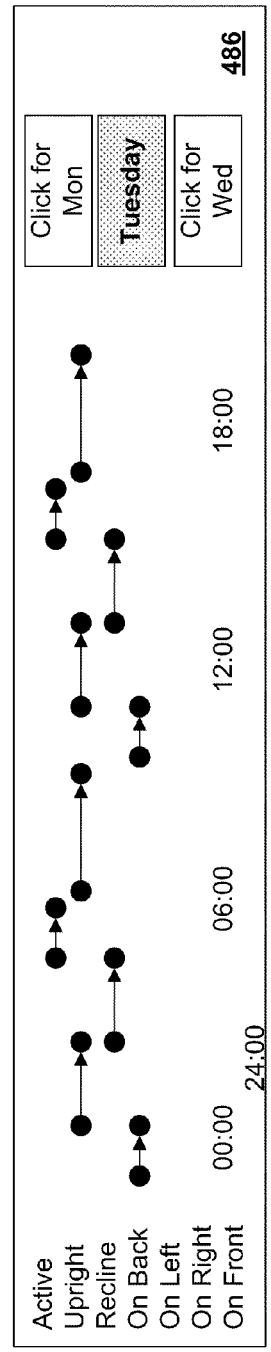

The patient posture rates presented in FIGS. 25A-25C may be shown on a screen of a clinician programmer. For example, patient posture rates may be presented along a common timeline in combination with other therapy factors associated with delivering electrical stimulation therapy.

FIGS. 25A-25C each represents only a portion of a screen shot. For example, patient posture rates 484 might be used instead of daily stimulation adjustments 472 of FIG. 20 such that patient posture rates would be presented along common timeline 470 with daily stimulation program usage 474 and daily stimulation amplitude ranges 476.

A user may select between the different time periods and resolutions of patient posture rates represented in FIGS. 25A-25C. For example, when viewing the presentation of patient posture rates 482 on a programmer, a user may could select week 3, e.g., by clicking on week 3 to transition to a presentation of patient posture rates 484. Likewise, when viewing the presentation of patient posture rates 484 on a programmer, a user may could select Tuesday, e.g., by clicking on Tuesday to transition to a presentation of patient posture rates 486. When viewing the presentation of patient posture rates 486 on a programmer, a user could quickly transition to an adjacent day by selecting one of the clickable areas "Click for Mon" or "Click for Wed" that are adjacent to the highlighted "Tuesday" button. Alternatively, user may select between the different intervals of FIGS. 25A-25C, e.g., using a zoom control similar to zoom control 514 (FIG. 22). Selecting different time periods for display of patient posture rates would also automatically transition different therapy factors associated with delivering electrical stimulation therapy displayed upon a common timeline to the selected time period such that all the displayed therapy factors associated with delivering electrical stimulation therapy would remain upon a common timeline. In this manner, a user may quickly select between different time periods of the same data set to review areas of interest at higher resolutions. Other techniques may also be used to receive user inputs for the selection of the period of a data set to be displayed, including, e.g., selectable tabs or a scroll bar.

In another example, a user can select a subset of a historical period in which therapy factors are displayed, e.g., as facilitated by times enabled control 513 (FIG. 22). Examples of possible subsets include data recorded during the mornings of the historical period, data recorded during the evenings of the historical period, data recorded during the night (sleeping time) of the historical period, weekends, work days or other subset of a historical period associated with a data set.

FIGS. 25A-25C represent patient posture rate of the same data set over three different timelines. More specifically, the data shown in FIG. 25A is shown in weekly intervals whereas the data shown in FIG. 25B is shown in daily intervals and the data shown in FIG. 25C is shown in 6 hour intervals. The presentation of patient posture rates 482 in FIG. 25A has a reduced resolution of the data set relative to the presentation of patient posture rates 484 in FIG. 25B. The shorter time period of the presentation of patient posture rates 484 in FIG. 25B (1 week) relative to the presentation of patient posture rates 482 in FIG. 25A (4 weeks) facilitates the higher resolution. For the same reasons, the presentation of patient posture rates 486 in FIG. 25C has a higher resolution of the data set (6 hr) relative to the presentation of patient posture rates 484 in FIG. 25B (daily). For example, patient posture may be recorded in 6 hour intervals such that the presentation of patient posture rates 486 in FIG. 25C may include each data point in the data set. Other posture recording intervals, such as 8 hour recording intervals, may also be used for patient posture rates 486.

Figure 26:
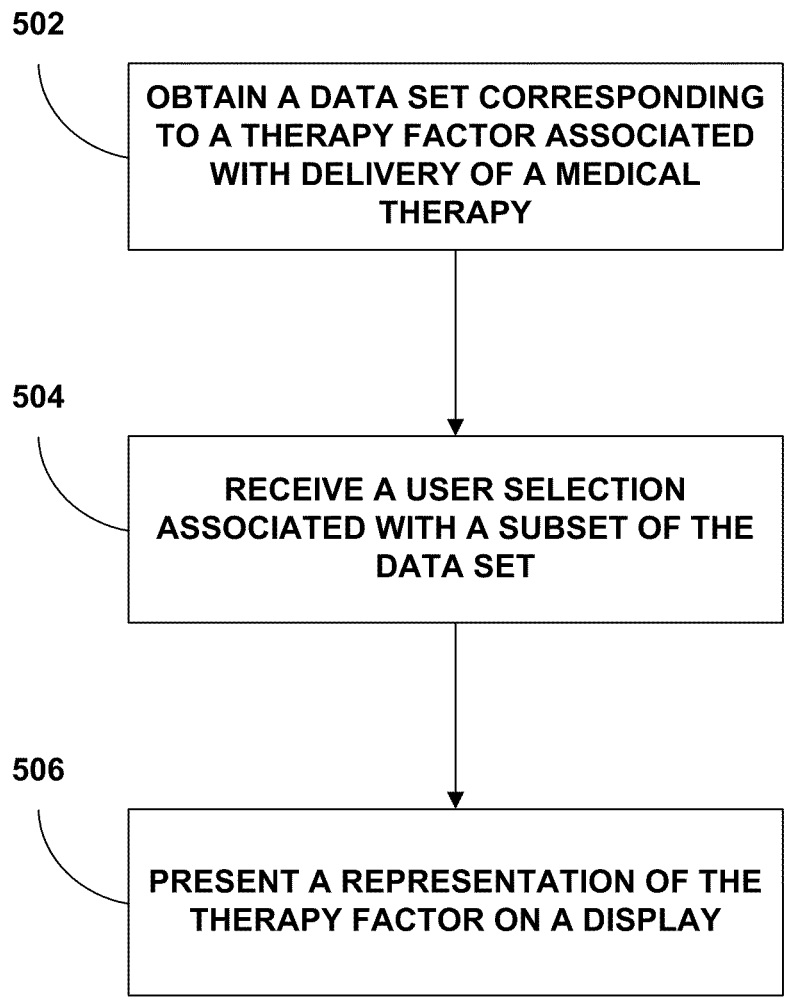
FIG. 26 illustrates techniques for presenting one or more therapy factors to a user.

FIG. 26 illustrates techniques for presenting one or more therapy factors to a user. For clarity, the techniques illustrated in FIG. 26 are discussed with respect to programmer 20 and the presentation of therapy factors illustrated in FIG. 22. First, programmer 20 obtains a data set corresponding to a therapy factor associated with delivery of a medical therapy to a patient with a medical system including an IMD, such as IMD 14 or IMD 26 (502). Next programmer 20 receives a user selection via user interface 106, the user selection is associated with a subset of the data set, the subset of the data set including less than all the information relating to the therapy factor in the data set. For example, as user may select a time period using control 513 (FIG. 22) (504). Then, processor 104 of programmer 20 presents a representation, corresponding to the subset of the data set, of the therapy factor on user interface 106, which includes a display a programmer 20 (506). In some examples, the subset of the data set includes data from portions of the data set that are non-sequential to each other. For example, selected daily time periods are not sequential to each other as the non-selected time periods are in between each selected daily time period.

The techniques described in this disclosure may be implemented, at least in part, in hardware, software, firmware or any combination thereof. For example, various examples of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The term "processor" or "processing circuitry" may generally refer to any of the foregoing logic circuitry, alone or in combination with other logic circuitry, or any other equivalent circuitry.

When implemented in software, the functionality ascribed to the systems and devices described in this disclosure may be embodied as instructions on a computer-readable storage medium such as random access memory (RAM), read-only memory (ROM), non-volatile random access memory (NVRAM), electrically erasable programmable read-only memory (EEPROM), FLASH memory, magnetic media, optical media, or the like. The instructions may be executed to cause one or more processors to support one or more examples of the functionality described in this disclosure.

In addition, it should be noted that the systems described herein may not be limited to treatment of a human patient. In alternative examples, these systems may be implemented in non-human patients, e.g., primates, canines, equines, pigs, and felines. These animals may undergo clinical or research therapies that my benefit from the subject matter of this disclosure.

Various aspects have been described. These and other aspects are within the scope of the following claims.

The invention claimed is:

1. A method comprising:
obtaining, by a computing device, a data set recorded over time during the delivery of electrical neurostimulation therapy to a patient, the data set corresponding to a plurality of therapy factors associated with delivery of the neurostimulation therapy to the patient with a medical system including an implantable medical device (IMD);
receiving, by the computing device, a user selection of a subset of the data set, the subset of the data set including less than all information relating to the therapy factors in the data set; and
in response to the user selection, presenting, by the computing device, a representation, corresponding to the subset of the data set, of the therapy factors on a display to facilitate user evaluation of the neurostimulation therapy based on the therapy factors,
wherein presenting the representation of the therapy factors corresponding to the subset of the data set comprises presenting representations, corresponding to the subset of the data set, of two or more of the therapy factors simultaneously along a common timeline on the display, and
wherein the representations of the two or more therapy factors comprise at least one of a representation of usage of one or more programs of the neurostimulation therapy along the common timeline, a representation of one or more parameters of one or more programs of the neurostimulation therapy along the common timeline, or a representation of adjustments to one or more parameters of one or more programs of the neurostimulation therapy along the common timeline.

2. The method of claim 1, wherein the subset of the data set includes data from portions of the data set that are recorded non-sequentially to each other.

3. The method of claim 1, wherein the user selection includes a selection of a daily time period.

4. The method of claim 1, wherein the user selection includes a selection of at least one of a group of:
a therapeutic element in the medical system;
a therapy setting associated with delivering a portion of the neurostimulation therapy to the patient with the medical system;
a patient activity level;
a patient posture;
a patient posture and activity level;
a patient mobility;
a patient record of therapy outcome;
an objective record of therapy outcome;
an event recorded during the delivery of the neurostimulation therapy to the patient with the medical system; or
a recharge status of the IMD.

5. The method of claim 4, wherein the user selection includes a selection of two or more of the group.

6. The method of claim 1,
wherein the two or more of the therapy factors include an objective record of the neurostimulation therapy delivered to the patient and one or more of a group of:
a record of patient posture;
a record of a battery charge history of a battery of the IMD;
a subjective record of pain experienced by the patient;
a subjective record of paresthesia experienced by the patient;
an objective record of one or more physiological conditions of the patient; or
a record representative of electrode impedances for electrodes of medical leads associated with the IMD.

7. The method of claim 6, wherein the representation of the therapy factors comprises a representation of the objective record of neurostimulation therapy delivered to the patient, and the representation of the objective record of the neurostimulation therapy delivered to the patient includes a representation of one or more of a set of:
a list of stimulation programs along the common timeline;
a series of graphical representations of the medical leads and active electrodes corresponding to the neurostimulation therapy along the common timeline;
indications of stimulation activity along the common timeline;
indications of stimulation programs from two or more program slots of the electrical stimulation therapy along the common timeline;
indications of amplitudes of the neurostimulation therapy along the common timeline; or
indications of the prevalence of manual patient adjustments of the neurostimulation therapy along the common timeline.

8. A method comprising:
obtaining, by a computing device, a data set recorded over time during the delivery of electrical neurostimulation therapy to a patient, the data set corresponding to a plurality of therapy factors associated with delivery of the neurostimulation therapy to the patient with a medical system including an implantable medical device (IMD);
receiving, by the computing device, a user selection of a subset of the data set, the subset of the data set including less than all information relating to the therapy factors in the data set; and
in response to the user selection, presenting, by the computing device, a representation, corresponding to the subset of the data set, of the therapy factors on a display of the computing device to facilitate user evaluation of the neurostimulation therapy based on the therapy factors,
wherein presenting the representation of the therapy factors corresponding to the subset of the data set comprises presenting representations, corresponding to the subset of the data set, of two or more of the therapy factors simultaneously on the display of the computing device, and
wherein the two or more of the therapy factors include a record of patient posture and a breakdown of individual stimulation slots usage over time, each of the slots including one or more programs of the neurostimulation therapy that target at least one of a different symptom or a different area of pain than other slots.

9. The method of claim 1, wherein the therapy factors include at least one of a group of:

an objective record of the neurostimulation therapy delivered to the patient, a record of patient posture;

a record of a battery charge history of a battery of the IMD;

a subjective record of pain experienced by the patient;

a subjective record of paresthesia experienced by the patient;

an objective record of one or more physiological conditions of the patient; or a record representative of electrode impedances for electrodes of medical leads associated with the IMD.

10. The method of claim 1, further comprising presenting a representation of the therapy factors corresponding to the data set on the display at a reduced resolution, wherein presenting the representations of the therapy factors corresponding to the subset of the data set comprises presenting the representations of the therapy factors corresponding to the subset of the data set at a higher resolution than the reduced resolution.

11. The method of claim 1, wherein the method further comprises delivering the electrical neurostimulation therapy with the IMD to the patient to treat pain of the patient.

12. The method of claim 1, wherein the representations of the two or more therapy factors further comprise the representation of one or more parameters, and the representation of one or more parameters comprises a representation of different sets of active electrodes and inactive electrodes for the neurostimulation therapy along the common timeline.

13. The method of claim 12, wherein the representation of the different sets of active electrodes comprises a graphical representation of active cathode electrodes and active anode electrodes.

14. The method of claim 12, wherein the representations of the two or more therapy factors further comprise at least one of indications of areas of a body of the patient corresponding to a subjective record of pain experienced by the patient along the common timeline or indications of areas of the body of the patient corresponding to a subjective record of paresthesia experienced by the patient along the common timeline.

15. The method of claim 14, wherein the representations of the two or more therapy factors comprise the representation of usage of one or more programs of the neurostimulation therapy, and the representation of usage of one or more programs comprises a representation of usage of at least one of different programs of the neurostimulation therapy or different slots of the neurostimulation therapy along the common timeline, each of the slots including one or more programs of the neurostimulation therapy that target at least one of a different symptom or a different area of pain than other slots.

16. The method of claim 12, wherein the representations of the two or more therapy factors comprise the representation of usage of one or more programs of the neurostimulation therapy, and the representation of usage of one or more programs comprises a representation of usage of at least one of different programs of the neurostimulation therapy or different slots of the neurostimulation therapy along the common timeline, each of the slots including one or more programs of the neurostimulation therapy that target at least one of a different symptom or a different area of pain than other slots.

17. The method of claim 1, wherein the representations of the two or more therapy factors comprise the representation of usage of one or more programs of the neurostimulation therapy.

18. The method of claim 17, wherein the representation of usage of one or more programs comprises a representation of usage of at least one of different programs of the neurostimulation therapy or different slots of the neurostimulation therapy along the common timeline, each of the slots including one or more programs of the neurostimulation therapy that target at least one of a different symptom or a different area of pain than other slots.

19. The method of claim 18, wherein the representations of the two or more therapy factors comprise a representation of recharges of a battery of the IMD along the common timeline.

20. The method of claim 18, wherein the representations of the two or more therapy factors comprise at least one of a patient activity level or a patient posture.

21. The method of claim 18, wherein the representations of the two or more therapy factors comprise the representation of adjustments, and wherein the representation of the adjustments comprises indications of manual patient adjustments to the one or more parameters of the one or more programs of the neurostimulation therapy along the common timeline.

22. The method of claim 21, wherein the representations of the two or more therapy factors comprise a representation of an amplitude range of the manual patient adjustments along the common timeline.

23. The method of claim 1, wherein the representations of the two or more therapy factors comprise the representation of adjustments, and wherein the representation of the adjustments comprises indications of manual patient adjustments to the one or more parameters of the one or more programs of the neurostimulation therapy along the common timeline.

24. The method of claim 23, wherein the representations of the two or more therapy factors comprise a representation of an amplitude range of the manual patient adjustments along the common timeline.

25. The method of claim 1, wherein the representations of the two or more therapy factors comprise a representation of recharges of a battery of the IMD along the common timeline.

26. The method of claim 1, wherein the representations of the two or more therapy factors comprise at least one of a patient activity level or a patient posture.

27. The method of claim 8, further comprising delivering the electrical neurostimulation therapy with the IMD to the patient to treat pain of the patient.

28. A programmer for an implantable medical device (IMD), the programmer comprising:

a user interface;

a telemetry circuit configured to transfer data to and from the IMD;

a display; and a processor, wherein the processor is configured to:

obtain a data set recorded over time during the delivery of electrical neurostimulation therapy to a patient, the data set corresponding to a plurality of therapy factors associated with delivery of the neurostimulation therapy to the patient with the IMD;

receive, via the user interface, a user selection of a subset of the data set, the subset of the data set including less than all the information relating to the therapy factors in the data set; and in response to the user selection, present a representation, corresponding to the subset of the data set, of the therapy factors on the display to facilitate user evaluation of the neurostimulation therapy based on the therapy factors, wherein the processor, to present the representation of the therapy factors corresponding to the subset of the data set, is further configured to present representations, corresponding to the subset of the data set, of two or more of the therapy factors simultaneously along a common timeline on the display, and wherein the representations of the two or more therapy factors comprise at least one of a representation of usage of one or more programs of the neurostimulation therapy along the common timeline, a representation of one or more parameters of one or more programs of the neurostimulation therapy along the common timeline, or a representation of adjustments to one or more parameters of one or more programs of the neurostimulation therapy along the common timeline.

29. The programmer of claim 28, wherein the subset of the data set includes data from portions of the data set that are recorded non-sequentially to each other.

30. The programmer of claim 28, wherein the user selection includes a selection of a daily time period.

31. The programmer of claim 28, wherein the user selection includes a selection of at least one of a group of:
a therapeutic element of the IMD;
a therapy setting associated with delivering a portion of the neurostimulation therapy to the patient with the IMD;
a patient activity level;
a patient posture;
a patient posture and activity level;
a patient mobility;
a patient record of therapy outcome;
an objective record of therapy outcome;
an event recorded during the delivery of the neurostimulation therapy to the patient with the IMD; or
a recharge status of the IMD.

32. The programmer of claim 28, wherein the two or more therapy factors include an objective record of the neurostimulation therapy delivered to the patient and one or more of a group of:
a record of patient posture;
a record of a battery charge history of a battery of the IMD;
a subjective record of pain experienced by the patient;
a subjective record of paresthesia experienced by the patient;
an objective record of one or more physiological conditions of the patient; or
a record representative of electrode impedances for electrodes of medical leads associated with the IMD.

33. The programmer of claim 32, wherein the representation of the therapy factors comprises a representation of the objective record of the neurostimulation therapy delivered to the patient, and the representation of the objective record of the neurostimulation therapy delivered to the patient includes a representation of one or more of a set of:
a list of stimulation programs along the common timeline;
a series of graphical representations of the medical leads and active electrodes corresponding to the neurostimulation therapy along the common timeline;
indications of stimulation activity along the common timeline;
indications of stimulation programs from two or more program slots of the neurostimulation therapy along the common timeline;
indications of amplitudes of the neurostimulation therapy along the common timeline; and
indications of the prevalence of manual patient adjustments of the neurostimulation therapy along the common timeline.

34. The programmer of claim 28, wherein the processor is configured to program the IMD to deliver the electrical neurostimulation therapy to the patient to treat pain of the patient.

35. The programmer of claim 28, wherein the representations of the therapy factors further comprise the representation of one or more parameters, and the representation of one or more parameters comprises a representation of different sets of active electrodes and inactive electrodes for the neurostimulation therapy along the common timeline.

36. The programmer of claim 35, wherein the representation of the different sets of active electrodes comprises a graphical representation of active cathode electrodes and active anode electrodes.

37. The programmer of claim 35, wherein the representations of the two or more therapy factors further comprise at least one of indications of areas of a body of the patient corresponding to a subjective record of pain experienced by the patient along the common timeline or indications of areas of the body of the patient corresponding to a subjective record of paresthesia experienced by the patient along the common timeline.

38. The programmer of claim 28, wherein the representations of the two or more therapy factors comprise the representation of usage of one or more programs of the neurostimulation therapy.

39. The programmer of claim 38, wherein the representation of usage of one or more programs comprises a representation of usage of at least one of different programs of the neurostimulation therapy or different slots of the neurostimulation therapy along the common timeline, each of the slots including one or more programs of the neurostimulation therapy that target at least one of a different symptom or a different area of pain than other slots.

40. The programmer of claim 28, wherein the representations of the two or more therapy factors comprise the representation of adjustments, and wherein the representation of the adjustments comprises indications of manual patient adjustments to the one or more parameters of the one or more programs of the neurostimulation therapy along the common timeline.

41. The programmer of claim 40, wherein the representations of the two or more therapy factors comprise a representation of an amplitude range of the manual patient adjustments along the common timeline.

42. The programmer of claim 28, wherein the representations of the two or more therapy factors comprise a representation of recharges of a battery of the IMD along the common timeline.

43. The programmer of claim 28, wherein the representations of the two or more therapy factors comprise at least one of a patient activity level or a patient posture.

44. A system comprising:
an implantable medical device (IMD) configured to deliver electrical neurostimulation therapy to a patient; and
a programmer for the implantable medical device, the programmer comprising:
a user interface;
a telemetry circuit configured to transfer data to and from the IMD;
a display; and a processor, wherein the processor is configured to:
  obtain a data set recorded over time during the delivery of the electrical neurostimulation therapy to the patient, the data set corresponding to a plurality of therapy factors associated with delivery of the neurostimulation therapy to the patient with the IMD;
  receive, via the user interface, a user selection of a subset of the data set, the subset of the data set including less than all the information relating to the therapy factors in the data set; and
  in response to the user selection, present a representation, corresponding to the subset of the data set, of the therapy factors on the display to facilitate user evaluation of the neurostimulation therapy based on the therapy factors,
  wherein the processor, to present the representation of the therapy factors corresponding to the subset of the data set, is further configured to present representations, corresponding to the subset of the data set, of two or more of the therapy factors simultaneously along a common timeline on the display, and
  wherein the representations of the two or more therapy factors comprise at least one of a representation of usage of one or more programs of the neurostimulation therapy along the common timeline, a representation of one or more parameters of one or more programs of the neurostimulation therapy along the common timeline, or a representation of adjustments to one or more parameters of one or more programs of the neurostimulation therapy along the common timeline.

45. The system of claim 44, wherein the representations of the therapy factors further comprise the representation of one or more parameters, and the representation of one or more parameters comprises a representation of different sets of active electrodes and inactive electrodes for the neurostimulation therapy along the common timeline.

46. The system of claim 45, wherein the representations of the two or more therapy factors further comprise at least one of indications of areas of a body of the patient corresponding to a subjective record of pain experienced by the patient along the common timeline or indications of areas of the body of the patient corresponding to a subjective record of paresthesia experienced by the patient along the common timeline.

47. The system of claim 44, wherein the representations of the two or more therapy factors comprise the representation of usage of one or more programs of the neurostimulation therapy.

48. The system of claim 47, wherein the representation of usage of one or more programs comprises a representation of usage of at least one of different programs of the neurostimulation therapy or different slots of the neurostimulation therapy along the common timeline, each of the slots including one or more programs of the neurostimulation therapy that target at least one of a different symptom or a different area of pain than other slots.

49. The system of claim 44, wherein the representations of the two or more therapy factors comprise the representation of adjustments, and wherein the representation of the adjustments comprises indications of manual patient adjustments to the one or more parameters of the one or more programs of the neurostimulation therapy along the common timeline.

50. The system of claim 44, wherein the representations of the two or more therapy factors comprise a representation of recharges of a battery of the IMD along the common timeline.

51. The system of claim 44, wherein the representations of the two or more therapy factors comprise at least one of a patient activity level or a patient posture.

52. A programmer for an implantable medical device (IMD), the programmer comprising:
  a user interface;
  a telemetry circuit configured to transfer data to and from the IMD;
  a display; and
  a processor, wherein the processor is configured to:
    obtain a data set recorded over time during the delivery of electrical neurostimulation therapy to a patient, the data set corresponding to a plurality of therapy factors associated with delivery of the neurostimulation therapy to the patient with the IMD;
    receive, via the user interface, a user selection of a subset of the data set, the subset of the data set including less than all the information relating to the therapy factors in the data set; and
    in response to the user selection, present a representation, corresponding to the subset of the data set, of the therapy factors on the display to facilitate user evaluation of the neurostimulation therapy based on the therapy factors,
    wherein the processor, to present the representation of the therapy factors corresponding to the subset of the data set, is further configured to present representations, corresponding to the subset of the data set, of two or more of the therapy factors simultaneously along a common timeline on the display, and
    wherein the two or more of the therapy factors include a record of patient posture and a breakdown of individual stimulation slots usage over time, each of the slots including one or more programs of the neurostimulation therapy that target at least one of a different symptom or a different area of pain than other slots.

53. The programmer of claim 52, wherein the processor is configured to program the IMD to deliver the electrical neurostimulation therapy to the patient to treat pain of the patient.

54. A system comprising:
  an implantable medical device (IMD) configured to deliver electrical neurostimulation therapy to a patient; and
  a programmer for the implantable medical device, the programmer comprising:
    a user interface;
    a telemetry circuit configured to transfer data to and from the implantable medical device;
    a display; and
    a processor, wherein the processor is configured to:
      obtain a data set recorded over time during the delivery of the electrical neurostimulation therapy to the patient, the data set corresponding to a plurality of therapy factors associated with delivery of the neurostimulation therapy to the patient with the IMD;
      receive a user selection via the user interface, wherein the user selection is an indication of a subset of the data set, the subset of the data set including less than all the information relating to the therapy factors in the data set; and in response to the user selection, present a representation, corresponding to the subset of the data set, of the therapy factors on the display to facilitate user evaluation of the neurostimulation therapy based on the therapy factors, wherein the programmer, to present the representation of the therapy factors corresponding to the subset of the data set, is further configured to present representations, corresponding to the subset of the data set, of two or more of the therapy factors simultaneously along a common timeline on the display, and wherein the two or more of the therapy factors include a record of patient posture and a breakdown of individual stimulation slots usage over time, each of the slots including one or more programs of the neurostimulation therapy that target at least one of a different symptom or a different area of pain than other slots.

\* \* \* \* \*